US012606622B2

(12) United States Patent
Liu et al.

(10) Patent No.: US 12,606,622 B2
(45) Date of Patent: Apr. 21, 2026

(54) HETEROMULTIMERIC PROTEINS AND METHODS OF USE THEREOF

(71) Applicant: AB Studio Inc., Hayward, CA (US)

(72) Inventors: Yue Liu, Foster City, CA (US); Jianbo Dong, Santa Clara, CA (US); Bo Wang, San Carlos, CA (US)

(73) Assignee: AB Studio Inc., Hayward, CA (US)

( * ) Notice: Subject to any disclaimer, the term of this patent is extended or adjusted under 35 U.S.C. 154(b) by 1090 days.

(21) Appl. No.: 17/598,826

(22) PCT Filed: Mar. 27, 2020

(86) PCT No.: PCT/US2020/025469
§ 371 (c)(1),
(2) Date: Sep. 27, 2021

(87) PCT Pub. No.: WO2020/198683
PCT Pub. Date: Oct. 1, 2020

(65) Prior Publication Data
US 2022/0185887 A1 Jun. 16, 2022

Related U.S. Application Data

(60) Provisional application No. 62/825,726, filed on Mar. 28, 2019.

(51) Int. Cl.
| | |
|---|---|
| *C07K 16/28* | (2006.01) |
| *C07K 16/06* | (2006.01) |
| *C07K 16/32* | (2006.01) |

(52) U.S. Cl.
CPC ...... *C07K 16/2809* (2013.01); *C07K 16/2878* (2013.01); *C07K 16/2887* (2013.01); *C07K 16/32* (2013.01); *C07K 2317/31* (2013.01); *C07K 2317/526* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly | |
| 5,591,828 A | 1/1997 | Bosslet | |
| 5,731,168 A | 3/1998 | Carter | |
| 6,326,193 B1 | 12/2001 | Liu | |
| 7,183,076 B2 | 2/2007 | Arathoon et al. | |
| 8,592,562 B2 | 11/2013 | Kannan et al. | |
| 8,642,745 B2 | 2/2014 | Arathoon et al. | |
| 2012/0149876 A1* | 6/2012 | Von Kreudenstein | ...................... |
| | | | C07K 16/00 |
| | | | 530/387.3 |
| 2013/0089541 A1 | 4/2013 | D'Angelo et al. | |
| 2013/0195849 A1 | 8/2013 | Spreter et al. | |
| 2013/0336973 A1 | 12/2013 | Spreter Von Kreudenstein et al. | |
| 2013/0336981 A1 | 12/2013 | De Kruif et al. | |

| | | | |
|---|---|---|---|
| 2016/0319036 A1 | 11/2016 | Bruenker | |
| 2018/0023810 A1* | 1/2018 | Karkow | .................... F23N 5/00 |
| | | | 431/75 |
| 2018/0362668 A1 | 12/2018 | Xu | |
| 2019/0023810 A1 | 1/2019 | Sasisekharan et al. | |
| 2019/0062434 A1 | 2/2019 | Han et al. | |
| 2019/0218310 A1* | 7/2019 | Van Der Woning | ........................ |
| | | | C07K 16/468 |
| 2023/0399408 A1 | 12/2023 | Zaman et al. | |
| 2024/0109963 A1 | 4/2024 | Chaudhary et al. | |

FOREIGN PATENT DOCUMENTS

| | | | | |
|---|---|---|---|---|
| CA | 3031082 A1 * | 1/2018 | ......... | C07K 16/1018 |
| EP | 0314317 A1 | 5/1989 | | |
| EP | 0404097 A2 | 12/1990 | | |
| EP | 3392276 A1 | 10/2018 | | |
| KR | 20140019385 A | 2/2014 | | |
| WO | 198705330 A1 | 9/1987 | | |
| WO | 198902922 A1 | 4/1989 | | |
| WO | 199301161 A1 | 1/1993 | | |
| WO | 199704801 A1 | 2/1997 | | |
| WO | 2001029058 A1 | 4/2001 | | |
| WO | WO-0177342 A1 * | 10/2001 | ......... | A61K 39/3955 |
| WO | 200196584 A2 | 12/2001 | | |
| WO | 200196584 A3 | 1/2003 | | |
| WO | 2012123949 A1 | 9/2012 | | |

(Continued)

OTHER PUBLICATIONS

Wu et al. Protein Engineering, Design & Selection. 31(7-8): 249-256: Published: Apr. 18, 2018 (Year: 2018).*
Adelman, J.P. et al. (Sep. 1983). "In Vitro Deletional Mutagenesis For Bacterial Production Of The 20,000-Dalton Form Of Human Pituitary Growth Hormone," DNA 2(3):183-193. (Abstract only).
Al-Lazikani, B. et al. (1997). "Standard Conformations for the Canonical Structures of Immunoglobulins," J. Mol. Biol. 273:927-948.
Anonymous (No Date) "Developing of Natural Bispecific Antibody and Thereof Use," AB Studio, 15 pages.
Aplin, J.D. et al. (May 1981). "Preparation, Properties, and Applications of Carbohydrate Conjugates of Proteins and Lipids," Clinical Reviews in Biochemistry and Molecular Biology, pp. 259-306.

(Continued)

*Primary Examiner* — Juliet C Switzer
*Assistant Examiner* — Katherine Ann Holtzman
(74) *Attorney, Agent, or Firm* — Morrison & Foerster LLP

(57) ABSTRACT

The present application provides heteromultimeric proteins, such as bispecific antibodies, comprising a first antibody heavy chain constant domain 3 (CH3)-containing polypeptide having a substitution relative to a wildtype CH3 domain at amino acid position 354 with a bulky hydrophobic amino acid, and/or a second CH3-containing polypeptide comprising a substitution relative to a wildtype CH3 domain at ammo acid position 347 with a negatively charged amino acid residue. Also provided are polypeptides, nucleic acids and vectors encoding such polypeptides, pharmaceutical compositions, methods of preparation and methods of treatment using the heteromultimeric proteins.

19 Claims, 27 Drawing Sheets

Specification includes a Sequence Listing.

(56)                References Cited

FOREIGN PATENT DOCUMENTS

| WO | 2014142591 A1 | 9/2014 | |
| WO | 2017034770 A1 | 3/2017 | |
| WO | WO-2017193032 A2 * | 11/2017 | ........... A61K 39/395 |
| WO | 2018014855 A1 | 1/2018 | |
| WO | WO-2018016881 A1 * | 1/2018 | ........ C07K 16/1018 |
| WO | 2018028125 A1 | 2/2018 | |
| WO | WO-2018026942 A1 * | 2/2018 | ........... C07K 16/005 |
| WO | 2019028125 A1 | 2/2019 | |
| WO | 2020159918 A2 | 8/2020 | |

OTHER PUBLICATIONS

Atwell, S. et al. (1997). "Stable Heterodimers From Remodeling The Domain Interface Of A Homodimer Using A Phage Display Library," J. Mol. Biol. 270 (1):26-35.

Berg, J. et al. (Jun. 1991). "Bispecific Antibodies That Mediate Killing of Cells Infected the Human Immunodeficiency Virus of Any Strain," Proc. Natl. Acad. Sci. USA 88:4723-4727.

BLAST Basic Local Alignment Search Tool, 1 page.

Burton, D.R. (1985). "Immunoglobulin G: Functional Sites," Molec. Immunol. 22(3):161-206.

Carter, P. (2001). "Bispecific Human IgG by Design," Immunol. Methods 248:7-15.

Chamow, S.M. et al. (1994). "A Humanized, Bispecific Immunoadhesin-Antibody That Retargets CD3+ Effectors to Kill HIV-1-Infected Cells," J. Immunol. 153:4268-4280.

Chothia, C. et al. (Aug. 20, 1987). "Canonical Structures for the Hypervariable Regions of Immunoglobulins," J. Mol. Biol. 196(4):901-917.

Chothia, C. et al. (Dec. 21/28, 1989). "Conformations of Immunoglobulin Hypervariable Regions," Nature 342 (6252):877-883.

Chothia, C. et al. (Dec. 5, 1985). "Domain Association In Immunoglobulin Molecules. The Packing Of Variable Domains," J. Mol. Biol. 186(3):651-663.

Cunningham, B.C. et al. (Jun. 2, 1989). "High-Resolution Epitope Mapping of hGH-Receptor Interactions by Alanine-Scanning Mutagenesis," Science 244:1081-1085.

Endo, Y. et al. (2003). "High-Throughput, Genome-Scale Protein Production Method Based On The Wheat Germ Cell-Free Expression System," Biotechnol. Adv. 21:695-713.

GenBank Accession No. AAA52770.1 "Immunoglobulin Delta-Chain, Partial [Homo sapiens]," 2 pages.

GenBank Accession No. AAA52771.1 "Immunoglobulin Delta-Chain, Partial [Homo sapiens]," 2 pages.

GenBank Accession No. AAA58989.1 "Immunoglobulin Kappa Chain Constant Region, Partial [Homo sapiens]," 2 pages.

GenBank Accession No. AAB59393.1 "Immunoglobulin Gamma-2 Heavy Chain, Partial [Homo sapiens]," 3 pages.

GenBank Accession No. AAB59394.1 "Immunoglobulin Gamma-4 Heavy Chain, Partial [Homo sapiens]," 2 pages.

GenBank Accession No. AAB59395.1 "Immunoglobulin Epsilon Chain Constant Region, Partial [Homo sapiens]," 3 pages.

GenBank Accession No. AAB59396.1 "Immunoglobulin Alpha-2 Heavy Chain, Partial [Homo sapiens], 3 pages.

GenBank Accession No. AAC82527.1 "Immunoglobulin Gamma-1 Heavy Chain Constant Region, Partial [Homo sapiens]," 3 pages.

GenBank Accession No. AAT74070.1 "Immunoglobulin Alpha 1 Heavy Chain Constant Region, Partial [Homo sapiens]," 3 pages.

GenBank Accession No. AY647978.1 "Homo sapiens Immunoglobulin Alpha 1 Heavy Chain Constant Region Gene, Partial Cds," 2 pages.

GenBank Accession No. CAB37838.1 "Immunoglobulin M Heavy Chain, Partial [Homo sapiens], " 2 pages.

GenBank Accession No. J00221.1/J00230.1/K01316.1/AH005273.2 "Homo sapiens Immunoglobulin Gamma-2 Heavy Chain (IgH), Immunoglobulin Gamma-4 Heavy Chain (IgH), Immunoglobulin Epsilon Chain Constant Region (IgH), and Immunoglobulin Alpha-2 Heavy Chain (IgH) Genes, Partial Cds," 9 pages.

GenBank Accession No. J00228.1/AH007035.2 "Homo sapiens Clone Cosmid Ig13 Immunoglobulin Gamma-3 Heavy Chain Constant Region (IGHG3) and Immunoglobulin Gamma-1 Heavy Chain Constant Region (IGHG1) Genes, Partial Cds; Epsilon-1 Pseudogene (IGHEP1) Pseudogene, Partial Sequence; and Immunoglobulin Alpha-1 . . . ," 6 pages.

GenBank Accession No. J00241.1/AH002839.2 "Homo sapiens Chromosome 2 Immunoglobulin Kappa Chain Variable Region (IGKV) Gene, Complete Sequence; and Immunoglobulin Kappa Chain Constant Region (IGKC) Gene, Partial Cds," 3 pages.

GenBank Accession No. P01860 "RecName: Full=Immunoglobulin Heavy Constant Gamma 3; AltName: Full=HDC; AltName: Full=Heavy Chain Disease Protein; AltName: Full=Ig Gamma-3 Chain C Region," 8 pages.

GenBank Accession No. X03604.1 "Human C Gamma 3 Gene For IgG G3m(b) Heavy Chain C-Region From EZZ (Individual II-4 of TOU)," 2 pages.

GenBank Accession No. X57086.1 "H.sapiens mRNA for IgM Heavy Chain Constant Domain," 2 pages.

Greenberg, A.S. et al. (Mar. 9, 1995). "A New Antigen Receptor Gene Family That Undergoes Rearrangement And Extensive Somatic Diversification In Sharks" Nature 374(6518):168-173.

Hamers-Casterman, C. et al. (Jun. 3, 1993). "Naturally Occurring Antibodies Devoid of Light Chains," Nature 363:446-448.

Hassanzadeh-Ghassabeh, G. et al. (2013, e-pub. Jun. 4, 2013). "Nanobodies and their Potential Applications," Nanomedicine (Lond) 8(6):1013-1026.

Holliger, P. et al. (Jul. 1993). "Diabodies: Small Bivalent and Bispecific Antibody Fragments," Proc. Natl. Acad. Sci. USA 90:6444-6448.

IMGT Scientific Chart, 5 pages.

IMGT Scientific Chart, 6 pages.

IMGT Scientific Chart, 7 pages.

International Preliminary Report on Patentability, issued Sep. 28, 2021 for PCT Application No. PCT/US2020/025469, filed Mar. 27, 2020, 11 pages.

International Search Report and Written Opinion, mailed Sep. 2, 2020 for PCT Application No. PCT/US2020/025469, filed Mar. 27, 2020, 11 pages.

Jones, P. et al. (May 29, 1986). "Replacing The Complementarity-Determining Regions In A Human Antibody With Those From A Mouse," Nature 321:522-525.

Kabat, E.A. et al. (1991). Sequences of Proteins of Immunological Interest, 5th Ed. Public Health Service, National Institutes of Health, Bethesda MD., Table of Contents, 21 pages.

Kennedy, A.D. et al. (2003, e-pub. Sep. 5, 2002). "An Anti-C3b(i) mAb Enhances Complement Activation, C3b(i) Deposition, and Killing of CD20+ Cells By Rituximab," Blood 101:1071-1079.

Merchant, A. M. et al. (Jul. 1998). "An Efficient Route To Human Bispecific IgG," Nature Biotechnology 16:677-681.

Morrison, S.L. et al. (Nov. 1984). "Chimeric Human Antibody Molecules: Mouse Antigen-Binding Domains With Human Constant Region Domains," Proc. Natl. Acad. Sci. USA 81:6851-6855.

NCBI Reference Sequence NM 001066.2 "Homo sapiens TNF Receptor Superfamily Member 1B (TNFRSF1B), mRNA," 6 pages.

NCBI Reference Sequence NM_000043.5 "Homo sapiens Fas Cell Surface Death Receptor (FAS), Transcript Variant 1, mRNA," 6 pages.

NCBI Reference Sequence NP_000034.1 "Tumor Necrosis Factor Receptor Superfamily Member 6 Isoform 1 Precursor [Homo sapiens]," 4 pages.

NCBI Reference Sequence NP_001057.1 "Tumor Necrosis Factor Receptor Superfamily Member 1B Precursor [Homo sapiens]," 4 pages.

Plückthun, A. (1994). "Antibodies from Escherichia coli," in Chapter 11 The Pharmacology of Monoclonal Antibodies, vol. 113, Rosenburg and Moore eds., Springer-Verlag, New York, pp. 269-315, 48 pages.

Presta, L.G. (1992). "Antibody Engineering," Current Opinion in Structural Biology 2:593-596.

Remington's Pharmaceutical Sciences. (1980). 16th edition, Osol, A. Ed, pp. 1-2, (Table of Contents Only).

(56) References Cited

OTHER PUBLICATIONS

Ridgway, J.B.B. et al. (1996). "Knobs-Into-Holes' Engineering of Antibody CH3 Domains for Heavy Chain Heterodimerization," Protein Engineering 9(7):617-621.

Riechmann, L. et al. (Mar. 24, 1988). "Reshaping Human Antibodies for Therapy," Nature 332:323-329.

Running Deer, J. et al. (May-Jun. 2004, e-pub. Mar. 10, 2004). "High-Level Expression Of Proteins In Mammalian Cells Using Transcription Regulatory Sequences From The Chinese Hamster EF-1Alpha Gene," Biotechnol. Prog. 20(3):880-889.

Sambrook, J. et al. (2001). Molecular Cloning: A Laboratory Manual Cold Spring Harbor Laboratory Press, Cold Spring Harbor,N. Y., 3rd ed., 1 page, Table of Contents.

Sitaraman, K. et al. (2009). "High-Throughput Protein Expression Using Cell-Free System," Methods Mol. Biol. 498:229-244.

Spirin, A.S. (Oct. 2004). "High-Throughput Cell-Free Systems For Synthesis Of Functionally Active Proteins," Trends Biotechnol. 22(10):538-545.

Terui, Y. et al. (2006, e-pub. Dec. 18, 2005). "Blockade of Bulky Lymphoma-Associated CD55 Expression by RNA Interference Overcomes Resistance To Complement-Dependent Cytotoxicity With Rituximab," Cancer Science 97(1):72-79.

U-Tel, K. et al. (2000). "Sensitive Assay of RNA Interference in Drosophila and Chinese Hamster Cultured Cells Using Firefly Luciferase Gene As Target," FEBS Letters 479:79-82.

Wells, J.A. et al. (1985). "Cassette Mutagenesis: An Efficient Method For Generation Of Multiple Mutations At Defined Sites," Gene 34(2-3):315-323.

Brinkmann, U. et al. (2017, e-pub. Jan. 10, 2017). "The Making Of Bispecific Antibodies," mABS 9(2):182-212.

Liu, H. et al. (Jan. 26, 2017). "Fc Engineering for Developing Therapeutic Bispecific Antibodies and Novel Scaffolds," Frontiers in Immunology 8(38):1-15.

Wang, B. et al. (2022, e-pub. Aug. 23, 2022). "A Novel IgG Fc By Computer-Aided Design Enhances Heavy-Chain Heterodimerization in Bi- or Trispecific Antibodies," Antibody Therapeutics 5(3):216-225.

Kunming, Z. et al. (Oct. 2018). "Progress in Research of Recombinant Bispecific Antibodies," International Journal of Biological Products 41(5):239-243. English Abstract.

* cited by examiner

CD20/CD3 BsAb Production Workflow

Transient transfection into expi 293 cells or CHO with certain ratio of H1:H2:Common LC First step purification with Pro.A beads Second step purification with MonoQ beads Analyzing elution fractions with T cell activation assay Analyzing purified protein with CE, DSF, DLS Conc. Of the related Frac.

| Frac # | conc. (ug/ml) |
|--------|---------------|
| 3 | 24 |
| 4 | 68 |
| 5 | 212 |
| 6 | 220 (peak) |
| 7 | 140 |
| 8 | 73 |
| 9 | 52 |
| 10 | 58 |
| 11 | 72 |
| 12 | 57 |

CD3 Fab

Fc

Her2 Fab

FIG. 16

HETEROMULTIMERIC PROTEINS AND METHODS OF USE THEREOF

CROSS-REFERENCE TO RELATED APPLICATIONS

This application is a national stage application under 35 U.S.C. § 371 of International Application No. PCT/US2020/025469, filed internationally on Mar. 27, 2020, which claims priority to U.S. Provisional Application No. 62/825,726, filed on Mar. 28, 2019, the contents of which are hereby incorporated by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 792702000200SEQLIST.TXT, date recorded: Sep. 22, 2021, size: 32,684 bytes).

FIELD OF THE INVENTION

The present application is related to heteromultimeric proteins, such as bispecific antibodies, compositions, methods of preparation and methods of use.

BACKGROUND OF THE INVENTION

The classical method of producing bispecific antibodies by co-expressing two different IgG molecules in hybrid hybridomas leads to up to 10 possible combinations of heavy and light chains. This compromises the yield and imposes a purification challenge. To overcome these challenges, a variety of bispecific antibody formats that promote heterodimer formation have been developed. Many known formats employ single chain variable region (scFv) modules, or similar structures that rely on engineered linkers to force the assembly of antigen binding components into the desired configuration. However, many of these bispecific antibody formats suffer from disadvantageous properties compared to natural antibodies, including tendency to aggregate, difficulties in production, short serum half-lives, and potential of immunogenicity.

Several bispecific antibody designs have been developed in the format of a native antibody, i.e., an antibody consisting of two light chains and two heavy chains. For example, the heavy chain Fc-Fc interface can be engineered with interacting amino acid pairs, such as knobs-into-holes (KIH) residues, cysteines that form disulfide bonds, or residues with opposite electrostatic charges, in order to actively promote the formation of heterodimers from distinct heavy chains when they are co-expressed. However, the classical KIH strategy still leads to significant homodimer formation and low yield of bispecific antibodies.

The disclosures of all publications, patents, patent applications and published patent applications referred to herein are hereby incorporated herein by reference in their entirety.

BRIEF SUMMARY OF THE INVENTION

The present application provides heteromultimeric proteins, such as Fc-containing heterodimeric proteins, multispecific antibodies and multispecific immunoadhesins, methods of preparation, and methods of use thereof.

One aspect of the present application provides a heteromultimeric (e.g., heterodimeric) protein comprising a first polypeptide comprising a first heavy chain constant domain 3 (CH3) domain and a second polypeptide comprising a second CH3 domain, wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, and wherein the amino acid residue numbering is based on EU numbering. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first CH3 domain and the second CH3 domain are human CH3 domains. In some embodiments, the first CH3 domain comprises a substitution selected from the group consisting of S354Y, S354F and S354W. In some embodiments, the first CH3 domain comprises S354Y. In some embodiments, the second CH3 domain does not comprise a compensatory substitution (e.g., a substitution at Y349) for the substitution of S354 in the first CH3 domain. In some embodiments, the second CH3 domain comprises a substitution selected from the group consisting of Q347E and Q347D. In some embodiments, the second CH3 domain comprises Q347E.

In some embodiments according to any one of the heteromultimeric proteins described above, the first CH3 domain and the second CH3 domain further comprise knob-into-hole (KIH) residues. In some embodiments, the knob-into-hole residues are T366Y and Y407T. In some embodiments, the first CH3 domain comprises T366Y and S354Y, and the second CH3 domain comprises Y407T and Q347E. In some embodiments, the first CH3 domain comprises Y407T and S354Y, and the second CH3 domain comprises T366Y and Q347E.

In some embodiments according to any one of the heteromultimeric proteins described above, the first polypeptide and/or the second polypeptide comprise a heavy chain constant domain 2 (CH2). In sonic embodiments, the heteromultimeric protein comprises an IgG Fc region. In some embodiments, the IgG Fc region is an IgG1, IgG2, IgG3, or IgG4 Fc region. In some embodiments, the first polypeptide is an antibody heavy chain, and/or the second polypeptide is an antibody heavy chain. In some embodiments, the heteromultimeric protein comprises one or more antibody light chains.

In some embodiments according to any one of the heteromultimeric proteins described above, the heteromultimeric protein is a multispecific (e.g., bispecific) antibody.

In some embodiments according to any one of the heteromultimeric proteins described above, the heteromultimeric protein comprises: (a) a first heavy chain comprising from the N-terminus to the C-terminus: a first heavy chain variable domain (VH1), a first heavy chain constant domain 1 (CH1), a first heavy chain constant domain 2 (CH2), and the first CH3 domain; (b) a first light chain comprising from the N-terminus to the C-terminus: a first light chain variable domain (VL1), and a first light chain constant domain (CL); (c) a second heavy chain comprising from the N-terminus to the C-terminus: a second heavy chain variable domain (VH2); a second CH1; a second CH2, and the second CH3 domain; and (d) a second light chain comprising from the N-terminus to the C-terminus: a second light chain variable domain (VL2), and a second CL; wherein VH1 and VL1 associate to form a first antigen binding site that specifically binds to a first target, and VH2 and VL2 associate to form a second antigen binding site that specifically binds to a second target. In some embodiments, VL1 and VL2 have the same amino acid sequence. In some embodiments, VL1 and VL2 have different amino acid sequences. In some embodiments, the first target and the second target are the same epitopes. In some embodiments, the first target and the second target are different epitopes of the same antigen. In some embodiments, the first target and the second target are different antigens. In some embodiments, the first antigen binding site specifically binds a tumor antigen and the second antigen binding site specifically binds CD3, or the first antigen binding site specifically binds CD3 and the second antigen binding site specifically binds a tumor antigen. In some embodiments, the first antigen binding site specifically binds CD20 and the second antigen binding site specifically binds CD3, or the first antigen binding site specifically binds CD3 and the second antigen binding site specifically binds CD20. In some embodiments, the first antigen binding site specifically binds HER2 and the second antigen binding site specifically binds CD3, or the first antigen binding site specifically binds CD3 and the second antigen binding site specifically binds HER2. In some embodiments, the heteromultimeric protein comprises: (a) a first heavy chain comprising from the N-terminus to the C-terminus: a third heavy chain variable domain (VH3), a third CH1, the VH1, the first CH1, the first CH2, and the first CH3 domain; (b) a first light chain comprising from the N-terminus to the C-terminus: a third light chain variable domain (VL2), a third CL, the VL1, and the first CL; wherein VH3 and VL3 associate to form a third antigen binding site that specifically binds to a third target. In some embodiments, the first antigen binding site and the third antigen binding site specifically bind to the same antigen. In some embodiments, the first antigen binding site and the third antigen binding site specifically bind to HER2 and the second antigen binding site specifically bind to CD3.

In some embodiments according to any one of the heteromultimeric proteins described above, the heteromultimeric protein comprises: (a) a first heavy chain comprising from the N-terminus to the C-terminus: a first VHH, a first heavy chain constant domain 2 (CH2), and the first CH3 domain; (h) a second heavy chain comprising from the N-terminus to the C-terminus: a first heavy chain variable domain (VH1), a second CH1, a second CH2, and the second CH3 domain; and (d) a light chain comprising from the N-terminus to the C-terminus: a first light chain variable domain (VL1), and a first CL; wherein VH1 and VL1 associate to form a first antigen binding site that specifically binds to a first target, and the first VHH specifically binds to a second target. In some embodiments, the first antigen binding site specifically binds to CD3 and the first VHH specifically binds to a tumor antigen, or the first antigen binding site specifically binds to a tumor antigen and the first VHH specifically binds to CD3. In some embodiments, the first VHH specifically binds to BCMA. In some embodiments, the first heavy chain comprises from the N-terminus to the C-terminus: a second VHH, the first VHH, the first CH2, and the first CH3 domain, wherein the second VHH specifically binds to a third target. In some embodiments, the first VHH and the second VHH specifically bind to the same antigen. In some embodiments, the first VHH and the second VHH specifically bind to BCMA.

In some embodiments according to any one of the heteromultimeric proteins described above, the heteromultimeric protein is an immunoadhesin or an antibody-immunoadhesin chimera.

Another aspect of the present application provides a polypeptide comprising an antibody CH3 domain, wherein the CH3 domain comprises a substitution relative to a wildtype CH3 domain at amino acid position 354 with a bulky hydrophobic amino acid and/or a substitution relative to a wild type CH3 domain at amino acid position 347 with a negatively charged amino acid, and wherein the polypeptide has decreased ability to form homodimers compared to a polypeptide comprising a wildtype CH3 domain. In some embodiments, the CH3 domain a human CH3 domain. In some embodiments, the CH3 domain comprises a substitution selected from the group consisting of S354Y, S354F and S354W. In some embodiments, the CH3 domain comprises S354Y. In some embodiments, the CH3 domain comprises a substitution selected from the group consisting of Q347E and Q347D. In some embodiments, the CH3 domain comprises Q347E. In some embodiments, the CH3 domain further comprises a knob-into-hole residue, such as T366Y or S407T. In some embodiments, the polypeptide further comprises a heavy chain constant domain 2 (CH2). In some embodiments, the polypeptide comprises an antibody heavy chain.

In some embodiments, there is provided a polypeptide comprising the CH3 domain of any one of SEQ ID NOs: 1-4. In some embodiments, there is provided a polypeptide comprising the amino acid sequence of any one of SEQ ID NOs: 1-4.

In some embodiments, there is provided an antibody (e.g., bispecific antibody) comprising the polypeptide according to any one of the polypeptides described above.

Another aspect of the present application provides a method of generating a heteromultimeric protein that specifically binds to a first target and a second target, comprising: (a) providing a first polypeptide comprising a first binding domain that specifically binds to the first target and a first CH3 domain; and (b) providing a second polypeptide comprising a second binding domain that specifically binds to the second target and a second CH3 domain; wherein: (i) the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid; or (ii) the first CH3 domain comprises a substitution relative to a wildtype CH3 domain at amino acid position 347 with a negatively charged amino acid, and/or the second CH3 domain comprises a substitution relative to a wildtype CH3 domain at amino acid position 354 with a bulky hydrophobic amino acid; and wherein the amino acid residue numbering is based on EU numbering. In some embodiments, the bulky hydrophobic amino acid at amino acid position 354 in one CH3 domain forms a hydrophobic interaction with an amino acid residue in the other CH3 domain. In some embodiments, the other CH3 domain comprises a bulky hydrophobic residue at amino acid position 349 (e.g., Y349). In some embodiments, the negatively charged amino acid at amino acid position 347 in one CH3 domain forms an ionic bond with an amino acid residue in the other CH3 domain. In some embodiments, the other CH3 domain comprises a positively charged residue at amino acid position 360 (e.g., K360). In some embodiments, the first CHS domain and the second CH3 domain are human CH3 domains. In some embodiments, the first or second CH3 domain comprises a substitution selected from the group consisting of S354Y, S354F and S354W. In some embodiments, the first or second CH3 domain comprises S354Y. In some embodiments, the first or second. CH3 domain comprises a substitution selected from the group consisting of Q347E and Q347D. In some embodiments, the first or second CH3 domain comprises Q347E. In some embodiments, the first CH3 domain and the second CH3 domain further comprise KIH residues, such as T366Y and Y407T, In some embodiments, the first CH3 domain comprises T366Y and S354Y, and the second CH3 domain comprises Y407T and Q347E. In some embodiments, the first CH3 domain comprises Y407T and S354Y, and the second CH3 domain comprises T366Y and Q347E.

In some embodiments, there is provided a heteromultimeric protein prepared using any one of the methods described above.

One aspect of the present application provides one or more nucleic acid(s) encoding the heteromultimeric protein according to any one of the heteromultimeric proteins described above or the polypeptides according to any one of the polypeptides described above. In some embodiments, there is provided a vector comprising the one or more nucleic acid(s) according to any one of the nucleic acids described above. In some embodiments, there is provided a host cell comprising the one or more nucleic acid(s) according to any one of the nucleic acids described above or the vector according to any one of the vectors described above.

One aspect of the present application provides a method for preparing a multispecific (e.g., bispecific) antibody or a heteromultimeric (e.g., heterodimeric) protein, comprising: (a) culturing the host cell according to any one of the host cells described above under conditions that allow expression of the one or more nucleic acid(s) or vector; and (b) recovering the multispecific antibody or the heteromultimeric protein from the host cell culture.

Another aspect of the present application provides a pharmaceutical composition comprising the heteromultimeric protein according to any one of the heteromultimeric proteins described above or the antibody according to any one of the antibodies described above, and a pharmaceutically acceptable excipient. In some embodiments, there is provided a method for treating a subject in need thereof, comprising administering to the subject an effective amount of the pharmaceutical composition according to any one of the pharmaceutical compositions described above.

Also provided are kits and articles of manufacture comprising any one of the heteromultimeric proteins (e.g., bispecific antibodies) described above or useful for any one of methods described above.

9. Lanes 1-8 show fractions of the main peak labeled A1-A8, lanes 9 and 10 show the 2nd and 3rd fractions of the small peak labelled A14 and B7, and lane 11 shows Her2-B3/CD3 bispecific antibody after Protein A purification. Lane M shows a ladder of protein markers, and the masses in kilodaltons (KD) of the protein markers are shown on the right.

Figure 11:
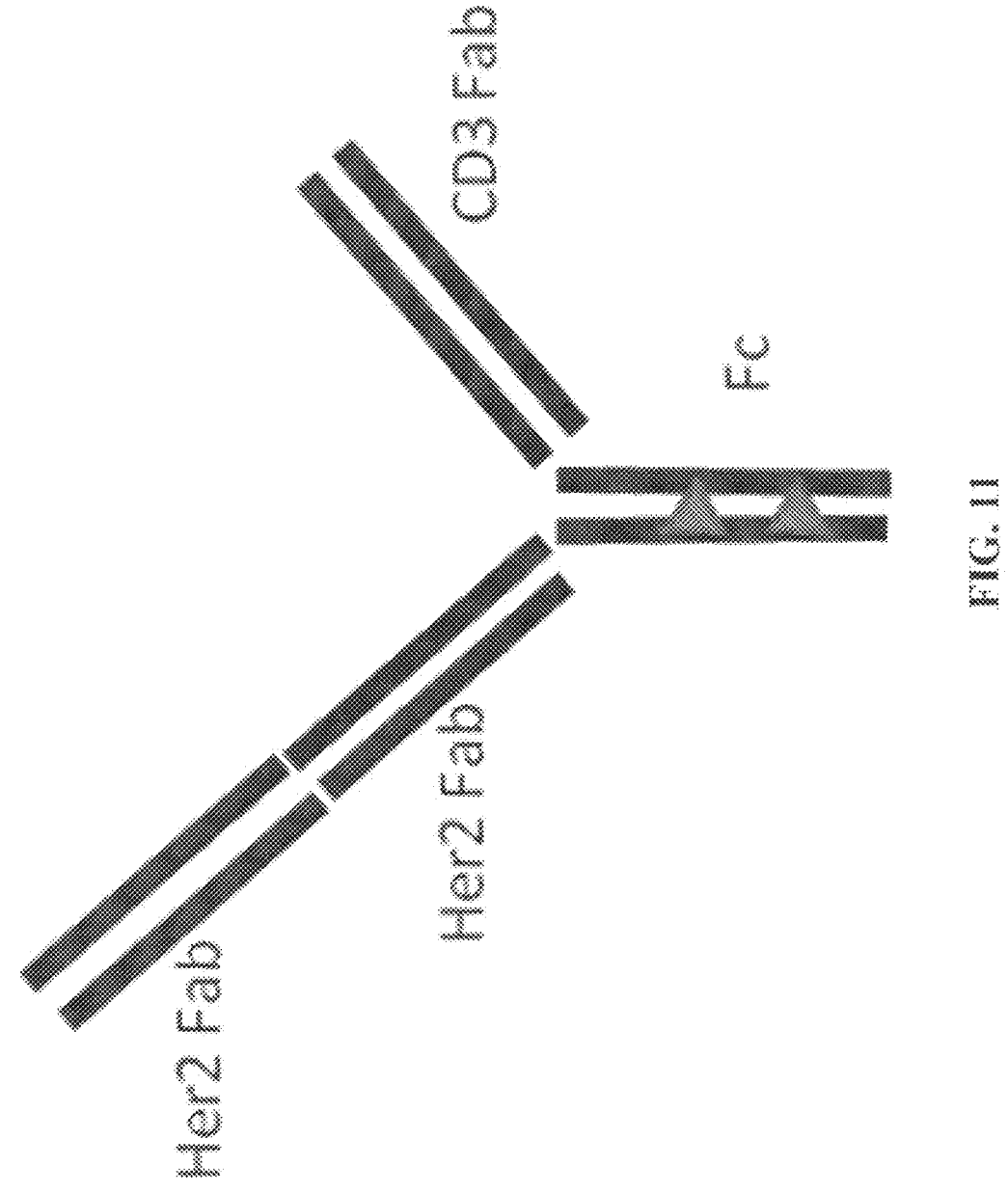

FIG. 11 shows a schematic diagram of the Her2-B3-V3/CD3 bispecific antibody, comprising two anti-Her2 Fabs, one anti-CD3 Fab, and one Fc domain.

Figure 12:
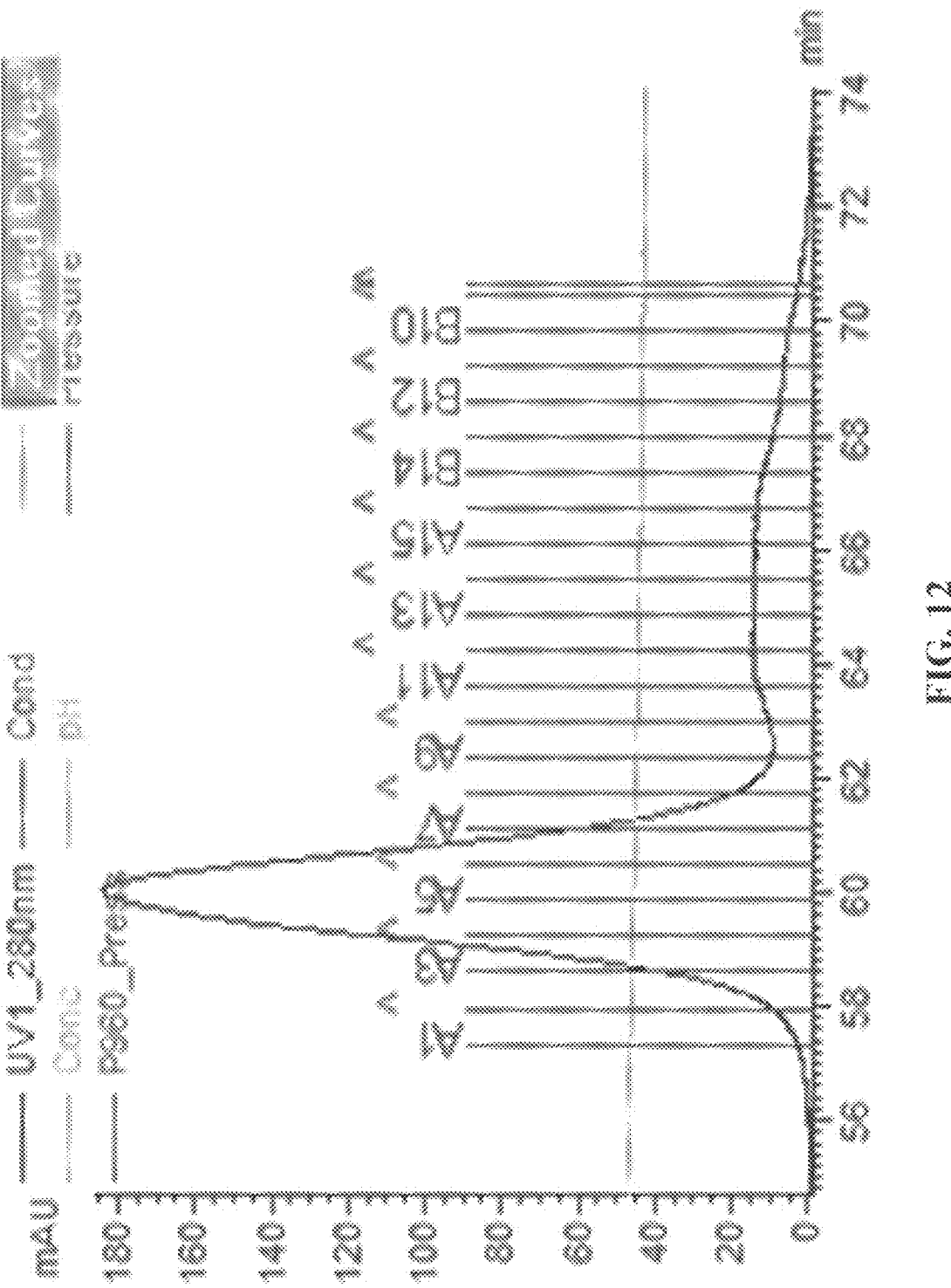

FIG. 12 shows CEX purification of Her2-B3-V3/CD3 bispecific antibody. Samples were previously purified on a Protein A column. Retention time is shown on the x-axis in minutes, and relative protein abundance is shown on the y-axis in milli absorbance units (mAU). Individual peak fractions are labeled.

Figure 13:
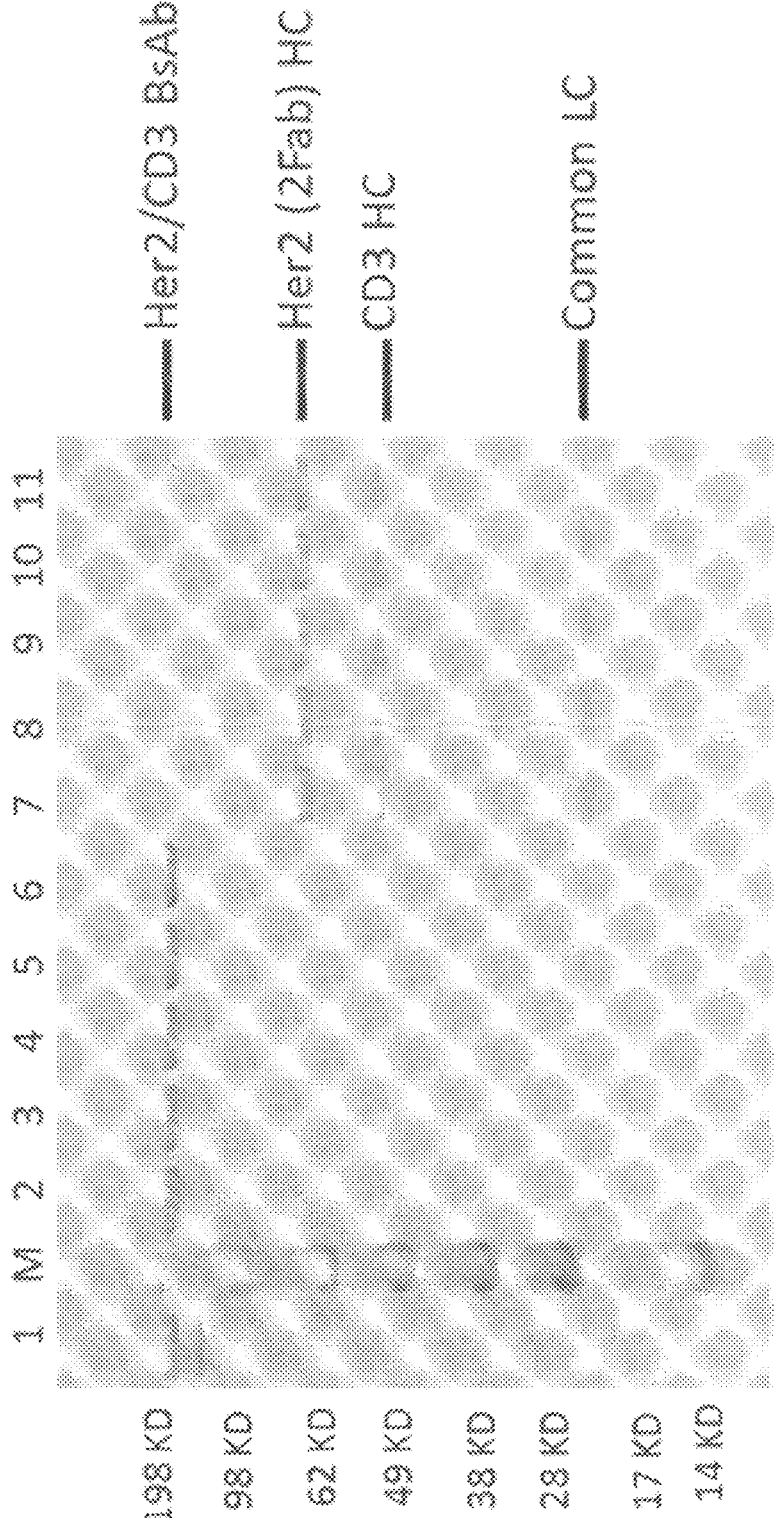

FIG. 13 shows SDS-PAGE of fractions of Her2-B3-V3/CD3 bispecific antibody after CEX purification. Lane 1 shows Her2-B3-V3/CD3 expressed in supernatant. Lanes 2-6 show the purified fractions A3-A7 (see FIG. 12), non-reduced. Lanes 7-11 show the purified fraction A3-A7 (see FIG. 12), reduced. Lane M shows a ladder of protein markers, and the masses in kilodaltons (KD) of the protein markers are shown on the left. The position of the assembled Her2/CD3 bispecific antibody ("Her2/CD3 BsAb"), and the individual components (i.e., the anti-Her2 heavy chain with two Fabs "Her2 (2Fab) HC", the anti-CD3 heavy chain "CD3 FIC", and the light chain "Common LC") are indicated on the right.

Figure 14:
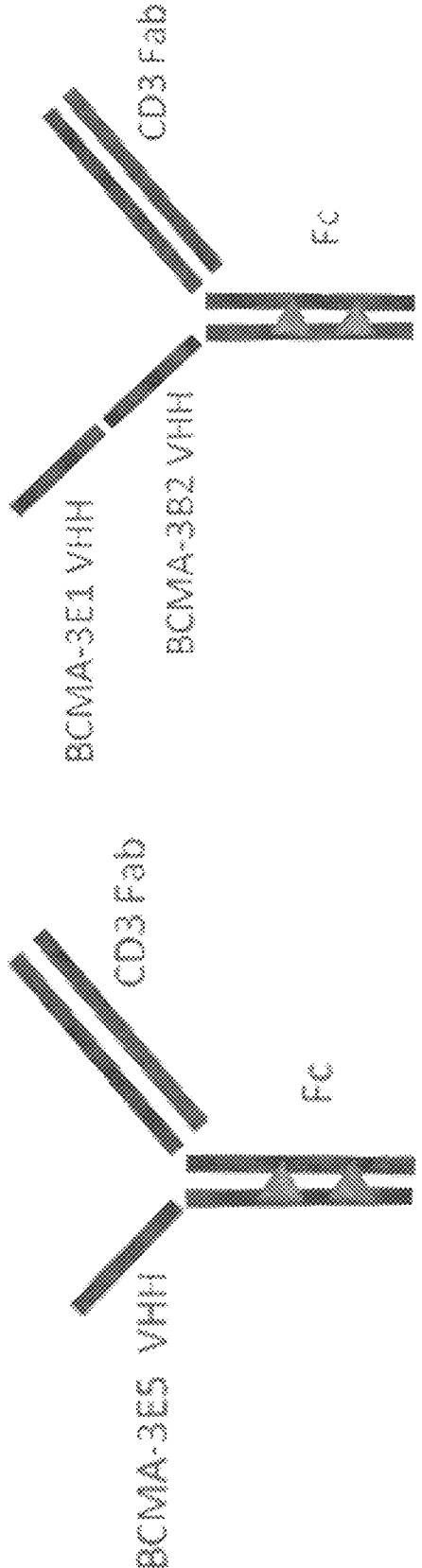

FIG. 14 shows schematic diagrams of BCMA-Fc/CD3 bispecific antibodies. At left is BCMA-3E5/CD3, which comprises one BCMA-3E5 VHH domain, one CD3 Fab and one Fc domain. At right one is BCMA-3E1B2/CD3, which comprises two BCMA VHH domains (3E1 and 3B2), one CD3 Fab and one Fc domain.

Figure 15:
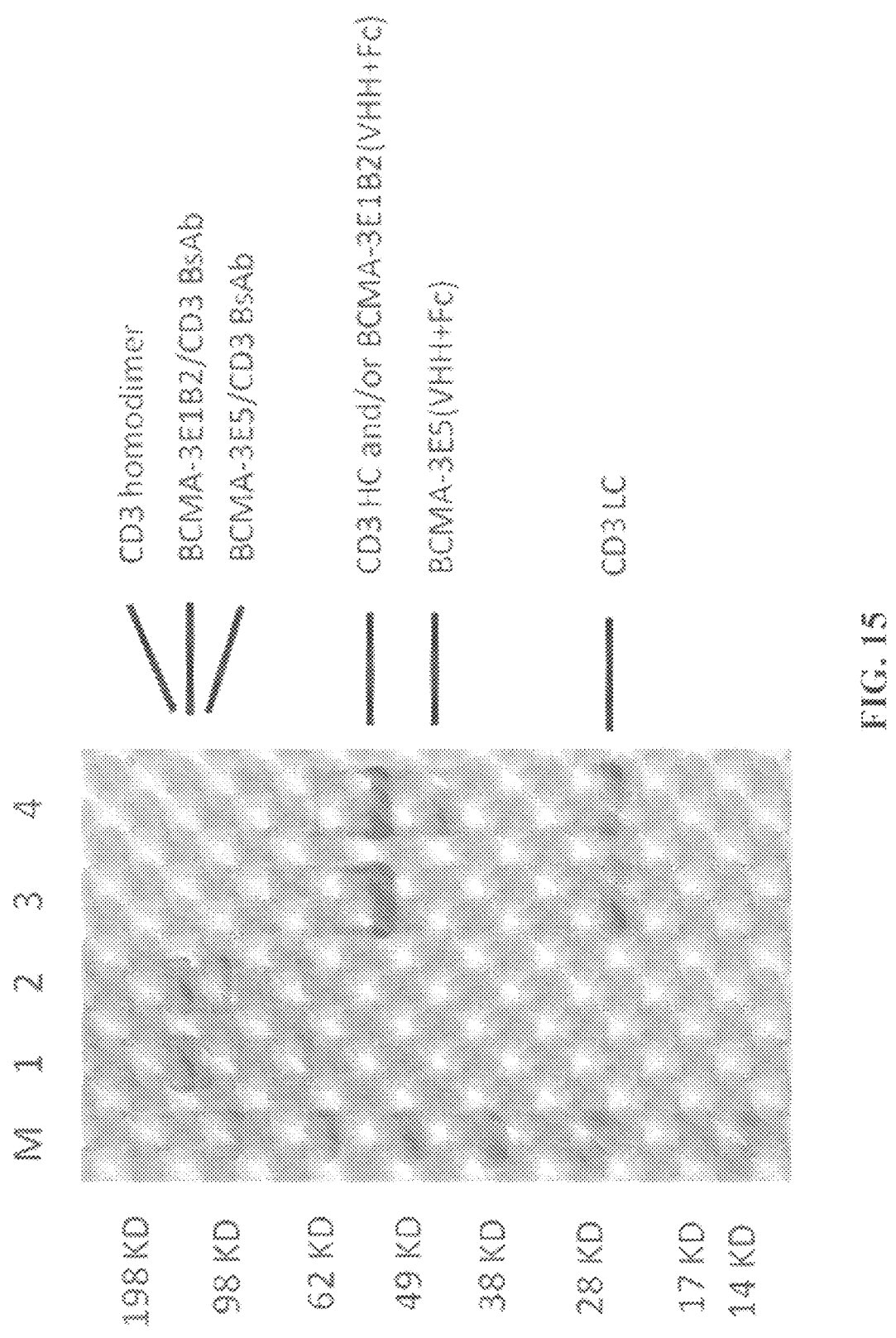

FIG. 15 shows SDS-PAGE of Protein A-purified BCMA-3E1B2/CD3 and BCMA-3E5/CD3. Lane 1 shows BCMA-3E1B2/CD3, non-reduced, lane 2 shows BCMA-3E5/CD3, non-reduced, lane 3 shows BCMA-3E1 B2/CD3, reduced, and lane 4 shows BCMA-3E5/CD3, reduced. Lane M shows a ladder of protein markers, and the masses in kilodaltons (KD) of the protein markers are shown on the left. The positions of the components of BCMA-Fc/CD3 bispecific antibodies are indicated at right.

Figure 16:
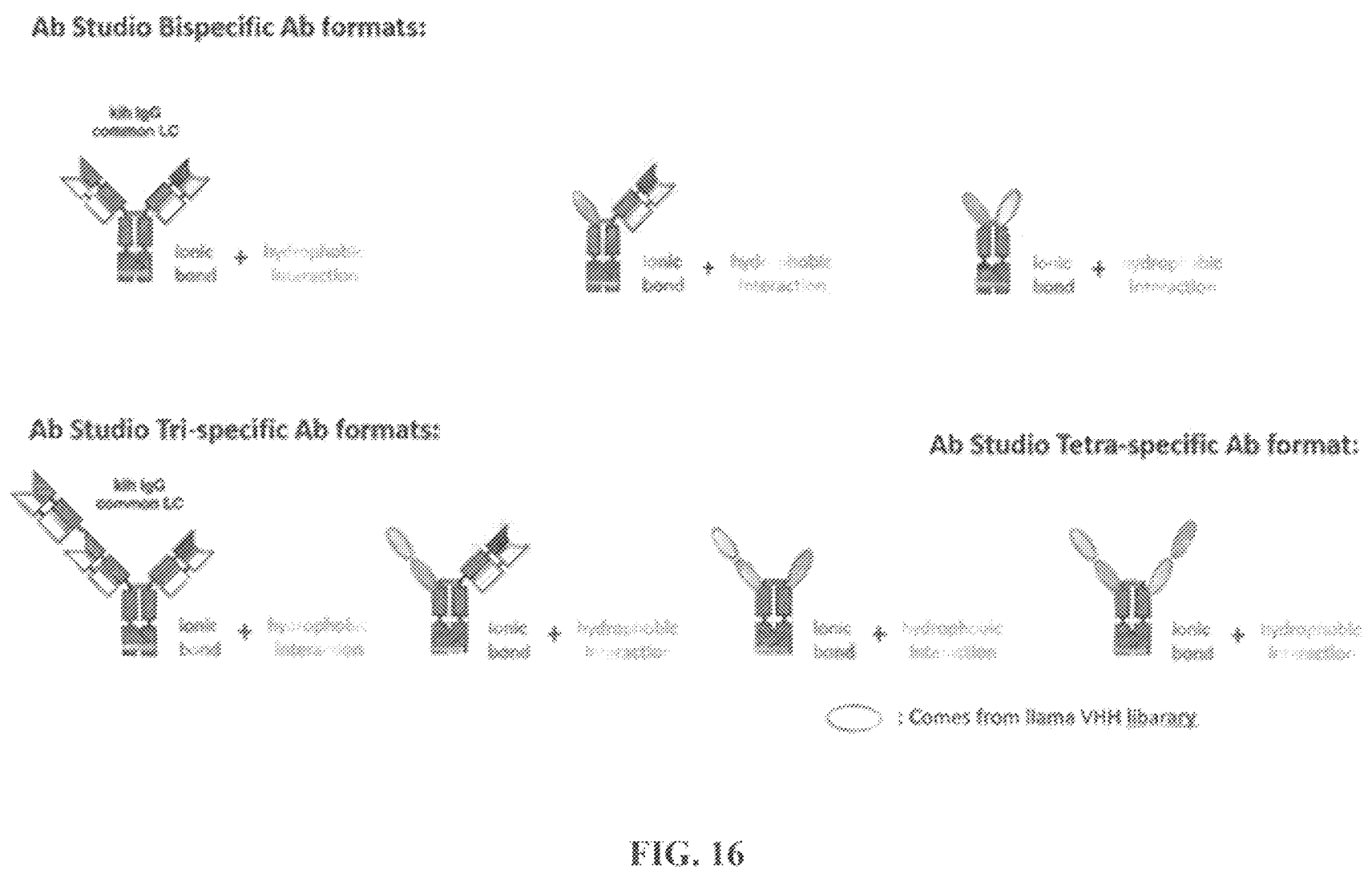

FIG. 16 shows schematic structures of multispecific antibody constructs with engineered ionic bond and hydrophobic interactions in the Fc region. Bispecific antibody formats are shown on the top row, and tri- and tetra-specific antibody formats are shown on the bottom row. As indicated, oval shaped structures are obtained from a llama VHH library.

DETAILED DESCRIPTION OF THE INVENTION

The present application provides heteromultimeric (e.g., heterodimeric) proteins comprising antibody heavy chain constant domain 3 (CH3) domains with novel engineered ionic bond and/or hydrophobic interaction, which can be combined with knobs-into-holes (KIH) residues, to promote heterodimer formation. Methods of preparing and using the heteromultimeric proteins are further provided. The methods of preparation described herein are useful in enhancing heterodimer formation and hindering homodimer formation when two different CH3-containing polypeptides are co-expressed. The CH3-based heteromultimeric protein strategies described herein are applicable to all Fc-containing heteromultimeric proteins, such as bispecific antibodies and bispecific immunoadhesins.

Accordingly, one aspect of the present application provides a heteromultimeric protein comprising a first polypeptide comprising a first CH3 domain and a second polypeptide comprising a second CH3 domain, wherein the first CH3 domain comprises a substitution relative to a wildtype CH3 domain at amino acid position 354 with a bulky hydrophobic amino acid (e.g., S354Y), and/or the second CH3 domain comprises a substitution relative to a wildtype CH3 domain at amino acid position 347 with a negatively charged amino acid (e.g., Q347E), and wherein the amino acid residue numbering is based on EU numbering.

Also provided are compositions (such as pharmaceutical compositions), methods of preparation, methods of treatment, kits and articles of manufacture.

I. Definitions

As used herein, "heteromultimer" or "heteromultimeric protein" is a molecule comprising at least a first polypeptide and a second polypeptide, wherein the second polypeptide differs in amino acid sequence from the first polypeptide by at least one amino acid residue. In some embodiments, the heteromultimer has binding specificity for at least two different ligands or binding sites. The heteromultimer can comprise a "heterodimer" formed by the first and second polypeptide or can form higher order tertiary structures where polypeptides in addition to the first and second polypeptide are present.

As used herein, a "binding domain" comprises any region of a polypeptide, which is responsible for specifically binding to a molecule of interest (e.g., an antigen, ligand, receptor, substrate or inhibitor). Exemplary binding domains include an antibody variable domain, receptor binding domain, ligand-binding domain and an enzymatic domain.

As use herein, the term "specifically binds," "specifically recognizing," or "is specific for" refers to measurable and reproducible interactions, such as binding between a target and an antibody, that are determinative of the presence of the target in the presence of a heterogeneous population of molecules, including biological molecules. For example, an antibody that specifically recognizes a target (which can be an epitope) is an antibody that binds this target with greater affinity, avidity, more readily, and/or with greater duration than its bindings to other targets. In some embodiments, an antibody that specifically recognizes an antigen reacts with one or more antigenic determinants of the antigen with a binding affinity that is at least about 10 times its binding affinity for other targets.

The term "antibody" herein is used in the broadest sense and includes fill-length antibodies and antigen-binding fragments thereof. The term "antibody" includes monoclonal antibodies (including full-length 4-chain antibodies or full-length heavy-chain only antibodies which have an immunoglobulin Fc region), antibody compositions with poly-epitopic specificity, multispecific antibodies (e.g., bispecific antibodies, diabodies, and single-chain molecules), as well as antibody fragments (e.g., Fab, F(ab')₂, and Fv). Antibodies contemplated herein include single-domain antibodies, such as heavy chain only antibodies.

A full-length four-chain antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain). IgG4 (γ4 heavy chain), IgA1 (α1 heavy chain), or IgA2 (a2 heavy chain).

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the *Camelid* species have a single heavy chain variable region, which is referred to as "VHH", is thus a special type of $V_H$.

The term "heavy chain-only antibody" or "HCAb" refers to a functional antibody, which comprises heavy chains, but lacks the light chains usually found in 4-chain antibodies. *Camelid* animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from *camelid* HCAbs, and their heavy chain variable domains are referred herein as "VHHs" (Variable domain of the heavy chain of the Heavy chain antibody). *Camelid* sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a single-domain antibody (such as $V_H$H), and a multispecific antibody formed from a portion of an antibody comprising one or more CDRs, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies. Papain digestion of antibodies produced two identical antigen-binding fragments, called "Fab" fragments, and a residual "Fc" fragment, a designation reflecting the ability to crystallize readily. The Fab fragment consists of an entire L chain along with the variable domain of the H chain ($V_H$), and the first constant domain of one heavy chain ($C_H$1). Each Fab fragment is monovalent with respect to antigen binding, it has a single antigen-binding site, Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy-terminus of the $C_H$1 domain including one or more cysteines from the antibody hinge region. Fab'-SH is the designation herein for Fab' in which the steine residue(s) of the constant domains bear a free thiol group. F(ab')$_2$ antibody fragments originally were produced as pairs of Fab' fragments which have hinge cysteines between them. Other chemical couplings of antibody fragments are also known.

The term "constant domain" refers to the portion of an immunoglobulin molecule having a more conserved amino acid sequence relative to the other portion of the immunoglobulin, the variable domain, which contains the antigen-binding site. The constant domain contains the $C_H$1, $C_H$2 and $C_H$3 domains (collectively, $C_H$) of the heavy chain and the CHL (or $C_L$) domain of the light chain.

The "light chains" of antibodies (immunoglobulins) from any mammalian species can be assigned to one of two clearly distinct types, called kappa ("κ") and lambda ("λ"), based on the amino acid sequences of their constant domains.

"Fv" is the minimum antibody fragment, which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the scFv polypeptide further comprises a polypeptide linker between the $V_H$ and $V_L$ domains, which enables the scFv to form the desired structure for antigen binding. For a review of the scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The term "specificity" refers to selective recognition of an antigen binding protein for a particular epitope of an antigen. Natural antibodies, for example, are monospecific. The term "multispecific" as used herein denotes that an antigen binding protein has polyepitopic specificity (i.e., having two, three, or more antigen binding sites is capable of specifically binding to two, three, or more, different epitopes on one biological molecule or is capable of specifically binding to epitopes on two, three, or more, different biological molecules). "Bispecific" as used herein denotes that an antigen binding protein has two different antigen-binding specificities. Unless otherwise indicated, the order in which the antigens bound by a bispecific antibody listed is arbitrary.

The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct Biol.* 2:593-596 (1992).

A "multispecific antibody" is a molecule having binding specificities for at least two different antigens or epitopes. "Multispecific antibody" encompasses bispecific antibodies ("BsAbs") that bind to two different antigens or epitopes, and antibodies with more than two specificities such as trispecific antibodies.

As used herein, the term "immunoadhesin" refers to antibody-like molecules, which combine the binding domain of a heterologous protein ("adhesion", e.g., a receptor, ligand or enzyme) with the effector functions of immunoglobulin constant domains. Structurally, the immunoadhesins comprise a fusion of the adhesin amino acid sequence with the desired binding specificity which is other than the antigen binding site of an antibody and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

As used herein the phrase "multispecific immunoadhesin" designates immunoadhesins having at least two binding specificities (i.e., combining two or more adhesin binding domains). Multispecific immunoadhesins can be assembled as heterodimers, heterotrimers or heterotetramers, e.g., as disclosed in WO 89/02922, EP314,317, and U.S. Pat. No. 5,116,964. In some embodiments, the multispecific immunoadhesin is bispecific.

An "antibody-immunoadhesin chimera" comprises a molecule, which combines at least one binding domain of an antibody with at least one immunoadhesin.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

The term "knob-into-hole" or "KIH" refers to a pair of engineered amino acid residues in CH3 domains, which results in a steric modification of the contact surface of the first CH3 domain that is preferentially attached to the respective contact surface of the second CH3 domain through the complementary steric modification. Such steric modifications mainly result from the different amino acid residues and side chains, e.g., to produce a "knob" or "hole" structure, which are complementary to form a "knob-into-hole" dimer. See, for example, See, for example, Ridgway, J. B., L. G. Presta, et al. (1996). "'Knobs-into-holes' engineering of antibody CH3 domains for heavy chain heterodimerization." Protein Eng 9(7): 617-21; Atwell, S., J. B. Ridgway, et al. (1997). "Stable heterodimers from remodeling the domain interface of a homodimer using a phage display library." J Mol Biol 270(1): 26-35; Merchant, A. M., Z. Zhu, et al. (1998). "An efficient route to human bispecific IgG." Nat Biotechnol 16(7): 677-81; Carter, P. (2001). "Bispecific human IgG by design." J Immunol Methods 248(1-2): 7-15; and U.S. Pat. Nos. 5,731,168 and 7,183,076, which are incorporated herein by reference.

"Isolated" heteromultimer means heteromultimer, which has been identified and separated and/or recovered from a component of its natural cell culture environment. Contaminant components of its natural environment are materials, which would interfere with diagnostic or therapeutic uses for the heteromultimer, and may include enzymes, hormones, and other proteinaceous or nonproteinaceous solutes. The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homomultimers). Expressed in terms of purity, substantial homogeneity means that the amount of by-products does not exceed about 10%, 5%, 1%, 0.5% or less, wherein the percentages are by weight.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. The methods of the invention contemplate any one or more of these aspects of treatment.

An "effective amount" of an antibody or composition as disclosed herein, is an amount sufficient to carry out a specifically stated purpose. An "effective amount" can be determined empirically and by known methods relating to the stated purpose.

As used herein, by "pharmaceutically acceptable" or "pharmacologically compatible" is meant a material that is not biologically or otherwise undesirable, material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

It is understood that embodiments of the invention described herein include "consisting" and/or "consisting essentially of" embodiments.

Reference to "about" a value or parameter herein includes and describes) variations that are directed to that value or parameter per se. For example, description referring to "about X" includes description of "X".

As used herein, reference to "not" a value or parameter generally means and describes "other than" a value or parameter.

As used herein and in the appended claims, the singular forms "a," "an," "the" include plural referents unless the context clearly dictates otherwise.

II. Heteromultimeric Proteins

Figure 1:
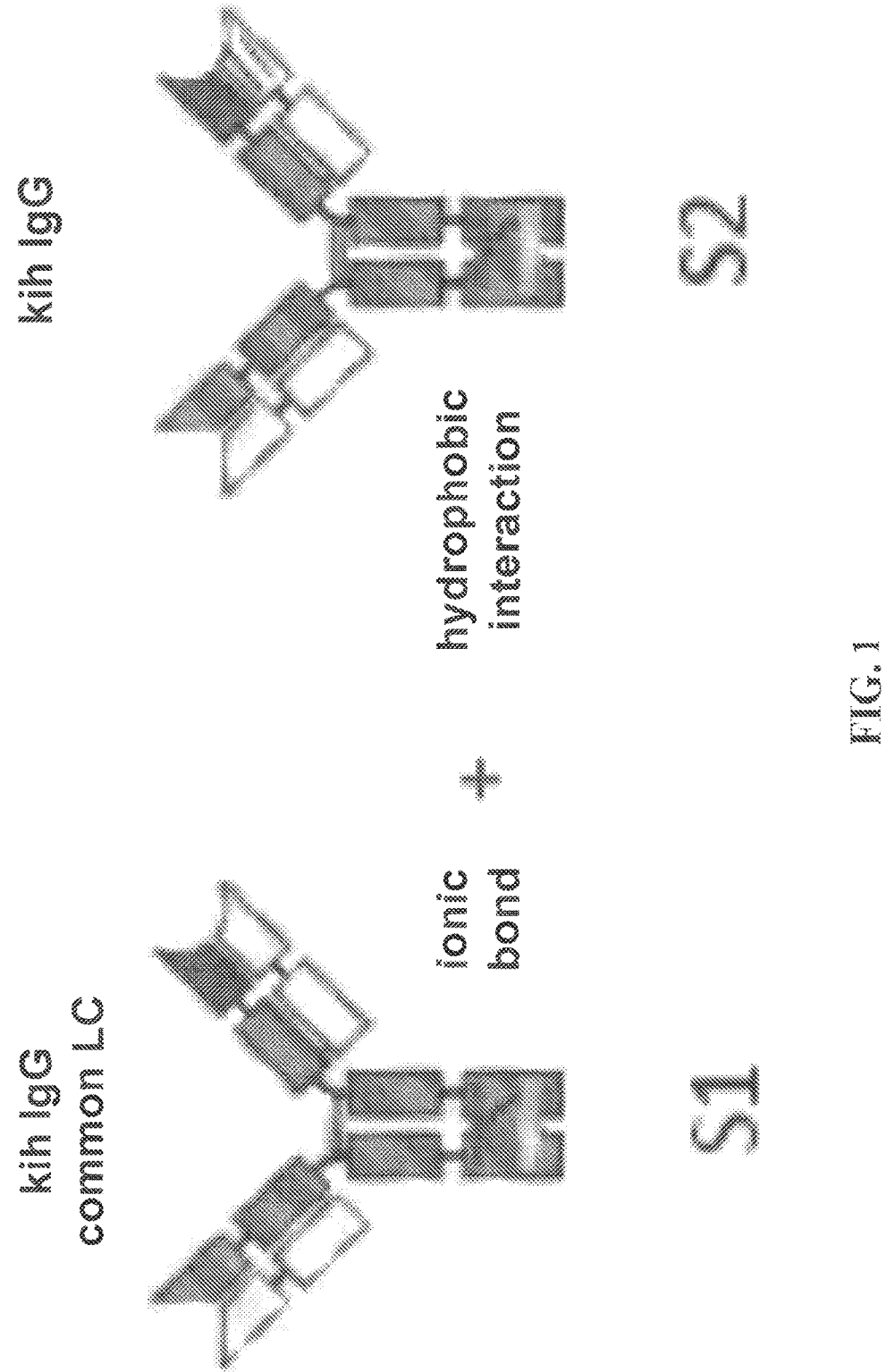
FIG. 1 shows schematic structures of two bispecific antibody constructs. In some embodiments, a first heavy chain of the bispecific antibody constructs has an engineered residue, such as Q347E, that forms an ionic bond with a native residue (e.g., K360) in the second heavy chain; and the second heavy chain has an engineered residue, such as S354Y, that forms hydrophobic interactions with a native residue (e.g., Y349) in the first heavy chain. The construct on the left (S1) has a common light chain, and the construct on the right (S2) has two different light chains. The engineered ionic bond and hydrophobic interaction described herein may be combined with traditional knob-into-hole (KIH) mutations to promote heterodimer formation.
Figure 2A:
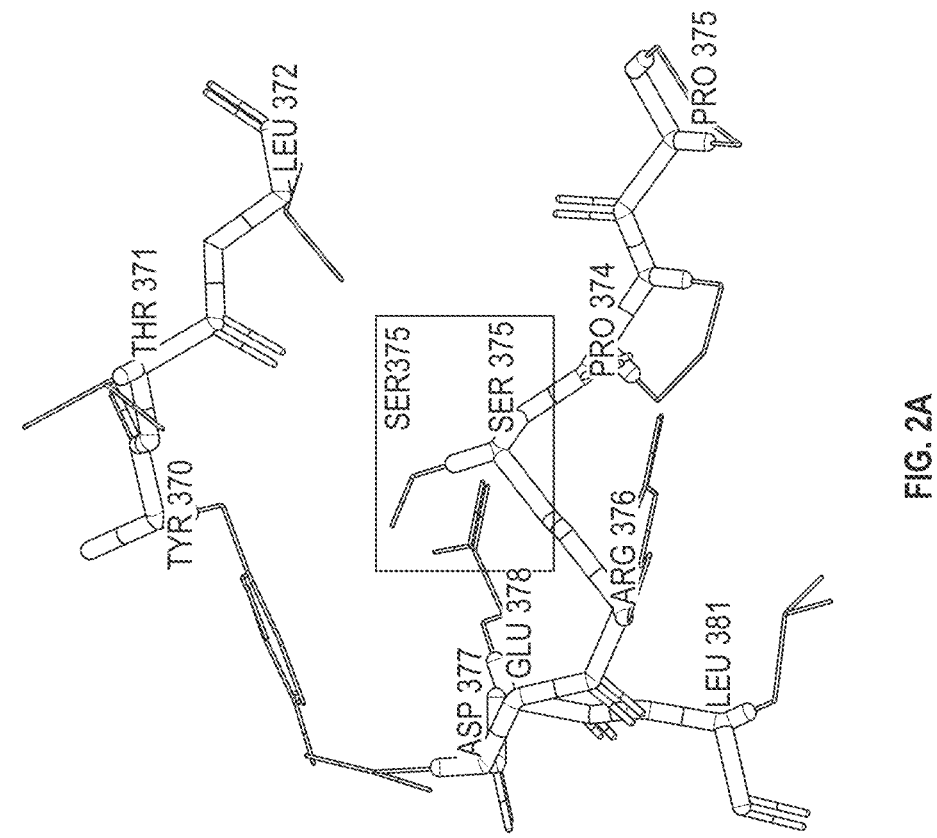
FIG. 2A shows a partial view of a crystal structure of the CH3-CH3 interface of two heavy chains in an antibody. S354 (i.e., S375 in the figure according to Kabat numbering) in the first heavy chain does not form any contact with residues in the second heavy chain.
Figure 2B:
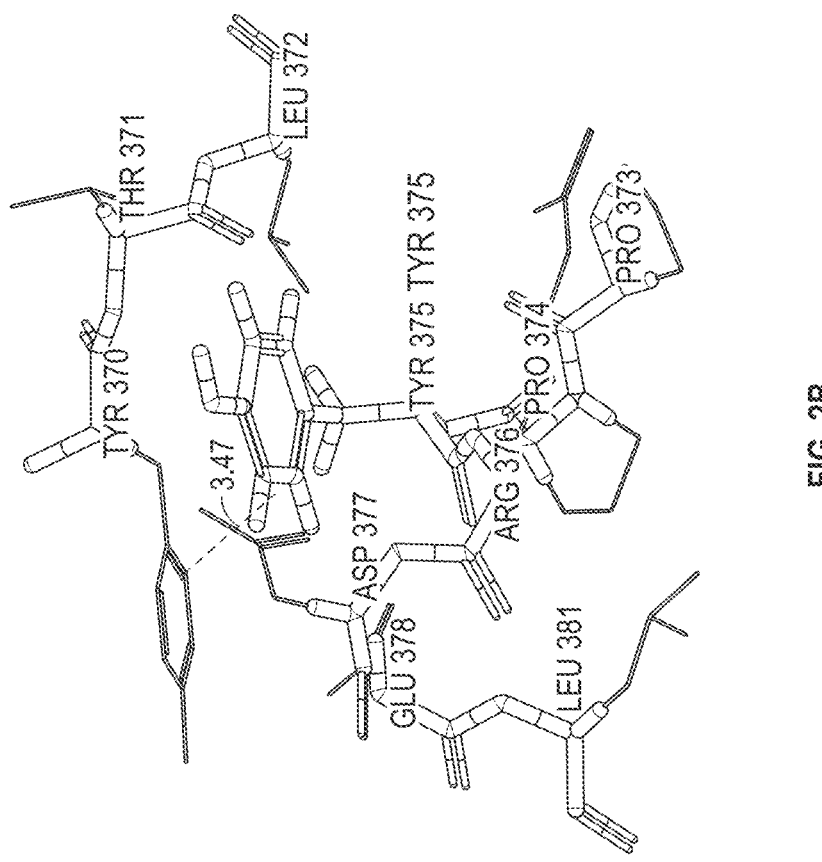
FIG. 2B shows a partial view of a modeled crystal structure of the CH3-CH3 interface of a heterodimeric Fc having a S354Y mutation (i.e., Y375 in the figure according to Kabat numbering) in a first heavy chain. S354Y forms hydrophobic interaction with Y349 (i.e., Y370 in the figure according to Kabat numbering) in the second heavy chain.
Figure 2C:
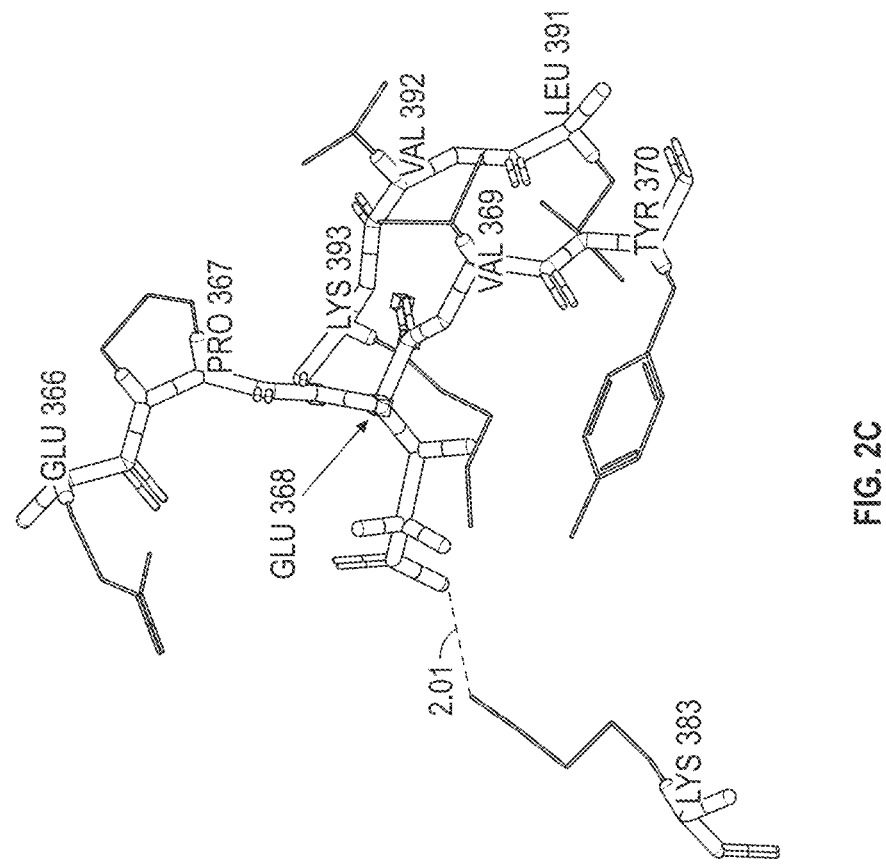
FIG. 2C shows a partial view of a modeled crystal structure of the CH3-CH3 interface of a heterodimeric Fc having a Q347E mutation (i.e., E368 in the figure according to Kabat numbering) in a first heavy chain. Q347E forms an ionic bond with K360 (i.e., K383 in the figure according to Kabat numbering) in the second heavy chain. Q347 may or may not form a very weak hydrogen bond with K360.

The present application provides heteromultimeric proteins, such as heterodimeric proteins, comprising a first polypeptide comprising a first antibody heavy chain constant domain 3 (CH3) domain and a second polypeptide comprising a second CH3 domain, wherein the first CH3 domain and second CH3 domain comprise engineered hydrophobic interaction and electrostatic interaction. In some embodiments, the first CH3 domain and the second CH3 domain further comprise knob-into-hole ("KIH") residues. Exemplary structures for the heteromultimeric proteins include heterodimers (e.g., bispecific immunoadhesin), heterotrimers (e.g., antibody-immunoadhesin chimera), heterotetramers (e.g., bispecific antibody) and further oligomeric structures. In some embodiments, the heteromultimeric protein is a bispecific antibody, such as a common light chain antibody or an antibody having two different light chains. See, e.g., FIG. 1.

In some embodiments, there is provided a heteromultimeric protein (e.g., heterodimeric protein) comprising a first polypeptide comprising a first CH3 domain and a second polypeptide comprising a second. CH3 domain, wherein the first CH3 domain comprises an engineered amino acid residue that forms hydrophobic interaction with a native amino acid residue of the second CH3 domain, and the second CH3 domain comprises an engineered amino acid residue that forms an ionic bond with a native amino acid residue in the first CH3 domain. In some embodiments, there is provided a heteromultimeric protein (e.g., heterodimeric protein) comprising a first polypeptide comprising a first CH3 domain and a second polypeptide comprising a second CH3 domain, wherein the first CH3 domain comprises a first engineered amino acid residue that forms hydrophobic interaction with a first native amino acid residue of the second CH3 domain, and a second engineered amino acid residue that forms an ionic bond with a second native amino acid residue in the second CH3 domain. In some embodiments, the first CH3 domain and the second CH3 domain further comprise KIH residues.

Figure 7:
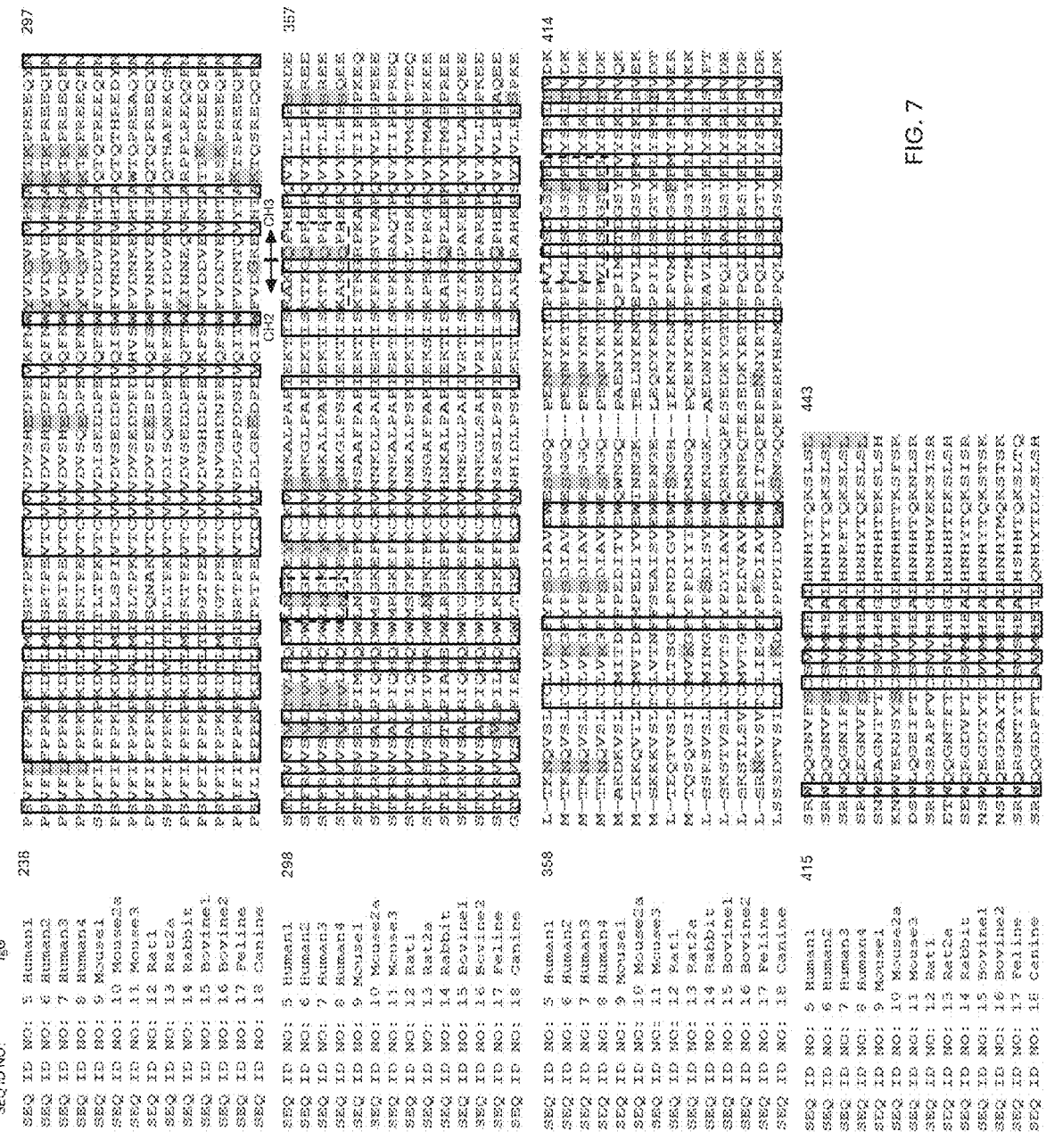
FIG. 7 shows sequence alignment of IgG constant region sequences from various species: human IgG1 (SEQ ID NO: 5), human IgG2 (SEQ ID NO: 6), human IgG3 (SEQ ID NO: 7), human IgG4 (SEQ ID NO: 8), murine IgG1 (SEQ NO: 9), murine IgG2a (SEQ NO: 10), murine IgG3 (SEQ ID NO: II), rat IgG1 (SEQ ID NO: 12), rat IgG2a (SEQ ID NO: 13), rabbit IgG (SEQ ID NO: 14), bovine IgG1 (SEQ ID NO: 15), bovine IgG2 (SEQ ID NO: 16), feline IgG (SEQ ID NO: 17), and canine IgG (SEQ ID NO: 18). Amino acid residues 347, 349, 354, and 360 are well-conserved in IgG molecules across multiple species.

In some embodiments, there is provided a heteromultimeric protein (e.g., heterodimeric protein) comprising a first polypeptide comprising a first CH3 domain and a second polypeptide comprising a second CH3 domain, wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, and wherein the amino acid residue numbering is based on EU numbering. In some embodiments, there is provided a heteromultimeric protein (e.g., heterodimeric protein) comprising a first polypeptide comprising a first GU domain and a second polypeptide comprising a second CH3 domain, wherein the first CH3 domain comprises a substitution relative to a wildtype CH3 domain at amino acid position 354 with a bulky hydrophobic amino acid, and/or a substitution relative to a wildtype CH3 domain at amino acid position 347 with a negatively charged amino acid, and wherein the amino acid residue numbering is based on EU numbering. In some embodiments, the bulky hydrophobic amino acid is tyrosine (Y), phenylalanine (F) or tryptophan (W). In some embodiments, the negatively charged amino acid is aspartic acid (D) or glutamic acid (E). In some embodiments, the bulky hydrophobic amino acid at amino acid position 354 in one CH3 domain forms a hydrophobic interaction with an amino acid residue in the other CH3 domain. In some embodiments, the other CH3 domain comprises a bulky hydrophobic residue at amino acid position 349 (e.g., Y349). In some embodiments, the negatively charged amino acid at amino acid position 347 in one CH3 domain forms an ionic bond with an amino acid residue in the other CH3 domain. In some embodiments, the other CH3 domain comprises a positively charged residue at amino acid position 360 (e.g., K360). In some embodiments, the first CH3 domain and the second CH3 domain further comprise KIH residues, such as T366Y and Y407T. In some embodiments, the first and second CH3 domains are human CH3 domains, murine CH3 domains, rat CH3 domains, camelid CH3 domains, or rabbit CH3 domains. FIG. 7 shows sequence alignment of sequences of the Fc region of IgG molecules from various species.

In some embodiments, there is provided a heteromultimeric protein (e.g., heterodimeric protein) comprising a first polypeptide comprising a first CH3 domain and a second polypeptide comprising a second CH3 domain, wherein the first CH3 domain comprises a substitution of S354 with a bulky hydrophobic amino acid, and/or the second CH3 domain comprises a substitution of Q347 with a negatively charged amino acid, and wherein the amino acid residue numbering is based on EU numbering. In some embodiments, there is provided a heteromultimeric protein (e.g., heterodimeric protein) comprising a first polypeptide comprising a first CH3 domain and a second polypeptide comprising a second CH3 domain, wherein the first CH3 domain comprises a substitution of S354 with a bulky hydrophobic amino acid, and/or a substitution of Q347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 in one CH3 domain forms a hydrophobic interaction with an amino acid residue in the other CH3 domain. In some embodiments, the other CH3 domain comprises a bulky hydrophobic residue at amino acid position 349 (e.g., Y349). In some embodiments, the negatively charged amino acid at amino acid position 347 in one CH3 domain forms an ionic bond with an amino acid residue in the other CH3 domain. In some embodiments, the other CH3 domain comprises a positively charged residue at amino acid position 360 (e.g., K360). In some embodiments, the CH3 domains are human CH3 domains. In some embodiments, the first CH3 domain and the second CH3 domain further comprise KIH residues, such as T366Y and Y407T.

In some embodiments, there is provided a heteromultimeric protein (e.g., heterodimeric protein) comprising a first polypeptide comprising a first human CH3 domain and a second polypeptide comprising a second human CH3 domain, wherein the first CH3 domain comprises S354Y, and the second CH3 domain comprises Q347E, and wherein the amino acid residue numbering is based on EU numbering. In some embodiments, S354Y in the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E in the second CH3 domain forms an ionic bond with an amino acid residue in the first CH3 domain. In some embodiments, the first CH3 domain comprises a positively charged residue at amino acid position 360 (e.g., K360). In some embodiments, the first CH3 domain and the second CH3 domain further comprise MIT residues. In some embodiments, the second CH3 domain does not comprise a substitution of Y349, e.g., Y349S.

The substitutions relative to a wildtype CH3 domain at amino acid positions 354 and 347 in the CH3 domains describe herein may be combined with any known mutations and/or engineered residues in the CH3 domain, which may promote heterodimer formation, including knob-into-holes ("KIH") mutations. Any KIH residues compatible with the substitutions at amino acid positions 354 and 347 can be used, including, for example, T366Y and Y407T. In some embodiments, the heteromultimeric protein does not comprise KIH residues in the CH3 domains. In some embodiments, the heteromultimeric protein comprises additional non-KIH mutations that promote heterodimer formation, such as cysteine residues that form disulfide bonds, and/or engineered residues that form electrostatic interactions. See, for example, U.S. Pat. No. 8,592,562.

In some embodiments, there is provided a heteromultimeric protein (e.g., heterodimeric protein) comprising a first polypeptide comprising a first human CH3 domain and a second polypeptide comprising a second human CH3 domain, wherein the first CH3 domain comprises S354Y and T366Y, and the second CH3 domain comprises Q347E and Y407T, and wherein the amino acid residue numbering is based on EU numbering. In some embodiments, S354Y in the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E in the second CH3 domain forms an ionic bond with an amino acid residue in the first CH3 domain. In some embodiments, the first C143 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains.

In some embodiments, there is provided a heteromultimeric protein (e.g., heterodimeric protein) comprising a first polypeptide comprising a first human CH3 domain and a second polypeptide comprising a second human CH3 domain, wherein the first CH3 domain comprises S354Y and Y407T, and the second CH3 domain comprises Q347E and T366Y and wherein the amino acid residue numbering is based on EU numbering. In some embodiments, S354Y in the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E in the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains.

The first polypeptide is any polypeptide which is to be associated with a second polypeptide. The first polypeptide and the second polypeptide interact with each other at an interface that includes the CH3-CH3 interface. In some embodiments, each of the first polypeptide and the second polypeptide may comprise one or more additional domains, such as binding domains (e.g., an antibody variable domain, receptor binding domain, ligand binding domain or enzymatic domain) and antibody constant domains (or parts thereof) including CH2, CH1, hinge and CL domains. Exemplary first and second polypeptides include antibody heavy chain polypeptides, chimeras combining an antibody constant domain with a binding domain of a heterologous polypeptide (i.e., an immunoadhesin, such as a receptor-Fc fusion polypeptide, a ligand-Fc fusion polypeptide), and antibody variable domain polypeptides (e.g., diabodies, bispecific maxibody, or bispecific peptibody).

mutant FC sequences are shown in Table 1. Those of skill in the art may differ in their understanding of the exact amino acids corresponding to the various domains of the IgG molecule. Thus, the N-terminus or C-terminus of the domains outlined herein may be extended or shortened by 1, 2, 3, 4, 5, 6, 7, 8, 9, or even 10 amino acids. Also, note that there are multiple known numbering schemes to designate amino acid positions in IgG, which may differ from the EU numbering scheme used in this patent application. In some embodiments, the Fc region is from the constant region of an IgA, IgD, IgE, or IgM heavy chain.

In some embodiments, there is provided a heteromultimeric protein (e.g., heterodimeric protein) comprising a first polypeptide comprising the CH3 domain (e.g., amino acids 116-217) of SEQ ID NO: 1, and a second polypeptide comprising the CH3 domain (e.g., amino acids 116-217) of SEQ ID NO: 2. In some embodiments, there is provided a heteromultimeric protein (e.g., heterodimeric protein) comprising a first polypeptide comprising the CH3 domain (e.g., amino acids 116-217) of SEQ ID NO: 3, and a second polypeptide comprising the CH3 domain (e.g., amino acids 116-217) of SEQ ID NO: 4. In some embodiments, there is provided a heteromultimeric protein (e.g., heterodimeric protein) comprising a first polypeptide comprising the amino acid sequence of SEQ ID NO: 1, and a second polypeptide comprising the amino acid sequence of SEQ ID NO: 2. In some embodiments, there is provided a heteromultimeric protein (e.g., heterodimeric protein) comprising a first polypeptide comprising the amino acid sequence of SEQ ID NO: 3, and a second polypeptide comprising the amino acid sequence of SEQ ID NO: 4.

TABLE 1

Exemplary IgG Fc sequences.

| SEQ ID NO | Description | Sequence |
|---|---|---|
| 1 | Fc1 with S354Y and T366Y | PPCPAPELLGGPSVFLFPPKPKDTLMISRTPEVTCVVVDVSHEDPEV KFNWYVDGVEVHNAKTKPREEQYNSTYRVVSVLTVLHQDLWLNGKEY KCKVSNKALPAPIEKTISKAKGQPREPQVYTLPPYREEMTKNQVSLY CLVKGFYPSDIAVEWESNGQPENNYKTTPPVLDSDGSFFLYSKLTVD KSRWQQGNVFSCSVMHEALHNHYTQKSLSLSPGK |
| 2 | Fc2 with Q347E and Y407T | PPCPAPELLGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPEVYTLPPSREEMTKNQVSLTC LVKGFYPSDIAVEWESNGQPENNYKTTPPVLDSDGSFFLTSKLTVDK SRWQQGNVFSCSVMHEALHNHYTQKSLSLSPGK |
| 3 | Fc1 with S354Y and Y407T | PPCPAPELLGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPQVYTLPPYREEMTKNQVSLTC LVKGFYPSDIAVEWESNGQPENNYKTTPPVLDSDGSFFLTSKLTVDK SRWQQGNVFSCSVMHELAHNHYTQKSLSLSPGK |
| 4 | Fc2 with Q347E and T366Y | PPCPAPELLGGPSVFLFPPKPKDTLMISRTPEVTCVVVDVSHEDPEV KFNWYVDGVEVHNAKTKPREEQYNSTYRVVSVLTVLHQDWLNGKEYK CKVSNKALPAPIEKTISKAKGQPREPEVYTLPPSREEMTKNQVSLYC LVKGFYPSDIAVEWESNGQPENNYKTTPPVLDSDGSFFLYSKLTVDK SRWQQGNVFSCSVMHEALHNHYTQKSLSLSPGK |

In some embodiments, the first polypeptide and/or the second polypeptide comprise a CH2 domain. In some embodiments, the first polypeptide and/or the second polypeptide comprise a CH1 domain and a CH2 domain. In some embodiments, the first polypeptide and the second polypeptide each comprises an Fc region of an IgG, such as a human IgG. In some embodiments, the first polypeptide and the second polypeptide each comprises an Fc region of an IgG1, IgG2, IgG3, or IgG4. Exemplary sequences of wildtype Fc region of IgG molecules are shown in FIG. 7. Exemplary Exemplary embodiments of the invention include but are not limited to an antibody, a multispecific antibody (e.g., bispecific antibody), a monospecific multivalent antibody, a bispecific maxibody (i.e., scFv-Fc fusion protein), a monobody (i.e., Fab-Fc), a peptibody (i.e., one peptide fused to one arm of a heterodimeric Fc molecule, including monovalent, bivalent, monospecific, and bispecific peptibody), an immunoadhesin, an antibody-immunoadhesin chimera, a receptor-Fc fusion protein, and a ligand-Fc fusion protein.

In some embodiments, the heteromultimeric protein is an antibody, such as a multispecific (e.g., bispecific) antibody. In some embodiments, the heteromultimeric protein comprises one or more antibody light chains. In some embodiments, the heteromultimeric protein is a common light chain antibody, i.e., a bispecific antibody comprising two identical light chains. In some embodiments, the heteromultimeric protein is a common variable light chain antibody, i.e., a bispecific antibody comprising two light chains having the same light chain variable regions. In some embodiments, the heteromultimeric protein comprises light chains having identical light chain variable regions. In some embodiments, the heteromultimeric protein comprises light chains comprising light chain variable regions derived from the same parent antibody. In some embodiments, the heteromultimeric protein comprises two different light chains. In some embodiments, the heteromultimeric protein comprises light chains derived from two different antibodies. In some embodiments, the heteromultimeric protein comprises lambda light chains. In some embodiments, the heteromultimeric protein comprises kappa light chains. In some embodiments, the heteromultimeric protein comprises a lambda light chain and a kappa light chain. Common light chain antibodies, including common variable light chain antibodies, are known in the art. See, for example, U.S. Pat. No. 8,642,745B2, and U.S. Pat. App. Pub. No. 2016/0319036A1, which are incorporated herein by reference. Any of the known common variable light chain strategies may be used in combination with the CH3-based heterodimerization strategy described herein to provide multispecific antibodies.

In some embodiments, the heteromultimeric protein is an antibody, such as a multispecific (e.g., bispecific) antibody that comprises a first antigen-binding fragment that binds a first antigen, and a second antigen binding fragment that binds a second antigen. In some embodiments, the heteromultimeric protein comprises a first and a second antigen-binding fragment that bind a first antigen, and a third antigen binding fragment that binds a second antigen. In some embodiments, the heteromultimeric protein comprises a first and a second antigen-binding fragment that bind a tumor antigen, and a third antigen binding fragment that binds a second antigen (such as CD3). In some embodiments, the heteromultimeric protein comprises a tumor antigen-binding region that has a relatively low affinity to a tumor antigen, so that it binds much more weakly to the healthy cells that have a lower density of the tumor antigen. In some embodiments, the first antigen-binding fragment, the second antigen binding fragment, and/or the third antigen binding fragment is a Fab. In some embodiments, the first antigen-binding fragment, the second antigen binding fragment, and/or the third antigen binding fragment is a VHH. In some embodiments, the first antigen-binding fragment, the second antigen binding fragment, and/or the third antigen binding fragment is an say. In some embodiments, the multispecific antibody comprises two Fab domains. In some embodiments, the multispecific antibody comprises three Fab domains. In some embodiments, the multispecific antibody comprises two VHH domains. In some embodiments, the multispecific antibody comprises three VHH domains. In some embodiments, the multispecific antibody comprises a Fab domain and a VHH domain. In some embodiments, the multispecific antibody comprises two Fab domains and a VHH domain. In some embodiments, the multispecific antibody comprises a Fab domain and two VHH domains. Exemplary structures of multispecific antibodies described herein are shown in FIG. 16.

In some embodiments, there is provided a multispecific (e.g., bispecific) antibody comprising: (a) a first heavy chain comprising from the N-terminus to the C-terminus: a first heavy chain variable domain a first heavy chain constant domain 1 (CH1), a first heavy chain constant domain 2 (CH2), and a first CH3 domain; (b) a first light chain comprising from the N-terminus to the C-terminus: a first light chain variable domain (VL1), and a first light chain constant domain (CL); (c) a second heavy chain comprising from the N-terminus to the C-terminus: a second heavy chain variable domain (VH2), a second CH1, a second CH2, and a second CH3 domain; and (d) a second light chain comprising from the N-terminus to the C-terminus: a second light chain variable domain (VL2), and a second CL; wherein VH1 and VL1 associate to form a first antigen binding site that specifically binds to a first target, and VH2 and VL2 associate to form a second antigen binding site that specifically binds to a second target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In some embodiments, the multispecific antibody is chimeric, human or humanized. In some embodiments, VL1 and VL2 have the same amino acid sequence. In some embodiments, VL1 and VL2 have different amino acid sequences.

In some embodiments, there is provided a multispecific (e.g., bispecific) antibody comprising: (a) a first heavy chain comprising from the N-terminus to the C-terminus: a VH1 domain, a first CH1 domain, a first CH2 domain, and a first CH3 domain; (b) a first light chain comprising from the N-terminus to the C-terminus: a VL1 domain, and a first CL domain; (c) a second heavy chain comprising from the N-terminus to the C-terminus: a VH2 domain, a second CH1 domain, a second CH2 domain, and a second CH3 domain; and (d) a second light chain comprising from the N-terminus to the C-terminus: a VL2 domain, and a second CL domain; wherein VH1 and VL1 associate to form a first antigen binding site that specifically binds to a first target, and VH2 and VL2 associate to form a second antigen binding site that specifically binds to a second target; wherein the first CH3 domain comprises a substitution of S354 with a bulky hydrophobic amino acid, and/or the second CH3 domain comprises a substitution of Q347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In sonic embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In sonic embodiments, the first CH3 domain and the second CH3 domain further comprise KIH residues, such as T366Y and Y407T. In some embodiments, the multispecific antibody is chimeric, human or humanized. In sonic embodiments, VL1 and VL2 have the same amino acid sequence. In some embodiments, VL1 and VL2 have different amino acid sequences.

In some embodiments, there is provided a multispecific (e.g., bispecific) antibody comprising: (a) a first heavy chain comprising from the N-terminus to the C-terminus: a VH1 domain, a first CH1 domain, a first CH2 domain, and a first CH3 domain; (b) a first light chain comprising from the N-terminus to the C-terminus: a VL1 domain, and a first CL domain; (c) a second heavy chain comprising from the N-terminus to the C-terminus: a VH2 domain, a second CH1 domain, a second CH2 domain, and a second CH3 domain; and (d) a second light chain comprising from the N-terminus to the C-terminus: a VL2 domain, and a second CL domain; wherein VH1 and VL1 associate to form a first antigen binding site that specifically binds to a first target, and VH2 and VL2 associate to form a second antigen binding site that specifically binds to a second target; wherein the first CH3 domain comprises S354Y and T366Y, and the second CH3 domain comprises Q347E and Y407T, and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CHS do not comprise other mutations compared to wildtype human CH3 domains. In some embodiments, the multispecific antibody is chimeric, human or humanized. In some embodiments, VL1 and VL2 have the same amino acid sequence. In some embodiments, VL1 and VL2 have different amino acid sequences. In some embodiments, the first antigen binding site specifically binds CD3 and the second antigen binding site specifically binds a tumor antigen, or the first antigen binding site specifically binds CD3 and the second antigen binding site specifically binds a tumor antigen. In some embodiments, the first antigen binding site specifically binds CD20 and the second antigen binding site specifically binds CD3, or the first antigen binding site specifically binds CD3 and the second antigen binding site specifically binds CD20. In some embodiments, the first antigen binding site specifically binds HER2 and the second antigen binding site specifically binds CD3, or the first antigen binding site specifically binds CD3 and the second antigen binding site specifically binds HER2.

In some embodiments, there is provided a multispecific (e.g., bispecific) antibody comprising: (a) a first heavy chain comprising from the N-terminus to the C-terminus: a VH1 domain, a first CH1 domain, a first CH2 domain, and a first CH3 domain; (b) a first light chain comprising from the N-terminus to the C-terminus: a VL1 domain, and a first CL domain; (c) a second heavy chain comprising from the N-terminus to the C-terminus: a VH2 domain, a second CH1 domain, a second CH2 domain, and a second CH3 domain; and (d) a second light chain comprising from the N-terminus to the C-terminus: a VL2 domain, and a second CL domain; wherein VH1 and VL1 associate to form a first antigen binding site that specifically binds to a first target, and VH2 and VL2 associate to form a second antigen binding site that specifically binds to a second target; wherein the first CH3 domain comprises S354Y and Y407T, and the second CH3 domain comprises Q347E and T366Y and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In sonic embodiments, Q347E of the second CH3 domain forms an ionic bond with an amino acid residue in the first CH3 domain. In some embodiments, the first CH3 domain comprises a positively charged residue at amino acid position 360 (e.g., K360), In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, VL1 and VL2 have the same amino acid sequence. In some embodiments, VL1 and VL2 have different amino acid sequences. In some embodiments, the first antigen binding site specifically binds CD3 and the second antigen binding site specifically binds a tumor antigen, or the first antigen binding site specifically binds CD3 and the second antigen binding site specifically binds a tumor antigen. In some embodiments, the first antigen binding site specifically binds CD20 and the second antigen binding site specifically binds CD3, or the first antigen binding site specifically binds CD3 and the second antigen binding site specifically binds CD20. In some embodiments, the first antigen binding site specifically binds HER2 and the second antigen binding site specifically binds CD3, or the first antigen binding site specifically binds CD3 and the second antigen binding site specifically binds HER2.

In some embodiments, there is provided a multispecific (e.g., bispecific) antibody comprising: (a) a first heavy chain comprising from the N-terminus to the C-terminus: a first VHH domain (VHH1), a first heavy chain constant domain 2 (CH2), and a first CH3 domain; and (b) a second heavy chain comprising from the N-terminus to the C-terminus: a second VHH domain (VHH2), a second CH2, and a second CH3 domain; wherein VHH1 specifically binds to a first target, and VHH2 specifically binds to a second target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific) antibody comprising: (a) a first heavy chain comprising from the N-terminus to the C-terminus: a first VHH domain (VHH1), a first heavy chain constant domain 2 (CH2), and a first CH3 domain; and (b) a second heavy chain comprising from the N-terminus to the C-terminus: a second VHH domain (VHH2), a second CH2, and a second CH3 domain; wherein VHH1 specifically binds to a first target, and VHH2 specifically binds to a second target; wherein the first CH3 domain comprises a substitution of S354 with a bulky hydrophobic amino acid, and/or the second CH3 domain comprises a substitution of Q347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific) antibody comprising: (a) a first heavy chain comprising from the N-terminus to the C-terminus: a first VHH domain (VHH1), a first heavy chain constant domain 2 (CH2), and a first CH3 domain; and (b) a second heavy chain comprising from the N-terminus to the C-terminus: a second VHH domain (VHH2), a second CH2, and a second CH3 domain; wherein VHH1 specifically binds to a first target, and WIFE specifically binds to a second target; wherein the first CH3 domain comprises S354Y and T366Y, and the second CH3 domain comprises Q347E and Y407T, and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized.

In some embodiments, there is provided a multispecific (e.g., bispecific) antibody comprising: (a) a first heavy chain comprising from the N-terminus to the C-terminus: a first VHH domain (VHH1), a first heavy chain constant domain 2 (CH2), and a first CH3 domain; and (b) a second heavy chain comprising from the N-terminus to the C-terminus: a second VHH domain (VHH2), a second CH2, and a second CH3 domain; wherein VHH1 specifically binds to a first target, and VHH2 specifically binds to a second target; wherein the first CH3 domain comprises S354Y and Y407T, and the second CH3 domain comprises Q347E and T366Y and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349), In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, Y349S. In some embodiments, the first CH3 and the second CH3 do not comprise other mutations compared to wildtype human CH3 domains. In some embodiments, the multispecific antibody is chimeric, human or humanized.

In some embodiments, there is provided a multispecific (e.g., bispecific) antibody comprising: (a) a first heavy chain comprising from the N-terminus to the C-terminus: a VHH domain, a first heavy chain constant domain 2 (CH2), and a first CH3 domain; (b) a second heavy chain comprising from the N-terminus to the C-terminus: a first heavy chain variable domain (VH1), a first CH1, a second CH2, and a second CH3 domain; and (d) a light chain comprising from the N-terminus to the C-terminus: a first light chain variable domain (VL1), and a first CL; wherein VH1 and VL1 associate to form a first antigen binding site that specifically binds to a first target, and the VHH domain specifically binds to a second target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, or wherein the second CH3 domain comprises a substitution relative to a wildtype CH3 domain at amino acid position 354 with a bulky hydrophobic amino acid, and/or the first CH3 domain comprises a substitution relative to a wildtype CH3 domain at amino acid position 347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific) antibody comprising: (a) a first heavy chain comprising from the N-terminus to the C-terminus: a VHH domain, a first heavy chain constant domain 2 (CH2), and a first CH3 domain; (b) a second heavy chain comprising from the N-terminus to the C-terminus: a first heavy chain variable domain (VH1), a first CH1, a second CH2, and a second CH3 domain; and (d) a light chain comprising from the N-terminus to the C-terminus: a first light chain variable domain (VL1), and a first CL; wherein VH1 and VL1 associate to form a first antigen binding site that specifically binds to a first target, and the VHH domain specifically binds to a second target, wherein the first CH3 domain comprises a substitution of S354 with a bulky hydrophobic amino acid, and/or the second CH3 domain comprises a substitution of Q347 with a negatively charged amino acid, or wherein the second CH3 domain comprises a substitution of S354 with a bulky hydrophobic amino acid, and/or the first CH3 domain comprises a substitution of Q347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In sonic embodiments, the first CH3 domain and the second CH3 domain further comprise KIH residues, such as T366Y and Y407T.

In some embodiments, there is provided a multispecific (e.g., bispecific) antibody comprising: (a) a first heavy chain comprising from the N-terminus to the C-terminus: a VHH domain, a first heavy chain constant domain 2 (CH2), and a first CH3 domain; (b) a second heavy chain comprising from the N-terminus to the C-terminus: a first heavy chain variable domain (VH1), a first CH1, a second CH2, and a second CH3 domain; and (d) a light chain comprising from the N-terminus to the C-terminus: a first light chain variable domain (VL1) and a first CL; wherein VH1 and VL1 associate to form a first antigen binding site that specifically binds to a first target, and the VHH domain specifically binds to a second target; wherein the first CH3 domain comprises S354Y and T366Y, and the second CH3 domain comprises Q347E and Y407T, or wherein the second CH3 domain comprises S354Y and T366Y, and the first CH3 domain comprises Q347E and Y407T; and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349), In some embodiments. Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, the VHH specifically binds to a tumor antigen (e.g., BCMA), and the first antigen binding site specifically binds to CD3.

In some embodiments, there is provided a multispecific (e.g., bispecific) antibody comprising: (a) a first heavy chain comprising from the N-terminus to the C-terminus: a VHH domain, a first heavy chain constant domain 2 (CH2), and a first CH3 domain; (b) a second heavy chain comprising from the N-terminus to the C-terminus: a first heavy chain variable domain (VH1), a first CH1, a second CH2, and a second CH3 domain; and (d) a light chain comprising from the N-terminus to the C-terminus: a first light chain variable domain (VL1), and a first CL; wherein VH1 and VL1 associate to form a first antigen binding site that specifically binds to a first target, and the VHH domain specifically binds to a second target; wherein the first CH3 domain comprises S354Y and Y407T, and the second CH3 domain comprises Q347E and T366Y, or wherein the second CH3 domain comprises S354Y and Y407T, and the first CH3 domain comprises Q347E and T366Y; and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, the VHH specifically binds to a tumor antigen (e.g., BCMA), and the first antigen binding site specifically binds to CD3.

In some embodiments, there is provided a multispecific bispecific or trispecific) antibody comprising: (a) a first heavy chain comprising from the N-terminus to the C-terminus: a first heavy chain variable domain (VH1), a first CH1, a second heavy chain variable domain (VH2), a second CH1, a first CH2, and a first CH3 domain; (b) a first light chain comprising from the N-terminus to the C-terminus: a first light chain variable domain (VL1), a first CL, a second light chain variable domain (VL2), and a second CL; (c) a second heavy chain comprising from the N-terminus to the C-terminus: a third heavy chain variable domain (VH3), a third CH1, a second CH2, and a second CH3 domain; and (d) a second light chain comprising from the N-terminus to the C-terminus: a third light chain variable domain (VL3), and a third CL; wherein VH1 and VL1 associate to form a first antigen binding site that specifically binds to a first target, VH2 and VL2 associate to form a second antigen binding site that specifically binds to a second target, and VH3 and VL3 associate to form a third antigen binding site that specifically binds to a third target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, or wherein the second CH3 domain comprises a substitution relative to a wildtype CH3 domain at amino acid position 354 with a bulky hydrophobic amino acid, and/or the first CH3 domain comprises a substitution relative to a wildtype CH3 domain at amino acid position 347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second. CH3 domain further comprise residues, such as T366Y and Y407T. In some embodiments, the multispecific antibody is chimeric, human or humanized. In some embodiments, VL1, VL2 and/or VL3 have the same amino acid sequence. In some embodiments, VL1, VL2 and VL3 have different amino acid sequences.

In some embodiments, there is provided a multispecific (e.g., bispecific or trispecific) antibody comprising: (a) a first heavy chain comprising from the N-terminus to the C-terminus: a first heavy chain variable domain (VH1), a first CH1, a second heavy chain variable domain (VH2), a second CH1, a first CH2, and a first CH3 domain; (b) a first light chain comprising from the N-terminus to the C-terminus: a first light chain variable domain (VL1), a first CL, a second light chain variable domain (VL2), and a second CL; (c) a second heavy chain comprising from the N-terminus to the C-terminus: a third heavy chain variable domain (VH3), a third CH1, a second CH2, and a second CH3 domain; and (d) a second light chain comprising from the N-terminus to the C-terminus: a third light chain variable domain (VL3), and a third CL; wherein VH1 and VL1 associate to form a first antigen binding site that specifically binds to a first target, VH2 and VL2 associate to form a second antigen binding site that specifically binds to a second target, and VH3 and VL3 associate to form a third antigen binding site that specifically binds to a third target; wherein the first CH3 domain comprises a substitution of S354 with a bulky hydrophobic amino acid, and/or the second CH3 domain comprises a substitution of Q347 with a negatively charged amino acid, or wherein the second CH3 domain comprises a substitution of S354 with a bulky hydrophobic amino acid, and/or the first CH3 domain comprises a substitution of Q347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first CH3 domain and the second CH3 domain further comprise KIH residues, such as T366Y and Y407T, In some embodiments, the multispecific antibody is chimeric, human or humanized. In some embodiments, VL1, VL2 and/or VL3 have the same amino acid sequence. In some embodiments, VL1, VL2 and VL3 have different amino acid sequences.

In some embodiments, there is provided a multispecific (e.g., bispecific or trispecific) antibody comprising: (a) a first heavy chain comprising from the N-terminus to the C-terminus: a first heavy chain variable domain (VH1), a first CH1, a second heavy chain variable domain (VH2), a second CH1, a first CH2, and a first CH3 domain; (b) a first light chain comprising from the N-terminus to the C-terminus: a first light chain variable domain (VL1), a first CL, a second light chain variable domain (VL2), and a second CL; (c) a second heavy chain comprising from the N-terminus to the C-terminus: a third heavy chain variable domain (VH3), a third CH1, a second CH2, and a second CH3 domain; and (d) a second light chain comprising from the N-terminus to the C-terminus: a third light chain variable domain (VL3), and a third CL; wherein VH1 and VL1 associate to form a first antigen binding site that specifically binds to a first target, VH2 and VL2 associate to form a second antigen binding site that specifically binds to a second target, and VH3 and VL3 associate to form a third antigen binding site that specifically binds to a third target; wherein the first CH3 domain comprises S354Y and T366Y, and the second CH3 domain comprises Q347E and Y407T, or wherein the second CH3 domain comprises S354Y and T366Y, and the first CH3 domain comprises Q347E and Y407T; and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, VL1, VL2 and/or VL3 have the same amino acid sequence. In some embodiments, VL1, VL2 and VL3 have different amino acid sequences. In some embodiments, the first antigen binding site and the second antigen binding site specifically binds a tumor antigen (e.g., HER2), and the third antigen binding site specifically binds CD3.

In some embodiments, there is provided a multispecific (e.g., bispecific or trispecific) antibody comprising: (a) a first heavy chain comprising from the N-terminus to the C-terminus: a first heavy chain variable domain (VH1), a first CH1, a second heavy chain variable domain (VH2), a second CH1, a first CH2, and a first CH3 domain; (b) a first light chain comprising from the N-terminus to the C-terminus: a first light chain variable domain (VL1), a first CL, a second light chain variable domain (VL2), and a second CL; (c) a second heavy chain comprising from the N-terminus to the C-terminus: a third heavy chain variable domain (VH3), a third CH1, a second CH2, and a second CH3 domain; and (d) a second light chain comprising from the N-terminus to the C-terminus: a third light chain variable domain (VL3), and a third CL; wherein VH1 and VL1 associate to form a first antigen binding site that specifically binds to a first target, VH2 and VL2 associate to form a second antigen binding site that specifically binds to a second target, and VH3 and VL3 associate to form a third antigen binding site that specifically hinds to a third target; wherein the first CH3 domain comprises S354Y and Y407T, and the second CH3 domain comprises Q347E and T366Y, or wherein the second CH3 domain comprises S354Y and Y407T, and the first CH3 domain comprises Q347E and T366Y; and wherein the amino acid residue numbering is based on EU numbering. In some embodiments. S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360), In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, VL1, VL2 and/or VL3 have the same amino acid sequence. In some embodiments, VL1, VL2 and VL3 have different amino acid sequences. In sonic embodiments, the first antigen binding site and the second antigen binding site specifically binds a tumor antigen (e.g., HER2), and the third antigen binding site specifically binds CD3.

In some embodiments, there is provided a multispecific (e.g., bispecific or trispecific) antibody comprising: (a) a first heavy chain comprising from the N-terminus to the C-terminus: a first VHH domain (VHH1), a second VHH domain (VHH2), a first CH2, and a first CH3 domain; (h) a second heavy chain comprising from the N-terminus to the C-terminus: a third VHH domain (VHH3), a second CH2, and a second CH3 domain; wherein VHH1 specifically binds to a first target, VHH2 specifically binds to a second target, and VHH3 specifically binds to a third target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, or wherein the second CH3 domain comprises a substitution relative to a wildtype CH3 domain at amino acid position 354 with a bulky hydrophobic amino acid, and/or the first CH3 domain comprises a substitution relative to a wildtype CH3 domain at amino acid position 347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific or trispecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a third VHH domain (VHH3), a second CH2, and a second CH3 domain; wherein VHH1 specifically binds to a first target, VHH2 specifically binds to a second target, and VHH3 specifically binds to a third target; wherein the first CH3 domain comprises a substitution of S354 with a bulky hydrophobic amino acid, and/or the second CH3 domain comprises a substitution of Q347 with a negatively charged amino acid, or wherein the second CH3 domain comprises a substitution of S354 with a bulky hydrophobic amino acid, and/or the first CH3 domain comprises a substitution of Q347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific or trispecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a third VHH domain (VHH3), a second. CH2, and a second CH3 domain; wherein VHH1 specifically hinds to a first target, VHH2 specifically binds to a second target, and VHH3 specifically binds to a third target; wherein the first CH3 domain comprises S354Y and T366Y, and the second. CH3 domain comprises Q347E and Y407T, or wherein the second CH3 domain comprises S354Y and T366Y, and the first CH3 domain comprises Q347E and Y407T; and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second GU domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized.

In some embodiments, there is provided a multispecific (e.g., bispecific or trispecific) antibody comprising: (a) a first heavy chain comprising from the N-terminus to the C-terminus: a first VHH domain (VHH1), a second ATM domain (VHH2), a first CH2, and a first CH3 domain; (b.) a second heavy chain comprising from the N-terminus to the C-terminus: a third VHH domain (VHH3), a second CH2, and a second CH3 domain; wherein VHH1 specifically binds to a first target, VHH2 specifically binds to a second target, and VHH3 specifically binds to a third target; wherein the first CH3 domain comprises S354Y and Y407T, and the second CH3 domain comprises Q347E and T366Y, or wherein the second CH3 domain comprises S354Y and Y407T, and the first CH3 domain comprises Q347E and T366Y; and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CHS domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second. CH3 do not comprise other mutations compared to wildtype human CH3 domains. In some embodiments, the multispecific antibody is chimeric, human or humanized.

In some embodiments, there is provided a multispecific (e.g., bispecific or trispecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a first heavy chain variable domain (VH1), a first CH1, a second CH2, and a second CH3 domain; and (c) a light chain comprising from the N-terminus to the C-terminus: a first light chain variable domain (VL1), and a first CL; wherein VH1 and VL1 associate to form a first antigen binding site that specifically binds to a first target, VHH1 specifically hinds to a second target, and VHH2 specifically hinds to a third target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, or wherein the second CH3 domain comprises a substitution relative to a wildtype CH3 domain at amino acid position 354 with a bulky hydrophobic amino acid, and/or the first CH3 domain comprises a substitution relative to a wildtype CH3 domain at amino acid position 347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific or trispecific) antibody comprising: (a) a first heavy chain comprising from the N-terminus to the C-terminus: a first VHH domain (VHH1) a second VHH domain (VHH2), a first CH2, and a first CH3 domain; (b) a second heavy chain comprising from the N-terminus to the C-terminus: a first heavy chain variable domain (VH1), a first CH1, a second CH2, and a second CH3 domain; and (c) a light chain comprising from the N-terminus to the C-terminus: a first light chain variable domain (VL1), and a first CL; wherein VH1 and VL1 associate to form a first antigen binding site that specifically binds to a first target, VHH1 specifically binds to a second target, and VHH2 specifically binds to a third target; wherein the first CH3 domain comprises a substitution of S354 with a bulky hydrophobic amino acid, and/or the second CH3 domain comprises a substitution of Q347 with a negatively charged amino acid, or wherein the second CH3 domain comprises a substitution of S354 with a bulky hydrophobic amino acid, and/or the first CH3 domain comprises a substitution of Q347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In sonic embodiments, the first CH3 domain and the second CH3 domain further comprise KIH residues, such as T366Y and Y407T. In some embodiments, the multispecific antibody is chimeric, human or humanized.

In some embodiments, there is provided a multispecific (e.g., bispecific or trispecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a first heavy chain variable domain (VH1), a first CH1, a second CH2, and a second CH3 domain; and (c) a light chain comprising from the N-terminus to the C-terminus: a first light chain variable domain (VL1), and a first CL; wherein VH1 and VL1 associate to form a first antigen binding site that specifically binds to a first target, VHH1 specifically binds to a second target, and VHH2 specifically binds to a third target; wherein the first CH3 domain comprises S354Y and T366Y, and the second CH3 domain comprises Q347E and Y407T, or wherein the second CH3 domain comprises S354Y and T366Y, and the first CH3 domain comprises Q347E and Y407T, and wherein the amino acid residue numbering is based on EU numbering. In some embodiments, S354Y of the first CH3 domain forms a hydrophobic interaction with an amino acid residue in the second CH3 domain. In some embodiments, the second GU domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, VHH1 and VHH2 specifically binds to a tumor antigen (e.g., BCMA), and the first antigen binding site specifically binds to CD3.

In some embodiments, there is provided a multispecific (e.g., bispecific or trispecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a first heavy chain variable domain (VH1), a first CH1, a second CH2, and a second CH3 domain; and (c) a light chain comprising from the N-terminus to the C-terminus: a first light chain variable domain (VL1), and a first CL; wherein VH1 and VL1 associate to form a first antigen binding site that specifically binds to a first target, VHH1 specifically hinds to a second target, and VHH2 specifically hinds to a third target; wherein the first CH3 domain comprises S354Y and Y407T, and the second CH3 domain comprises Q347E and T366Y, or wherein the second CH3 domain comprises S354Y and Y407T, and the first CH3 domain comprises Q347E and T366Y; and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized. In some embodiments, VHH1 and VHH2 specifically binds to a tumor antigen (e.g., BCMA), and the first antigen binding site specifically binds to CD3.

In some embodiments, there is provided a multispecific (e.g., bispecific, trispecific, or tetraspecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a third VHH domain (VHH3), a fourth VHH domain (VHH4), a second CH2, and a second CH3 domain; wherein VHH1 specifically hinds to a first target, VHH2 specifically binds to a second target, VHH3 specifically binds to a third target, and VHH4 specifically binds to a fourth target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second GU domain. In sonic embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In some embodiments, the multispecific antibody is chimeric, human or humanized.

In some embodiments, there is provided a multispecific bispecific, trispecific, or tetraspecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a third VHH domain (VHH3), a fourth VHH domain (VHH4), a second CH2, and a second CH3 domain; wherein VHH1 specifically binds to a first target, VHH2 specifically binds to a second target, VHH3 specifically binds to a third target, and VHH4 specifically binds to a fourth target; wherein the first CH3 domain comprises a substitution of S354 with a bulky hydrophobic amino acid, and/or the second CH3 domain comprises a substitution of Q347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first CRS domain and the second CH3 domain further comprise MEI residues, such as T366Y and Y407T. In some embodiments, the multispecific antibody is chimeric, human or humanized.

In some embodiments, there is provided a multispecific (e.g., bispecific, trispecific, or tetraspecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a third VHH domain (VHH3), a fourth VHH domain (VHH4), a second CH2, and a second CH3 domain; wherein VHH1 specifically hinds to a first target, VHH2 specifically binds to a second target, VHH3 specifically binds to a third target, and VHH4 specifically binds to a fourth target; wherein the first CH3 domain comprises S354Y and T366Y, and the second CH3 domain comprises Q347E and Y407T, and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized.

In some embodiments, there is provided a multispecific (e.g., bispecific, trispecific, or tetraspecific) antibody comprising: (a) a first heavy chain comprising from the N-terminus to the C-terminus: a first VHH domain (VHH1), a second VHH domain (VHH2), a first CH2, and a first CH3 domain; (b) a second heavy chain comprising from the N-terminus to the C-terminus: a third VHH domain (VHH3), a fourth VHH domain (VHH4), a second CH2, and a second CH3 domain; wherein VHH1 specifically binds to a first target, VHH2 specifically binds to a second target, VHH3 specifically binds to a third target, and VHH4 specifically hinds to a fourth target; wherein the first CH3 domain comprises S354Y and Y407T, and the second CH3 domain comprises Q347E and T366Y and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CH3 domain does not comprise a substitution of Y349, e.g., Y349S. In some embodiments, the first CH3 and the second CH3 do not comprise other mutations compared to wildtype human CH3 domains. In some embodiments, the multispecific antibody is chimeric, human or humanized.

Also provided are multispecific antibodies comprising any one of the first CH3 domain and the second CH3 domains described herein. In some embodiments, the present application provides a bispecific T cell engager (BiTE) molecule comprising a first antigen binding fragment that specifically binds to a tumor antigen, a second antigen binding fragment that specifically binds to CD3, and any one of the mutant Fc regions described herein. In some embodiments, the present application provides a bispecific T cell engager (BiTE) molecule comprising a first antigen binding fragment and a second antigen binding fragment that specifically binds to a tumor antigen, a third antigen binding fragment that specifically binds to CD3, and any one of the mutant Fc regions described herein. In some embodiments, the present application provides a multispecific (e.g., bispecific or trispecific) antibody that specifically bind to CD20 and CD3. In some embodiments, the present application provides a bispecific antibody that specifically bind to HER2 and CD3. In some embodiments, the present application provides a multispecific (e.g., bispecific or trispecific) antibody that specifically bind to CD3 and BCMA. Any suitable antigen binding fragments may be used for the multispecific antibodies described herein, including, for example, anti-CD20 and anti-CD3 antigen binding fragments described in International Application No. PCT/US2018/044778 or International Application No. PCT/US2020/015311.

In some embodiments, the heteromultimeric protein is a heteromultimeric immunoadhesin. Immunoadhesins are antibody-like molecules, which combine the binding domain of a protein such as a cell-surface receptor, or a ligand (an "adhesin") with the effector functions of an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. In some embodiments, the heteromultimeric protein is a multispecific immunoadhesin, such as a bispecific immunoadhesin, i.e., the two arms of the immunoadhesin have different specificities.

In some embodiments, the heteromultimeric protein is an antibody-immunoadhesin chimera. These molecules combine the binding region of an immunoadhesin with the binding domain of an antibody. Exemplary antibody-immunoadhesin chimeras have been described, for example, in Berg et al., PNAS (USA) 88: 4723-4727 (1991) and Chamow et al., J. Immunol. 153: 4268 (1994).

In some embodiments, the heteromultimeric protein is an immunoadhesin or an antibody-immunoadhesin chimera comprising one or more binding domains that are not antibody fragments, such as a ligand binding domain, a receptor binding domain, or an enzyme domain. The term "ligand binding domain" as used herein refers to any native cell-surface receptor or any region or derivative thereof retaining at least a qualitative ligand binding ability, and preferably the biological activity of a corresponding native receptor. In some embodiments, the receptor is from a cell-surface polypeptide having an extracellular domain which is homologous to a member of the immunoglobulin superfamily. Other typical receptors, are not members of the immunoglobulin superfamily but are nonetheless specifically covered by this definition, are receptors for cytokines, receptors with tyrosine kinase activity (receptor tyrosine kinases), members of the hematopoietin and nerve growth factor receptor superfamilies, and cell adhesion molecules, e.g., (E-, L- and P-) selectins.

The term "receptor binding domain" refers to any native ligand for a receptor, including cell adhesion molecules, or any region or derivative of such native ligand retaining at least a qualitative receptor binding ability, and preferably the biological activity of a corresponding native ligand. This definition, among others, specifically includes binding sequences from ligands for the above-mentioned receptors.

In some embodiments, there is provided a multispecific (e.g., bispecific) immunoadhesin comprising: (a) a first polypeptide comprising from the N-terminus to the C-terminus: a first binding domain that specifically binds a first target, a first CH2 domain, and a first CH3 domain; (b) a second polypeptide comprising from the N-terminus to the C-terminus: a second binding domain that specifically binds a second target, a second CH2 domain, and a second CH3 domain; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid, and wherein the amino acid residue numbering is based on EU numbering. In sonic embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In sonic embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains, murine CH3 domains, rat CH3 domains, camelid CH3 domains, or rabbit CH3 domains. In some embodiments, the first CH3 domain and the second CH3 domain further comprise KIH residues, such as T366Y and Y407T. In sonic embodiments, the first binding domain and the second binding domain are receptor binding domains. In some embodiments, the first binding domain and the second binding domain are ligand binding domains. In some embodiments, the first binding domain is a receptor binding domain and the second binding domain is a ligand binding domain, or the first binding domain is a ligand binding domain and the second binding domain is a receptor binding domain.

In some embodiments, there is provided a multispecific (e.g., bispecific) immunoadhesin comprising: (a) a first polypeptide comprising from the N-terminus to the C-terminus: a first binding domain that specifically binds a first target, a first CH2 domain, and a first CH3 domain; (b) a second polypeptide comprising from the N-terminus to the C-terminus: a second binding domain that specifically binds a second target, a second CH2 domain, and a second CH3 domain; wherein the first CH3 domain comprises a substitution of S354 with a bulky hydrophobic amino acid, and/or the second CH3 domain comprises a substitution of Q347 with a negatively charged amino acid, and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first CH3 domain and the second CH3 domain further comprise KIH residues, such as T366Y and Y407T. In some embodiments, the first binding domain and the second binding domain are receptor binding domains. In some embodiments, the first binding domain and the second binding domain are ligand binding domains. In some embodiments, the first binding domain is a receptor binding domain and the second binding domain is a ligand binding domain, or the first binding domain is a ligand binding domain and the second binding domain is a receptor binding domain.

In some embodiments, there is provided a multispecific (e.g., bispecific) immunoadhesin comprising: (a) a first polypeptide comprising from the N-terminus to the C-terminus: a first binding domain that specifically binds a first target, a first CH2 domain, and a first CH3 domain; (b) a second polypeptide comprising from the N-terminus to the C-terminus: a second binding domain that specifically binds a second target, a second CH2 domain, and a second CH3 domain; wherein: (i) the first CH3 domain comprises S354Y and T366Y, and the second CH3 domain comprises Q347E and Y407T, or (ii) the first CH3 domain comprises S354Y and Y407T, and the second CH3 domain comprises Q347E and T366Y, and wherein the amino acid residue numbering is based on EU numbering. In some embodiments, S354Y of the first CH3 domain forms a hydrophobic interaction with an amino acid residue in the second CH3 domain. In some embodiments, the second CH3 domain comprises a bulky hydrophobic residue at amino acid position 349 (e.g., Y349). In some embodiments, Q347E of the second CH3 domain forms an ionic bond with an amino acid residue in the first CH3 domain. In some embodiments, the first CH3 domain comprises a positively charged residue at amino acid position 360 (e.g., K360). In some embodiments, the second CHS domain does not comprise a substitution of Y349, e.g., Y349S. In some embodiments, the first CH3 and the second CH3 do not comprise other mutations compared to wildtype human CH3 domains. In some embodiments, the first binding domain and the second binding domain are receptor binding domains. In some embodiments, the first binding domain and the second binding domain are ligand binding domains. In some embodiments, the first binding domain is a receptor binding domain and the second binding domain is a ligand binding domain, or the first binding domain is a ligand binding domain and the second binding domain is a receptor binding domain.

The multispecific antibodies and multispecific immunoadhesin described herein may specifically bind to any suitable combination of epitopes, antigens or target molecules. In some embodiments, the first target, the second target, the third target and the fourth target are the same epitope. In some embodiments, the first target, the second target, the third target and/or the fourth target are different epi topes of the same antigen. In some embodiments, the first target, the second target, the third target and the fourth target are different antigens. In some embodiments, the first target, the second target, the third target and the fourth target are different target molecules.

In some embodiments, the first target, the second target, the third target and/or the fourth target are cell surface molecules. In some embodiments, the first target, the second target, the third target and/or the fourth target are tumor antigens. Tumor antigens are proteins that are produced by tumor cells that can elicit an immune response, particularly T-cell mediated immune responses. The selection of the targeted antigen of the invention will depend on the particular type of cancer to be treated. Exemplary tumor antigens include, for example, a glioma-associated antigen, carci-noembryonic antigen (CEA), β-human chorionic gonado-tropin, alphafetoprotein (AFP), lectin-reactive AFP, thyro-globulin, RAGE-1, MN-CAIX, human telomerase reverse transcriptase, RU1, RU2 (AS), intestinal carboxyl esterase, mut hsp70-2, M-CSF, prostate, prostate-specific antigen (PSA), PAP, NY-ESO-1, LADE-1a, p53, protein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malig-nant tumor. Malignant tumors express a number of proteins that can serve as target antigens for an immune attack. These molecules include but are not limited to tissue-specific antigens such as MART-1, tyrosinase and gp100 in mela-noma and prostatic acid phosphatase (PAP) and prostate-specific antigen (PSA) in prostate cancer. Other target mol-ecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD 19, CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase. TRP-1, TRP-2 and tumor-specific multilineage antigens such as MAGE-1, MAGE-3, BAGE, GAGE-1, GAGE-2, p15; over-expressed embryonic antigens such as CEA; overexpressed oncogenes and mutated tumor-suppressor genes such as p53, Ras, HER2/neu; unique tumor antigens resulting from chro-mosomal translocations; such as BCR-ABL, E2A-PRL, H4-RET, IGH-IGK, MYL-RAR; and viral antigens, such as the Epstein Ban virus antigens EBVA and the human pap-illomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated pro-tein, TAAL6, TAG-72, TLP, and TPS.

In some embodiments, the first target, the second target, the third target and/or the fourth target is an immune checkpoint molecule, such as a stimulatory immune check-point molecule, or an inhibitory immune checkpoint mol-ecule. Exemplary stimulatory immune checkpoint mol-ecules include, but are not limited to, CD28, OX40, ICOS, GITR, 4-1BB, CD27, CD40, CD3, HVEM, and TCR (e.g., MHC class I or class II molecules). Exemplary inhibitory immune checkpoint molecules include, but are not limited to, CTLA-4, TIM-3, A2a Receptor, LAG-3, BRA, KIR, PD-1, ID0, CD47, and ligands thereof such as B7.1, B7.2, PD-L1, PD-L2, HVEM, B7-1-14, NKTR-218, and SIRP-alpha receptor.

In some embodiments, the first target, the second target, the third target and/or the fourth target is an antigen on immune effector cells, such as T cells, B cells, macrophages or Natural Killer cells. In some embodiments, the first target, the second target, the third target or the fourth target is CD3. In some embodiments, the first target is CD3 and the second target is a tumor antigen, or the first target is a tumor antigen and the second target is CD3. In some embodiments, the first target is CD3 and the second target and the third target is a tumor antigen.

Also provided are individual polypeptides of any one of the heteromultimeric proteins described herein.

In some embodiments, there is provided a polypeptide comprising an antibody CH3 domain, wherein the CH3 domain comprises a substitution relative to a wildtype CH3 domain at amino acid position 354 with a bulky hydrophobic amino acid and/or a substitution relative to a wildtype CH3 domain at amino acid position 347 with a negatively charged amino acid, and wherein the polypeptide has decreased ability to form homodimers compared to a polypeptide comprising a wildtype CH3 domain. In some embodiments, the bulky hydrophobic amino acid is Y, F or W. In some embodiments, the negatively charged amino acid is D or E. In some embodiments, the CH3 domain is a human CH3 domain, a murine CH3 domain, a rat CH3 domain, a camelid CH3 domain, or a rabbit CH3 domain. In some embodi-ments, the CH3 domain further comprise a KIH residue, such as T366Y or Y407T. In some embodiments, the poly-peptide comprises a CH2 domain. In some embodiments, the polypeptide comprises an antibody heavy chain.

In some embodiments, there is provided a polypeptide comprising a human antibody CH3 domain, wherein the CH3 domain comprises a substitution of S354 with a bulky hydrophobic amino acid and/or a substitution of Q347 with a negatively charged amino acid, and wherein the polypep-tide has decreased ability to form homodimers compared to a polypeptide comprising a wildtype CH3 domain. In some embodiments, the CH3 domain comprises a substitution selected from the group consisting of S354Y, S354F and S354W. In some embodiments, the CH3 domain comprises a substitution selected from the group consisting of Q347E and Q347D. In some embodiments, the CH3 domain further comprise a KIH residue, such as T366Y or Y407T. In some embodiments, the polypeptide comprises a CH2 domain. In some embodiments, the polypeptide comprises an antibody heavy chain Variants and derivatives of any one of the heteromultim-eric proteins or polypeptides described above are also pro-vided herein.

In some embodiments, amino acid sequence variants of the heteromultimeric proteins (e.g., multispecific antibodies) provided herein are contemplated. For example, it may be desirable to improve the binding affinity and/or other bio-logical properties of the heteromultimeric protein. Amino acid sequence variants of a heteromultimeric protein may be prepared by introducing appropriate modifications into the nucleotide sequence encoding the heteromultimeric protein, or by peptide synthesis. Such modifications include, for example, deletions from, and/or insertions into and/or substitutions of residues within the amino acid sequences of the heteromultimeric protein. Any combination of deletion, insertion, and substitution can be made to arrive at the final construct, provided that the final construct possesses the desired characteristics, e.g., antigen-binding.

In some embodiments, heteromultimeric protein variants having one or more amino acid substitutions are provided. Sites of interest for substitutional mutagenesis include the CDRs and FRs of a multispecific antibody. Amino acid substitutions may be introduced into a multispecific antibody of interest and the products screened for a desired activity, e.g., retained/improved antigen binding and cleavage, decreased immunogenicity, or improved ADCC or CDC.

Conservative substitutions are shown in Table 2 below.

TABLE 2

CONSERVATIVE SUBSTITUTIONS

| Original Residue | Exemplary Substitutions | Preferred Substitutions |
|---|---|---|
| Ala (A) | Val; Leu; Ile | Val |
| Arg (R) | Lys; Gln, Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;
b. neutral hydrophilic: Cys, Ser, Thr, Asn, Gln;
c. acidic: Asp, Glu;
d. basic: His, Lys, Arg;
e. residues that influence chain orientation: Gly, Pro;
f. aromatic: Trp, Tyr, Phe.

Non-conservative substitutions swill entail exchanging a member of one of these classes for another class.

In some embodiments, substitutions, insertions, or deletions may occur within one or more CDRs so long as such alterations do not substantially reduce the ability of the multispecific antibody to bind antigen. For example, conservative alterations (e.g., conservative substitutions as provided herein) that do not substantially reduce binding affinity may be made in CDRs. Such alterations may be outside of HVR "hotspots" or SDRs.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a heteromultimeric protein with an N-terminal methionyl residue. Other insertional variants of the heteromultimeric protein include the fusion to the N- or C-terminus of the heteromultimeric protein to an enzyme (e.g. for ADEPT) or a polypeptide which increases the serum half-life of the heteromultimeric protein.

Heteromultimeric protein variants are also provided with amino-terminal leader extensions. For example, one or more amino acid residues of the amino-terminal leader sequence are present at the amino-terminus of any one or more heavy or light chains of an antibody.

Covalent modifications of the heteromultimeric proteins are also included within the scope of this invention. Covalent modifications of the heteromultimeric protein can be introduced into the molecule by reacting targeted amino acid residues of the heteromultimeric protein or fragments thereof with an organic derivatizing agent that is capable of reacting with selected side chains or the N- or C-terminal residues. Another type of covalent modification of the heteromultimeric protein comprises altering the native glycosylation pattern of the polypeptide. For example, one or more carbohydrate moieties found in the original heteromultimeric protein may be deleted, and/or one or more glycosylation sites that are not present in the original heteromultimeric protein may be added. Addition of glycosylation sites to the heteromultimeric protein is conveniently accomplished by altering the amino acid sequence such that it contains one or more N-linked glycosylation sites. The alteration may also be made by the addition of, or substitution by, one or more serine or threonine residues to the original heteromultimeric protein sequence (for O-linked glycosylation sites). For example, the amino acid sequences of the heteromultimeric protein may be altered through changes at the DNA level, e.g., by mutating the DNA encoding the heteromultimeric protein at preselected bases such that codons are generated that will translate into the desired amino acids. Another means of increasing the number of carbohydrate moieties on the heteromultimeric protein is by chemical or enzymatic coupling of glycosides to the polypeptide. These methods are described in WO 87/05330, and in Aplin and Wriston, CRC Crit, Rev. Biochem pp. 259-306 (1981). Removal of carbohydrate moieties present on the heteromultimeric proteins may be accomplished chemically or enzymatically.

Another type of covalent modification of heteromultimeric protein comprises linking the heteromultimeric protein to one of a variety of nonproteinaceous moieties. The moieties suitable for derivatization of the heteromultimeric protein include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the heteromultimeric protein may vary, and if more than one polymer are attached, they can be the same or different molecules. In general, the number and/or type of polymers used for derivatization can be determined based on considerations including, but not limited to, the particular properties or functions of the heteromultimeric protein to be improved, whether the heteromultimeric protein derivative will be used in a therapy under defined conditions, etc.

III. Methods of Preparation

The present application also provides methods of preparing heteromultimeric (e.g., heterodimeric) proteins, such as multispecific antibodies or immunoadhesins. Nucleic acids, vectors, and host cells for preparing the heteromultimeric proteins or polypeptides thereof are also provided.

The heteromultimeric proteins described herein can be prepared using any known methods in the art, including those described below and in the Examples. Such methods may include culturing a host cell comprising nucleic acids encoding the first and second CH3-containing polypeptides such that the polypeptides are co-expressed by the cell. In certain embodiments, the nucleic acids encoding the first and the second CH3-containing polypeptides are provided to the host cell at a ratio, for example, about any one of 1:1, 1:2, 2:1, 1:3, 3:1, 1:4, 4:1, 1:5, 5:1, 1:6, 6:1, 1:7, 7:1, 1:8, 8:1, 1:9, 9:1, 1:10, or 10:1 (molar:molar). In some embodiments, the heteromultimeric protein comprises one or more antibody light chains. In some embodiments, the heteromultimeric protein comprises a first heavy chain, a second heavy chain, and a common light chain that are co-expressed by the cell. In some embodiments, the nucleic acid encoding the common light chain and the nucleic acid encoding the first or second heavy chain are provided to the host cell at a ratio of at least about any one of 1:1, 2:1, 3:1, 4:1, 5:1, 6:1, 7:1, 8:1, 9:1, or 10:1. In some embodiments, the nucleic acid encoding the first heavy chain, the nucleic acid encoding the second heavy chain, and the nucleic acid encoding the common light chain are provided to the host cell at a ratio of about 1:1:5. It is contemplated that altering the ratio of nucleic acids may increase the production of heterodimeric molecules versus homodimeric molecules.

In some embodiments, there is provided a method of generating a heteromultimeric protein that specifically binds to a first target and a second target, comprising: (a) providing a first polypeptide comprising a first binding domain that specifically binds to the first target and a first CH3 domain; and (b) providing a second polypeptide comprising a second binding domain that specifically binds to the second target and a second CH3 domain; wherein: (i) the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid; or (ii) the first CH3 domain comprises a substitution relative to a wildtype CH3 domain at amino acid position 347 with a negatively charged amino acid, and/or the second CH3 domain comprises a substitution relative to a wildtype CH3 domain at amino acid position 354 with a bulky hydrophobic amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains. In some embodiments, the substitution at amino acid position 354 is S354Y. In some embodiments, the substitution at amino acid position 347 is Q347E. In some embodiments, the first CH3 domain and the second CH3 domain further comprises KIH residues, such as T366Y or Y407T.

In some embodiments, there is provided a method of generating a multispecific antibody that specifically binds to a first target and a second target, comprising: (a) providing a first heavy chain comprising from the N-terminus to the C-terminus: a VH1, a first CH1, a first CH2, and a first CH3 domain; (b) providing a first light chain comprising from the N-terminus to the C-terminus: a VL1 and a CL; (c) a second heavy chain comprising from the N-terminus to the C-terminus: a VH2, a second CH1, a second CH2, and a second CH3 domain; and (d) a second light chain comprising from the N-terminus to the C-terminus: a VL2 and a second CL; wherein VH1 and VL1 associate to form a first antigen binding site that specifically binds to the first target, and VH2 and VL2 associate to form a second antigen binding site that specifically binds to the second target; wherein: (i) the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid; or (ii) the first CH3 domain comprises a substitution relative to a wildtype CH3 domain at amino acid position 347 with a negatively charged amino acid, and/or the second CH3 domain comprises a substitution relative to a wildtype CH3 domain at amino acid position 354 with a bulky hydrophobic amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In sonic embodiments, the first and second CH3 domains are human CH3 domains. In some embodiments, the substitution at amino acid position 354 is S354Y. In some embodiments, the substitution at amino acid position 347 is Q347E. In some embodiments, the first CH3 domain and the second CH3 domain further comprises KIH residues, such as T366Y or Y407T. In some embodiments, VL1 and VL2 have the same amino acid sequence. In some embodiments, VL1 and VL2 have different amino acid sequences.

Nucleic Acids

The present application further provides isolated nucleic acid molecules comprising polynucleotides that encode one or more polypeptide chains of the heteromultimeric proteins (such as multispecific antibodies) described herein.

Oligonucleotide-mediated mutagenesis can be used to prepare substitution variants of the DNA encoding the first or second polypeptide. This technique is well known in the art as described by Adelman et al., DNA, 2: 183 (1983). Briefly, first or second polypeptide DNA is altered by hybridizing an oligonucleotide encoding the desired mutation to a DNA template, where the template is the single-stranded form of a plasmid or bacteriophage containing the unaltered or native DNA sequence of heteromultimer. After hybridization, a DNA polymerase is used to synthesize an entire second complementary strand of the template that will thus incorporate the oligonucleotide primer, and will code for the selected alteration in the heteromultimer DNA. Cassette mutagenesis can be performed as described Wells et al., Gene 34: 315 (1985) by replacing a region of the DNA of interest with a synthetic mutant fragment generated by annealing complimentary oligonucleotides. PCR mutagenesis is also suitable for making variants of the first or second polypeptide DNA.

In some embodiments, a nucleic acid molecule comprises a polynucleotide that encodes the first polypeptide or the second polypeptide of the heteromultimeric protein. In some embodiments, a nucleic acid molecule comprises both a polynucleotide that encodes the first polypeptide and a polynucleotide that encodes the second polypeptide of the heteromultimeric protein. In some embodiments, a nucleic acid molecule comprises a polynucleotide that encodes a heavy chain or a light chain of the multispecific antibody. In some embodiments, a nucleic acid molecule comprises polynucleotides that encode the heavy chains and the light chain(s) of the multispecific antibody. In some embodiments, a first nucleic acid molecule comprises a first polynucleotide that encodes a first heavy chain, a second nucleic acid molecule comprises a second polynucleotide that encodes a second heavy chain, and a third nucleic acid molecule comprises a third polynucleotide that encodes a common light chain. In some embodiments, the nucleic acid molecule(s) are operably linked to a promoter. In some embodiments, different nucleic acid molecules are operably linked to different promoters.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence, which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, a polynucleotide encoding the first polypeptide and/or the second polypeptide and/or the light chain(s) of heteromultimeric protein comprises a nucleotide sequence that encodes a leader sequence, which, when translated, is located at the N terminus of the first polypeptide and/or the second polypeptide and/or the light chain(s). The leader sequence may be the native heavy or light chain leader sequence, or may be another heterologous leader sequence. In some embodiments, the nucleic acid (or a set of nucleic acids) encoding the heteromultimeric protein may further comprises a nucleic acid sequence encoding a peptide tag (such as protein purification tag, e.g., His-tag, HA tag).

The present application also includes variants to these nucleic acid sequences. For example, the variants include nucleotide sequences that hybridize to the nucleic acid sequences encoding any one of the heteromultimeric proteins described herein under at least moderately stringent hybridization conditions.

Nucleic acid molecules may be constructed using recombinant DNA techniques conventional in the art. In some embodiments, a nucleic acid molecule is an expression vector that is suitable for expression in a selected host cell.

Vectors

Vectors comprising polynucleotides that encode the first polypeptide, the second polypeptide, and/or light chain(s) of any one of the heteromultimeric proteins (such as multispecific antibodies) described herein are provided. Such vectors include, but are not limited to, DNA vectors, phage vectors, viral vectors, retroviral vectors, etc.

In some embodiments, a vector comprises a first polynucleotide sequence encoding the first polypeptide, and a second polynucleotide sequence encoding the second polypeptide. In some embodiments, the first polypeptide and the second polypeptide are expressed from the vector as two separate polypeptides. In some embodiments, the first polypeptide and the second polypeptide are expressed as part of a single polypeptide.

In some embodiments, a vector comprises a first polynucleotide sequence encoding a first heavy chain, a second polynucleotide sequence encoding a second heavy chain, and a third polynucleotide sequence encoding a common light chain. In some embodiments, the heavy chains and light chain(s) are expressed from the vector as separate polypeptides. In some embodiments, the heavy chains and light chain(s) are expressed as part of a single polypeptide.

In some embodiments, a first vector comprises a polynucleotide that encodes the first polypeptide and a second vector comprises a polynucleotide that encodes the second polypeptide. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193), The expression of the heteromultimeric protein by nucleic acid(s) encoding the polypeptides can be achieved by inserting the nucleic acid into an appropriate expression vector, such that the nucleic acid is operably linked to 5' and 3' regulatory elements, including for example a promoter and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

In some embodiments, a vector is selected that is optimized for expression of polypeptides in CHO or CHO-derived cells, or in NSO cells. Exemplary such vectors are described, e.g., in Running, Deer et al., *Biotechnol. Prog.* 20:880-889 (2004).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Host Cells

The present application provides isolated host cells comprising any one of the heteromultimeric proteins (such as multispecific antibodies), nucleic acid molecules, or vectors described herein.

The heteromultimeric proteins (such as multispecific antibodies) described herein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. Suitable non-mammalian host cells include prokaryotes as *E. coli* or *B. subtillis*) and yeast (such as *S. cerevisaes, S. pombe*; or *K. lactis*). In some embodiments, a particular eukaryotic host cell is selected based on its ability to make desired post-translational modifications to the heavy chains and/or light chains of the antibody. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

In some embodiments, the heteromultimeric proteins is produced in a cell-free system. Non-limiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

Purification

The heteromultimeric proteins may be purified from the host-cell culture using standard techniques. The heteromultimeric protein may be recovered from the culture medium as a secreted protein, although it also may be recovered from host cell lysate when directly produced without a secretory signal. If the heteromultimeric protein is membrane-bound, it can be released from the membrane using a suitable detergent solution.

When the heteromultimeric protein is produced in a recombinant cell other than one of human origin, it is completely free of proteins or polypeptides of human origin. However, it is necessary to purify the heteromultimeric protein from recombinant cell proteins or polypeptides to obtain preparations that are substantially homogeneous as to heteromultimeric protein. As a first step, the culture medium or lysate is normally centrifuged to remove particulate cell debris.

Heteromultimeric proteins having antibody constant domains can be conveniently purified by hydroxylapatite chromatography, gel electrophoresis, dialysis, or affinity chromatography. Other purification techniques include but are not limited to chromatographic methods such as size exclusion, ion exchange (e.g., MonoQ), hydrophobic interactive chromatography, mixed-mode chromatography (e.g. reversed phase/anion exchange, reversed phase/cation exchange, hydrophilic interaction/anion exchange, hydrophilic interaction/cation exchange, etc.), chromatography on silica, chromatography on heparin Sepharose, chromatography on an anion or cation exchange resin (such as a polyaspartic acid column), reverse phase HPLC, ultracentrifugation, ethanol precipitation, chromatofocusing, SDS-PAGE, and ammonium sulfate precipitation. Suitable affinity ligands include ligands that bind antibody constant regions. For example, a Protein A, Protein G, Protein A/G, or an antibody affinity column may be used to bind the constant region and to purify an antibody comprising an Fc fragment. In some embodiments, the heteromultimeric protein is purified using protein A beads followed by a MonoQ column.

IV. Method of Use

The heteromultimeric proteins (e.g., multispecific antibodies) described herein may be useful for treatment and diagnosis.

Also provided herein are compositions (such as pharmaceutical compositions) comprising any one of the heteromultimeric proteins, nucleic acids, vectors, or host cells described herein. In some embodiments, a heteromultimeric protein may be formulated in a pharmaceutical composition that includes one or more pharmaceutically acceptable buffer or excipient. Such pharmaceutical compositions may be administered to an individual in need thereof to treat a disease or condition, to prevent a disease or condition, or to prevent the symptoms of a disease or condition from progressing.

Pharmaceutical compositions of the t heteromultimeric proteins described herein can be obtained by mixing the heteromultimeric proteins having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine, preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized formulations adapted for subcutaneous administration are described in WO97/04801. Such lyophilized formulations may be reconstituted with a suitable diluent to a high protein concentration and the reconstituted formulation may be administered to the individual to be imaged, diagnosed, or treated herein. Pharmaceutical compositions to be used for in vivo administration must be sterile. This is readily accomplished by, e.g., filtration through sterile filtration membranes.

In some embodiments, there is provided a method of treating a disease in an individual in need thereof, comprising administering to the individual an effective amount of a heteromultimeric protein, comprising: (a) a first polypeptide comprising a first binding domain that specifically binds to a first target and a first CH3 domain; and (b) a second polypeptide comprising a second binding domain that specifically binds to a second target and a second CH3 domain; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains. In some embodiments, the substitution at amino acid position 354 is S354Y. In some embodiments, the substitution at amino acid position 347 is Q347E. In some embodiments, the first CH3 domain and the second CH3 domain further comprises KIH residues, such as T366Y or Y407T. In some embodiments, the first target is a tumor antigen (e.g., CD20, HER2 or BCMA) and the second target is CD3, or the first target is CD3 and the second target is a tumor antigen (e.g., CD20, HER2 or BCMA). In some embodiments, the disease is a cancer.

In some embodiments, there is provided a method of treating a disease in an individual in need thereof, comprising administering to the individual an effective amount of a multispecific antibody comprising: (a) a first heavy chain comprising from the N-terminus to the C-terminus: a VH1, a first CH1, a first CH2, and a first CH3 domain; (b.) a first light chain comprising from the N-terminus to the C-terminus: a VL1 and a CL; (c) a second heavy chain comprising from the N-terminus to the C-terminus: a VH2, a second CH1, a second CH2, and a second CH3 domain; and (d) a second light chain comprising from the N-terminus to the C-terminus: a VL2 and a second CL; wherein VH1 and VL1 associate to form a first antigen binding site that specifically binds to a first target, and VH2 and VL2 associate to form a second antigen binding site that specifically binds to a second target; wherein the first CH3 domain comprises a substitution relative to a wildtype CH3 domain at amino acid position 354 with a bulky hydrophobic amino acid, and/or the second CH3 domain comprises a substitution relative to a wildtype CH3 domain at amino acid position 347 with a negatively charged amino acid; and wherein the amino acid residue numbering is based on EU numbering. In some embodiments, the bulky hydrophobic amino acid is Y, F or W. In some embodiments, the negatively charged amino acid is D or E. In some embodiments, the bulky hydrophobic amino acid at amino acid position 354 forms a hydrophobic interaction with an amino acid residue in the second CH3 domain. In some embodiments, the second CH3 domain comprises a bulky hydrophobic residue at amino acid position 349 (e.g., Y349). In some embodiments, the negatively charged amino acid at amino acid position 347 forms an ionic bond with an amino acid residue in the first CH3 domain. In some embodiments, the first CH3 domain comprises a positively charged residue at amino acid position 360 (e.g., K360). In some embodiments, the first and second CH3 domains are human CH3 domains. In some embodiments, the substitution at amino acid position 354 is S354Y. In some embodiments, the substitution at amino acid position 347 is Q347E. In some embodiments, the first CH3 domain and the second CH3 domain further comprises KIH residues, such as T366Y or Y407T. In some embodiments, VL1 and VL2 have the same amino acid sequence. In some embodiments, VL1 and VL2 have different amino acid sequences. In some embodiments, the first target is a tumor antigen (e.g., CD20, HER2 or BCMA) and the second target is CD3, or the first target is CD3 and the second target is a tumor antigen (e.g., CD20, HER2 or BCMA). In some embodiments, the disease is a cancer.

In some embodiments, the heteromultimeric protein is used in a diagnostic assay. For example, the heteromultimeric proteins are useful for sandwich assays which involve the use of two molecules, each capable of binding to a different immunogenic portion, or epitope, of the sample to be detected. In a sandwich assay, the test sample analyte is bound by a first arm of the heteromultimeric protein, which is immobilized on a solid support, and thereafter a second arm of the heteromultimeric protein binds to the analyte, thus forming an insoluble three-part complex. The second arm of the heteromultimeric may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

V. Kits and Articles of Manufacture

Also provided are kits useful for any one of the methods of preparation, diagnosis and treatment described herein, including kits comprising any one of the heteromultimeric proteins (e.g., multispecific antibodies) described herein.

The kits of the present application are in suitable packaging. Suitable packaging includes, but is not limited to, vials, bottles, jars, flexible packaging (e.g., sealed Mylar or plastic bags), and the like. Kits may optionally provide additional components such as reagents, buffers, and interpretative information.

The present application thus also provides articles of manufacture. The article of manufacture can comprise a container and a label or package insert on or associated with the container. Suitable containers include vials (such as sealed vials), bottles, jars, flexible packaging, and the like. In some embodiments, the container holds a pharmaceutical composition, and may have a sterile access port (for example, the container may be an intravenous solution bag or a vial having a stopper pierceable by a hypodermic injection needle). The label or package insert indicates that the composition is used for diagnosing (including determining a risk), treating or preventing a disease or condition in an individual. The label may indicate directions for reconstitution and/or use of the various components. The container holding the pharmaceutical composition may be a multi-use vial, which allows for repeat administrations (e.g. from 2-6 administrations) of the reconstituted formulation. Package insert refers to instructions customarily included in commercial packages of diagnostic and/or therapeutic products that contain information about the indications, usage, dosage, administration, contraindications and/or warnings concerning the use of such products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical compositions and instructions for use, packaged in quantities sufficient for storage and use in pharmacies, for example, hospital pharmacies and compounding pharmacies.

EXAMPLES

The examples below are intended to be purely exemplary of the invention and should therefore not be considered to limit the invention in any way. The following examples and detailed description are offered by way of illustration and not by way of limitation.

Figure 3:
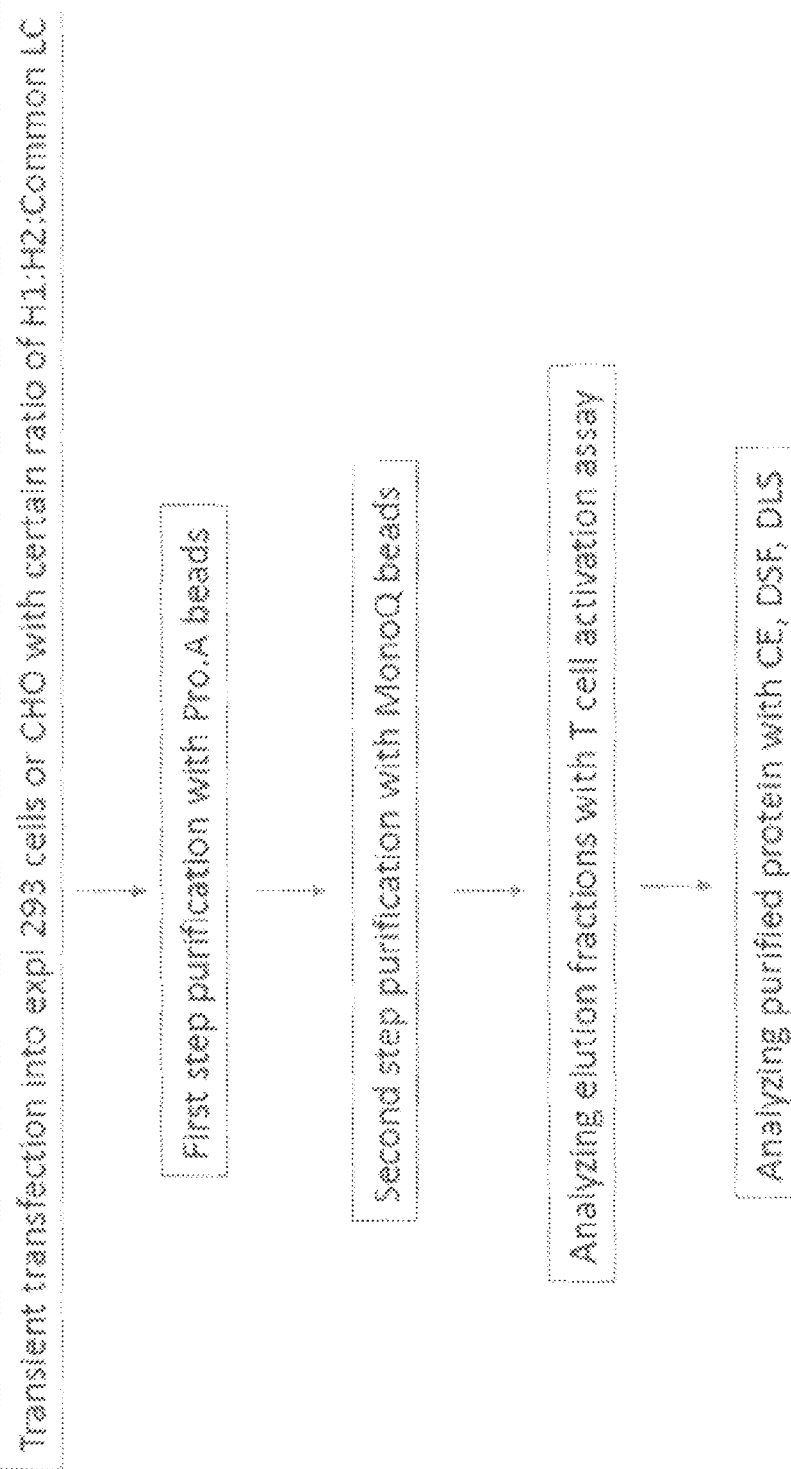
FIG. 3 shows a schematic workflow for the production and quality control of CD20/CD3 bispecific antibody.

Example 1. Production, Purification and Characterization of CD20/CD3 Bispecific Antibody Bispecific CD20/CD3 antibodies were prepared and characterized according to the flow chart of FIG. 3.

In a first format (S1 of FIG. 1), two common light chain CD20/CD3 antibodies were prepared. The V2 CD20/CD3 antibody has KIH residues T366Y in a first heavy chain, and Y407T residue in a second heavy chain. The V4b CD20/CD3 antibody has T136Y and S354Y in a first heavy chain, and Y407T and Q347E in a second heavy chain.

Vectors encoding the heavy chains and light chain were transiently transfected into expi 293 cells or CHO cells with a first heavy chain (HI): second heavy chain (H2): common light chain ratio of 1:1:2 or 1:1:5. Host cells were cultured and induced to secrete the bispecific antibodies. The supernatants of the cell culture, which contained the bispecific antibodies, were centrifuged at 3000 rpm for 10 minutes, and then the supernatant samples were filtered using a 0.45 μm membrane.

The bispecific antibodies were then purified from the supernatant samples using a two-step chromatography protocol, including a first Protein A purification step and a MonoQ step. In the Protein A purification step, the AKTA purification system was first balanced with 10 column volumes (CV) of Buffer A (PBS pH=7.4). The supernatant was loaded onto the Protein A purification column, and the column was washed with Buffer A for 10 CV. The bispecific antibody was eluted with Buffer B (0.1M Glycine pH=2.5), and the peak fractions were collected and combined. The combined antibody sample was dialyzed in PBS twice.

In the MonoQ step, the antibody sample was first exchanged into Buffer A' (20 mM Tris-Cl, pH=9). The AKTA purification system was then balanced with Buffer A'. The antibody sample was loaded onto the MonoQ column, which was subsequently washed with Buffer A' for 5 CV. The bispecific antibody was eluted from the MonoQ column using a salt gradient set up by Buffer A' and Buffer B' (20 mM Tris-Cl, 1M NaCl, pH=9), with 0-25% Buffer B' in 50 minutes, at flow rate of 0.4 ml/min. The peak fractions were collected and combined. The purified bispecific antibody was then buffer exchanged into PBS.

Purified bispecific antibody fractions from the MonoQ column were confirmed using a T-cell activation assay. Briefly, Raji (human B lymphocytes) and Jurkat (human T lymphocytes) cells were each seeded into a 96 well plate at $1\times10^5$ cells/well. Diluted bispecific antibody samples were added to the plates and incubated in a 37° C., 5% $CO_2$ incubator for 17 hours. The plate was washed with PBS with 0.1% BSA once at 1200 rpm for 5 minutes. CD69-PE was then added to the plate and incubated for 30 minutes at room temperature. The plate was subsequently washed with PBS with 0.1% BSA once at 1200 rpm for 5 minutes. CD69+ signals were read from the plate in the FL2 channel on a BD Calibur plate reader.

Figure 4:
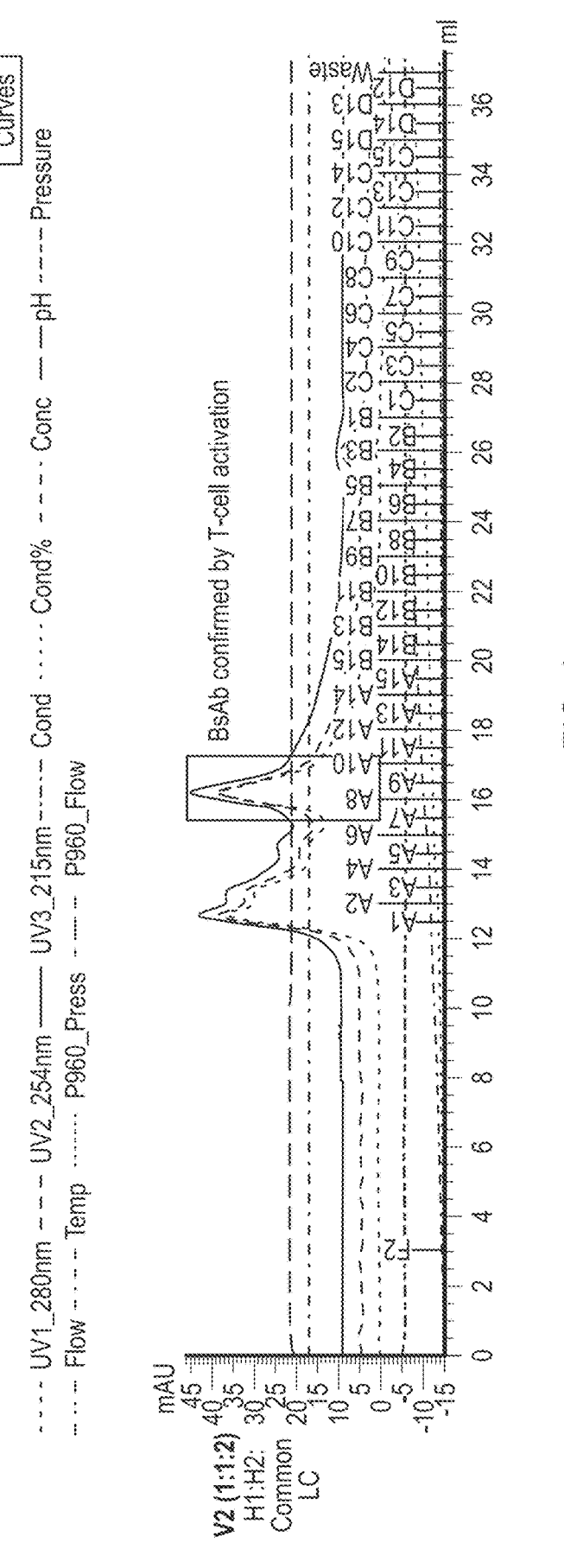
FIG. 4 shows chromatograms of CD20/CD3 antibodies on a MonoQ column following MonoQ purification, V2 is a common light chain bispecific antibody with (i.e., T366Y and Y407T) residues. V4b is a common light chain bispecific antibody with the same KIH residues as V2 plus Q347E and S354Y mutations in the two heavy chains respectively.
Figure 4:
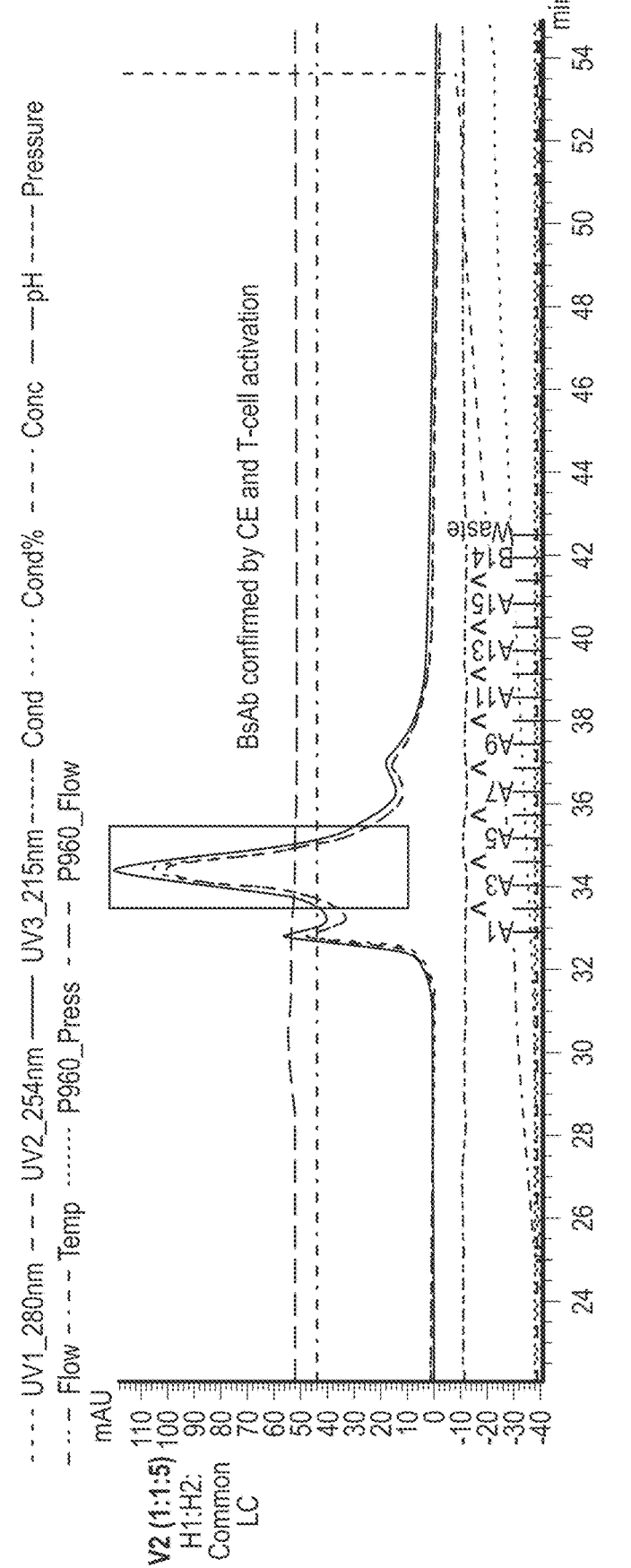
Figure 4:
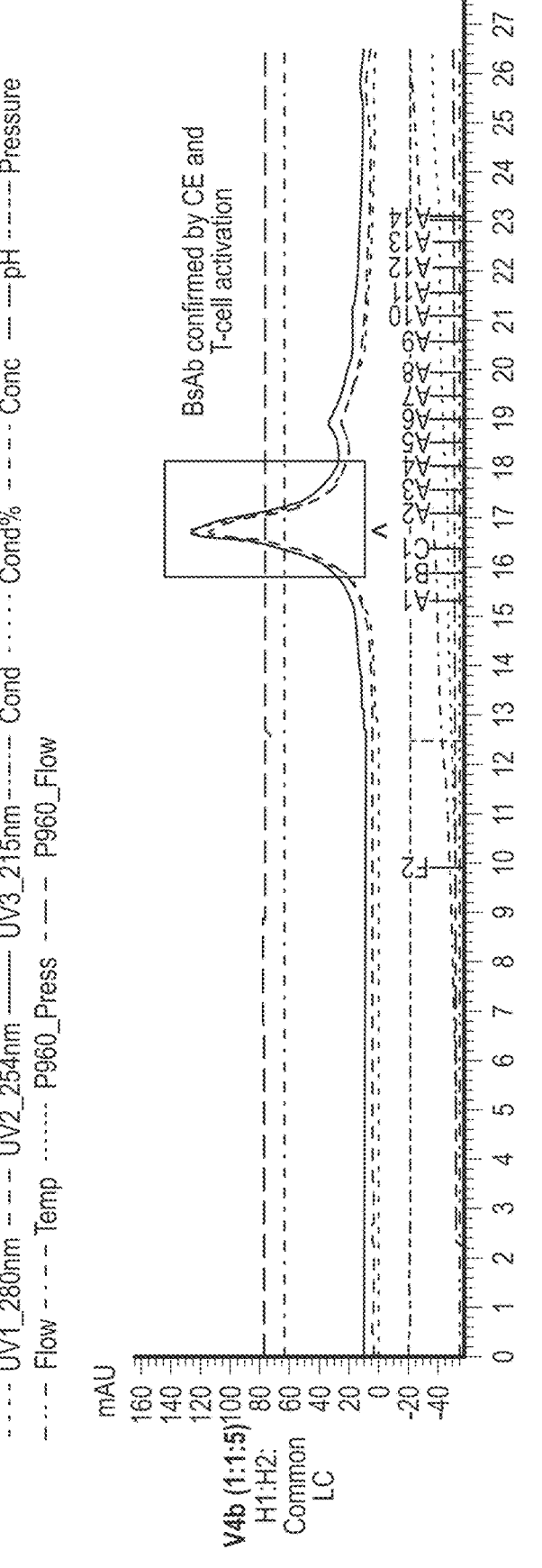
Figure 6:
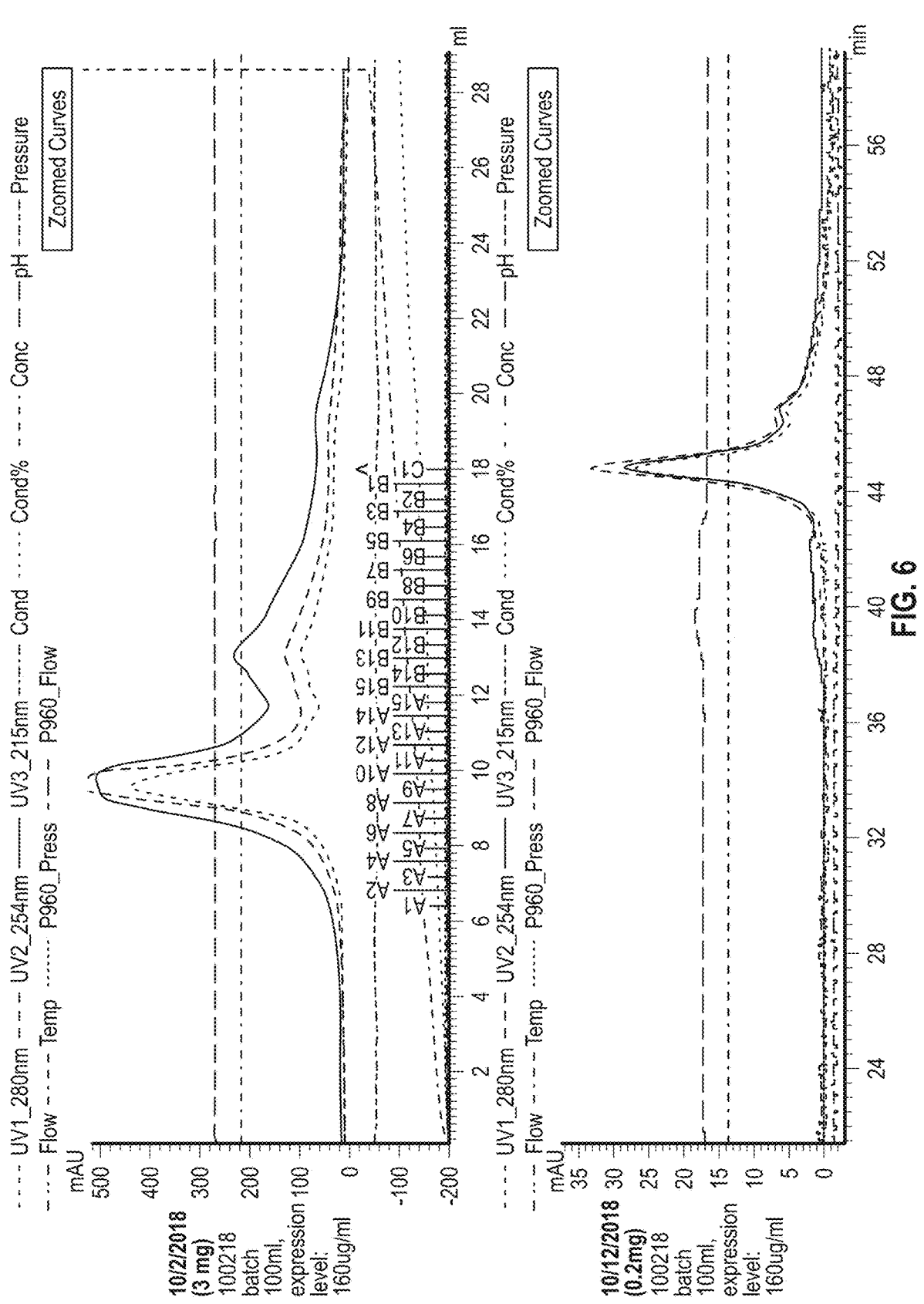
FIG. 6 shows chromatograms of four batches of CD20/CD3 V4b bispecific antibody on a MonoQ column following Protein A purification
Figure 6:
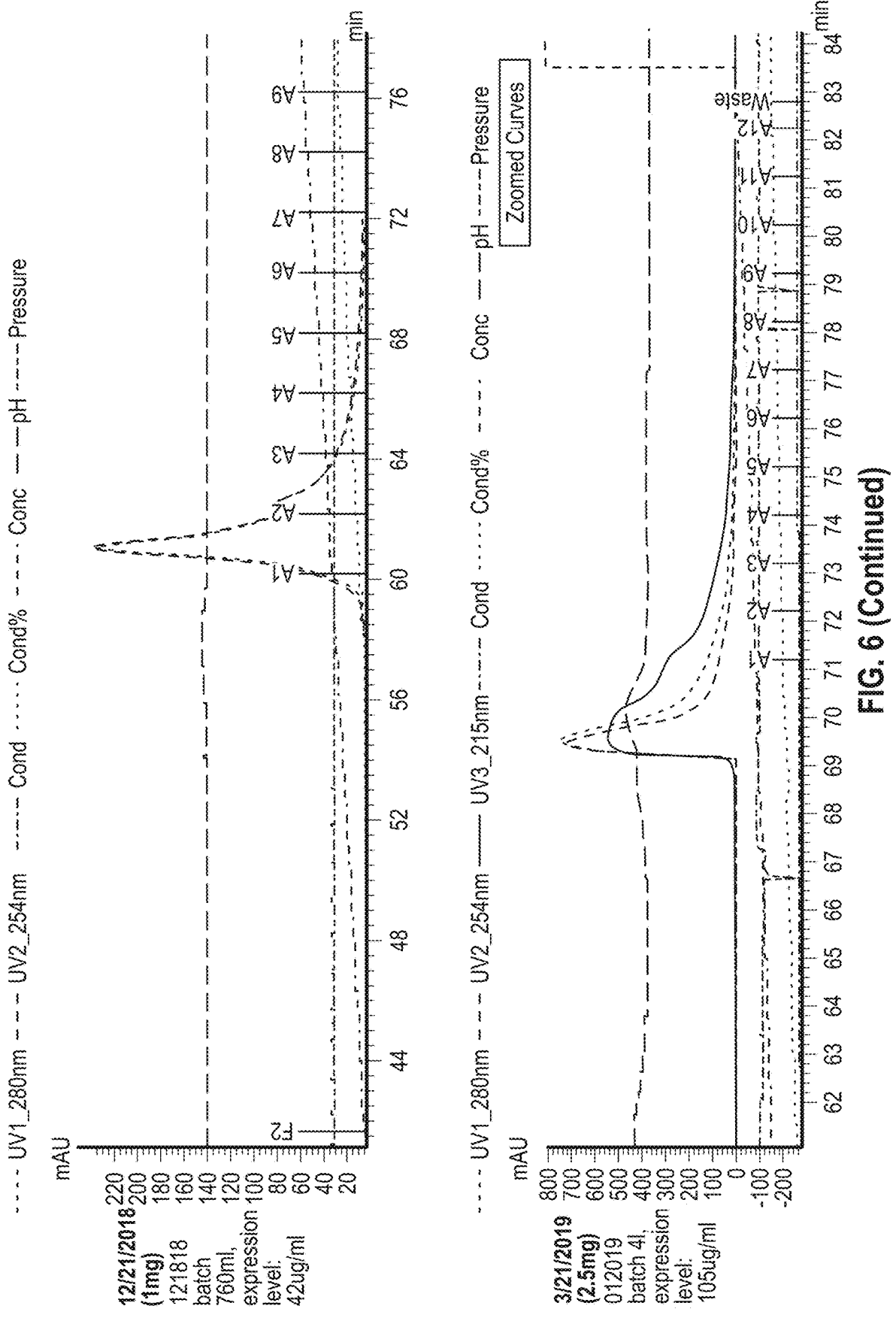
Figure 6:
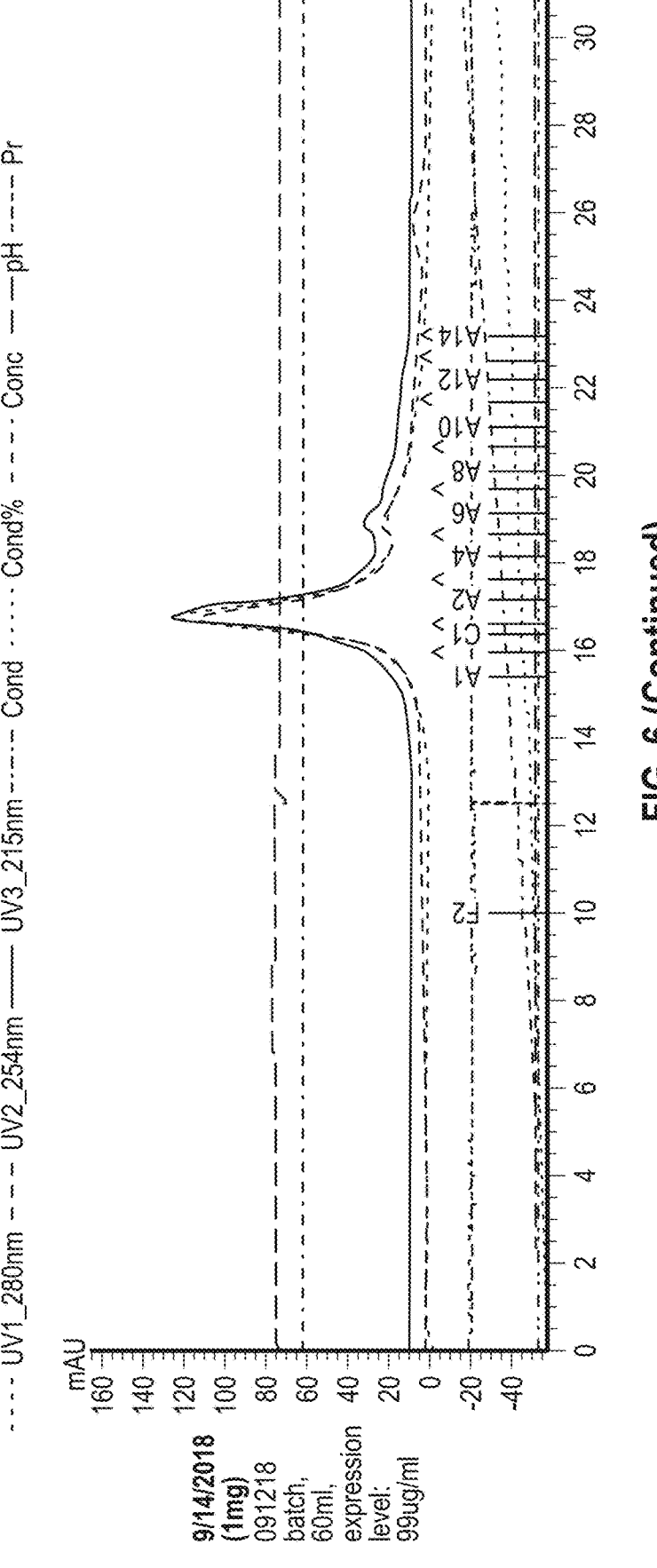

The expression levels and yields from each purification steps for the three batches of CD20/CD3 bispecific antibody are shown in Table 3 below. As a reference, rituximab is expressed at about 130 mg/L from the same expression system. FIG. 4 shows chromatograms from the MonoQ purification step of three CD20/CD3 bispecific antibodies. Introduction of the S354Y and Q349E mutations to the Fc improved the overall yield of the bispecific antibody from 67.8% (KIH mutations only) to 86.8% (KIH S354Y and Q349E). As shown in FIG. 6, the high yield and improved heterodimer formation rate of the V4b construct were reproducible in different batches of bispecific antibody preparation.

TABLE 3

| Expression levels and purification yields of CD20/CD3 bispecific antibodies. | | | |
| --- | --- | --- | --- |
| | CD20/CD3 V2 (1:1:2) | CD20/CD3 V2 (1:1:5) | CD20/CD3 V4b (1:1:5) |
| Expression Level (expi 239, transient transfection) | ~16 mg/L | ~150 mg/L | ~100-160 mg/L |
| Recovery rate after Protein A purification | 80.1% | 79.4% | 90.6% |
| Recovery rate of BsAb peak after anion-exchange column (MonoQ) | 42.7% | 67.8% | 86.8% |

54

Figure 5A:
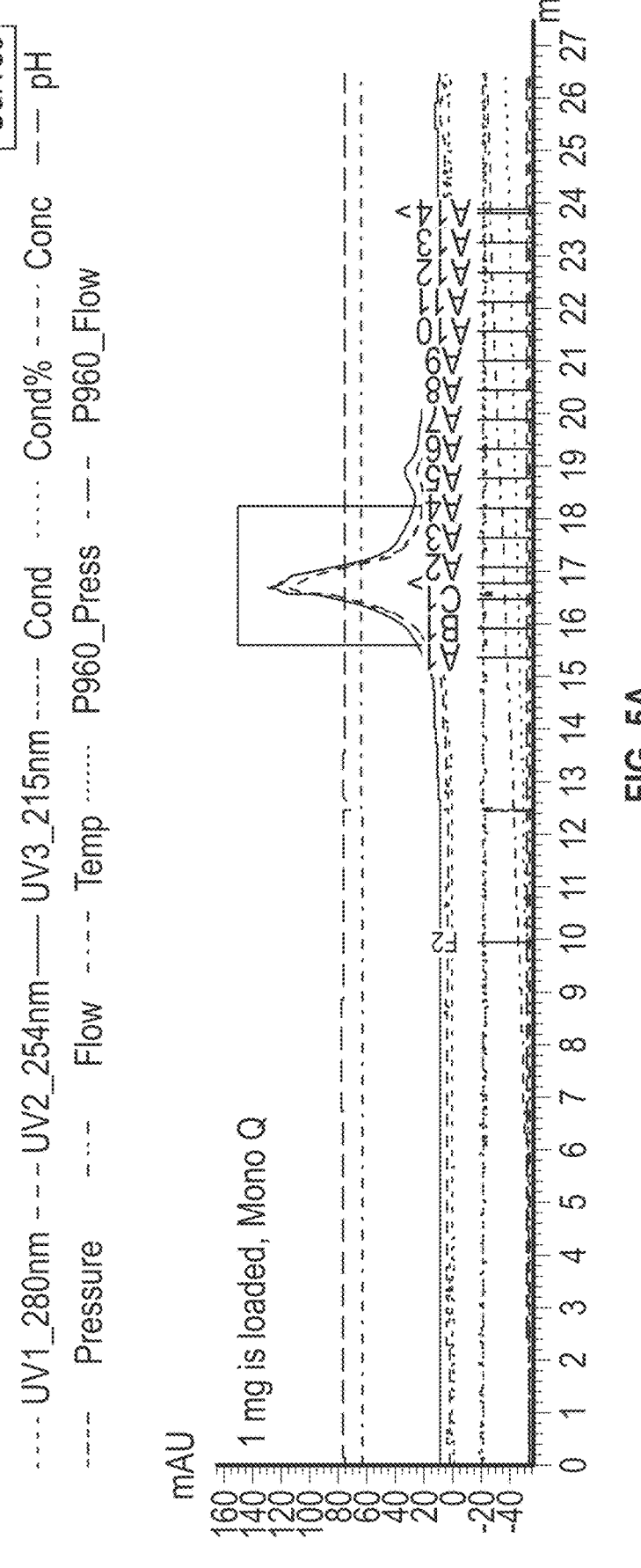
FIG. 5A shows a chromatogram of CD20/CD3 V4b bispecific antibody on a MonoQ column following Protein A purification.
Figure 5B:
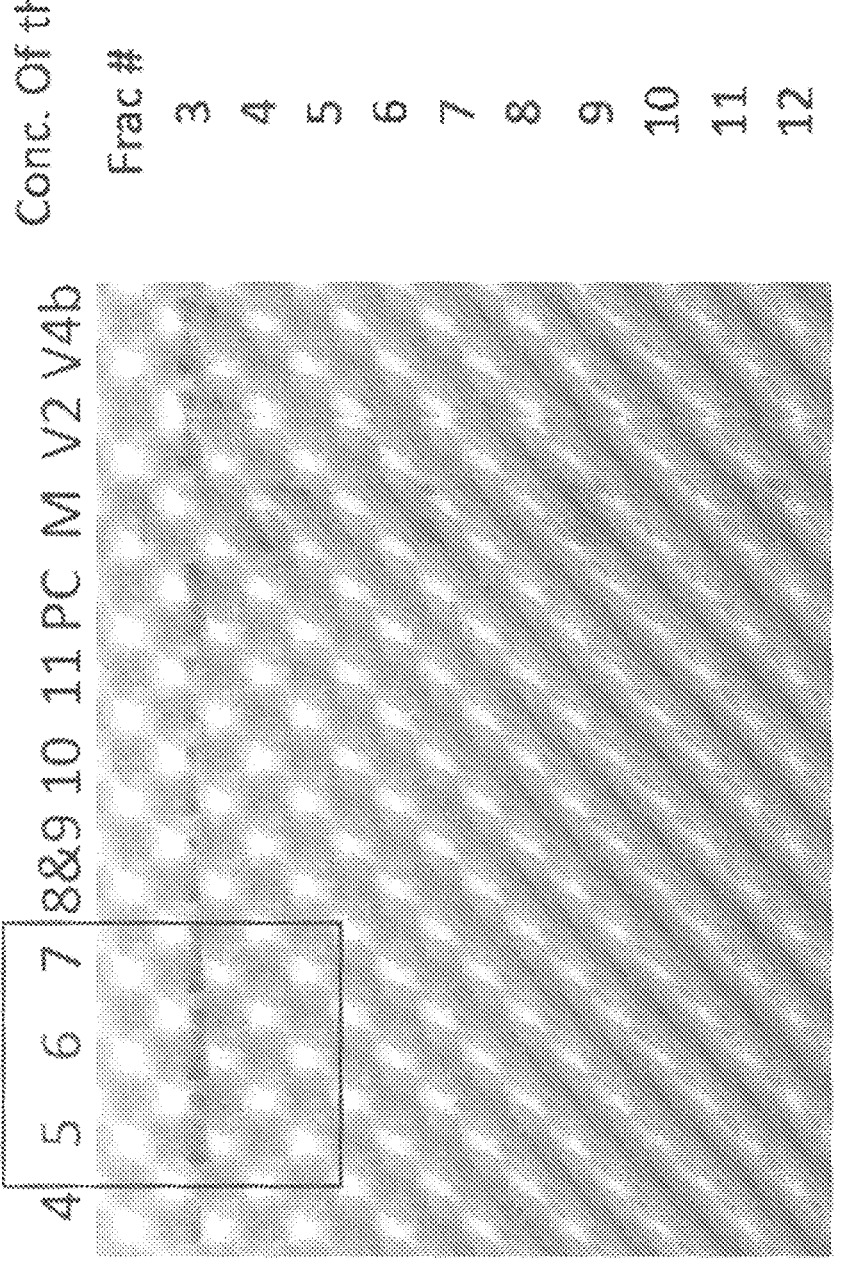
FIG. 5B shows an SDS gel and protein concentrations of the MonoQ purification fractions.
Figure 5C:
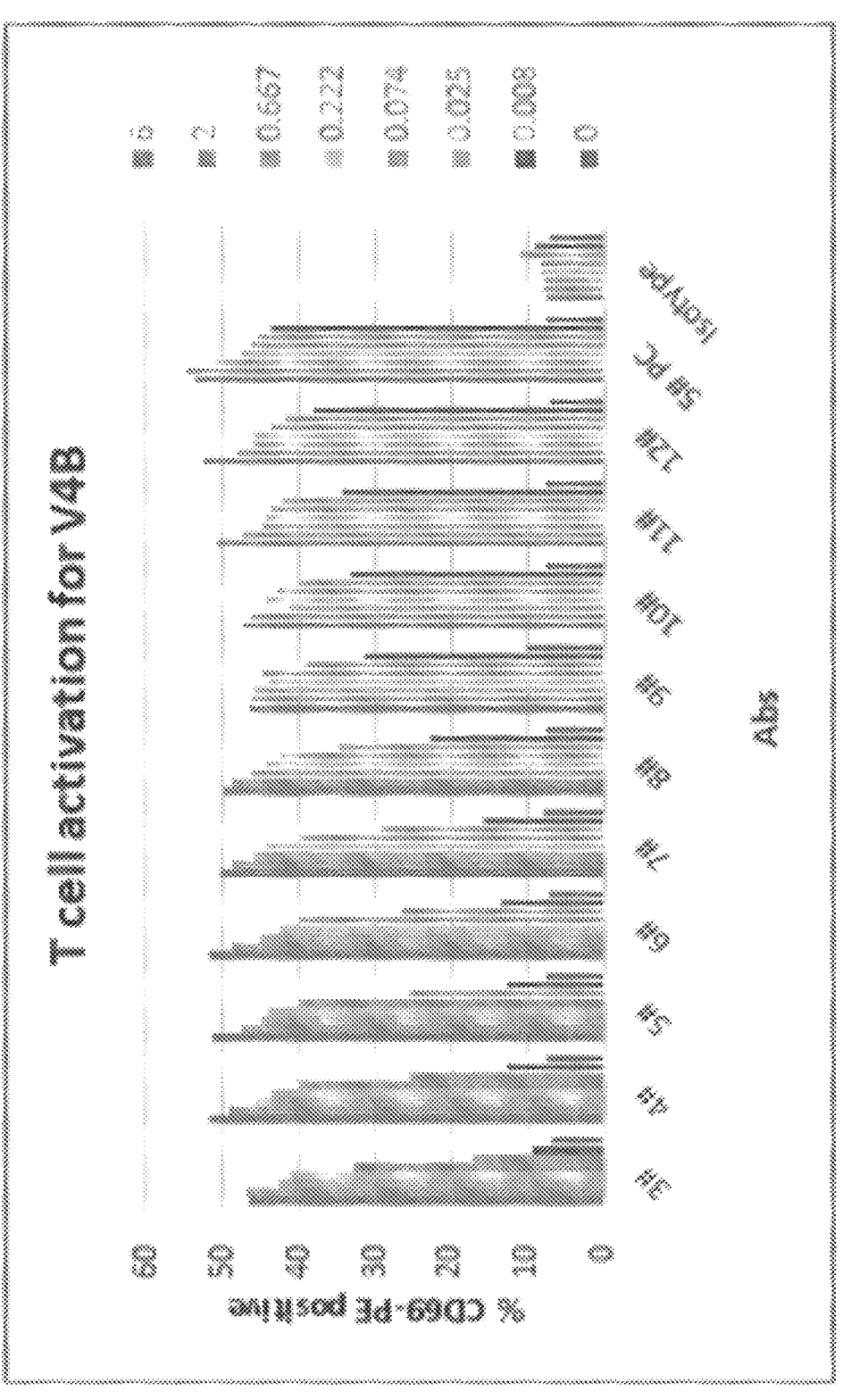
FIG. 5C shows results of a T cell activation assay for the MonoQ purification fractions.
Figure 5D:
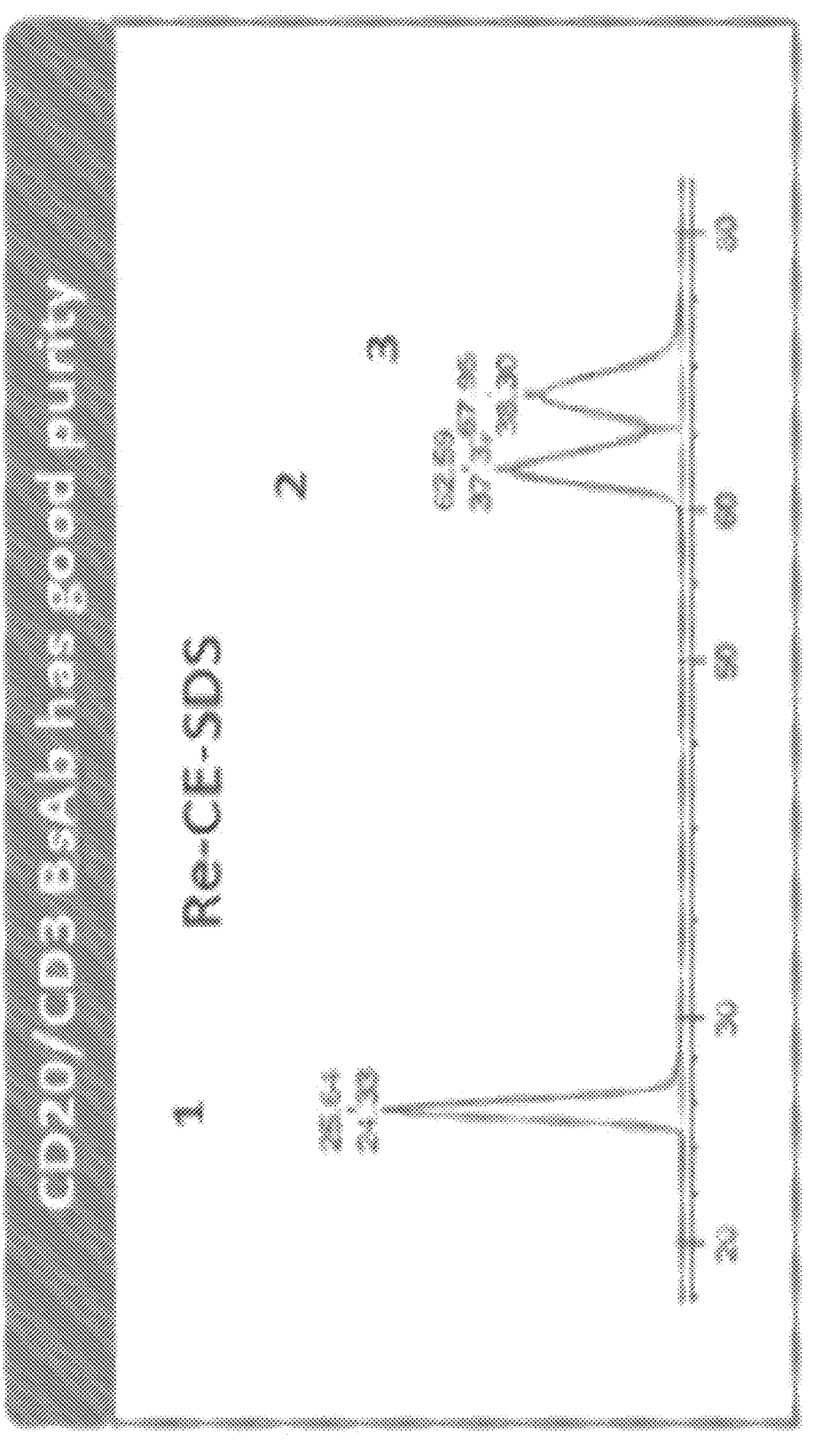
FIG. 5D shows results of capillary electrophoresis sodium dodecyl sulfate (CE-SDS) under reducing conditions for the purified CD20/CD3 V4b bispecific antibody.
Figure 5E:
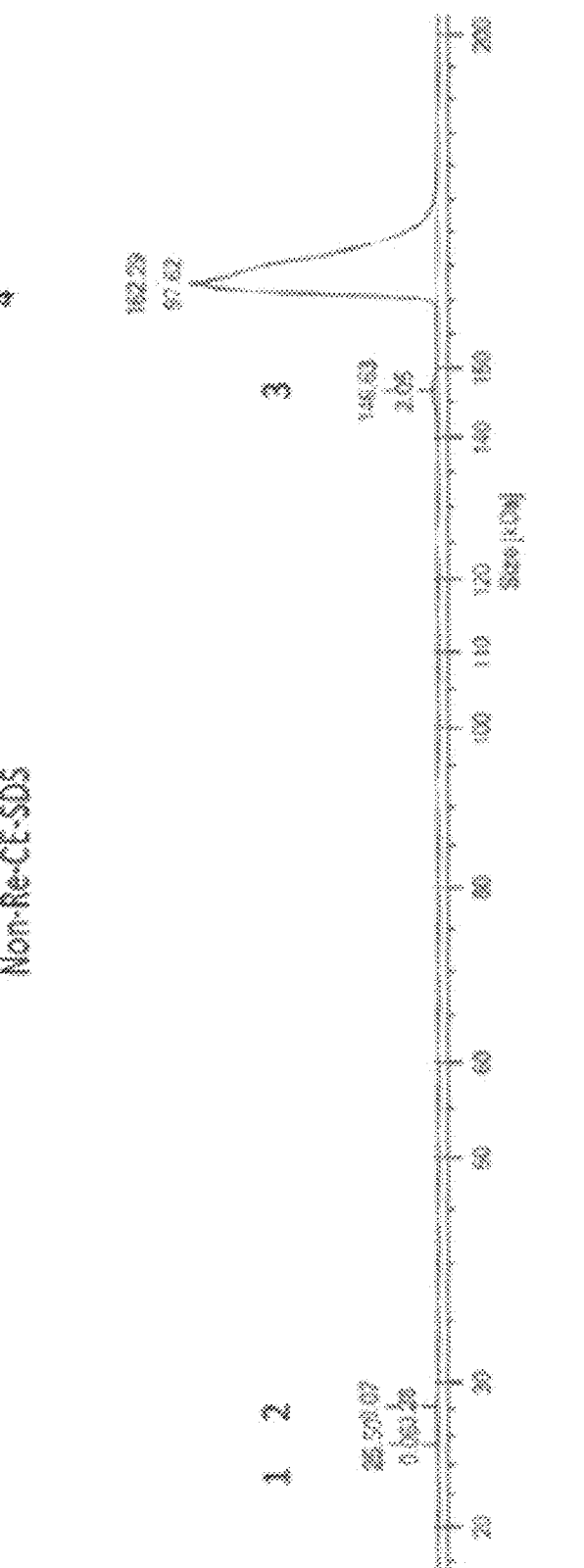
FIG. 5E shows results of CE-SDS under non-reducing conditions for the purified CD20/CD3 V4b bispecific antibody.
Figure 5F:
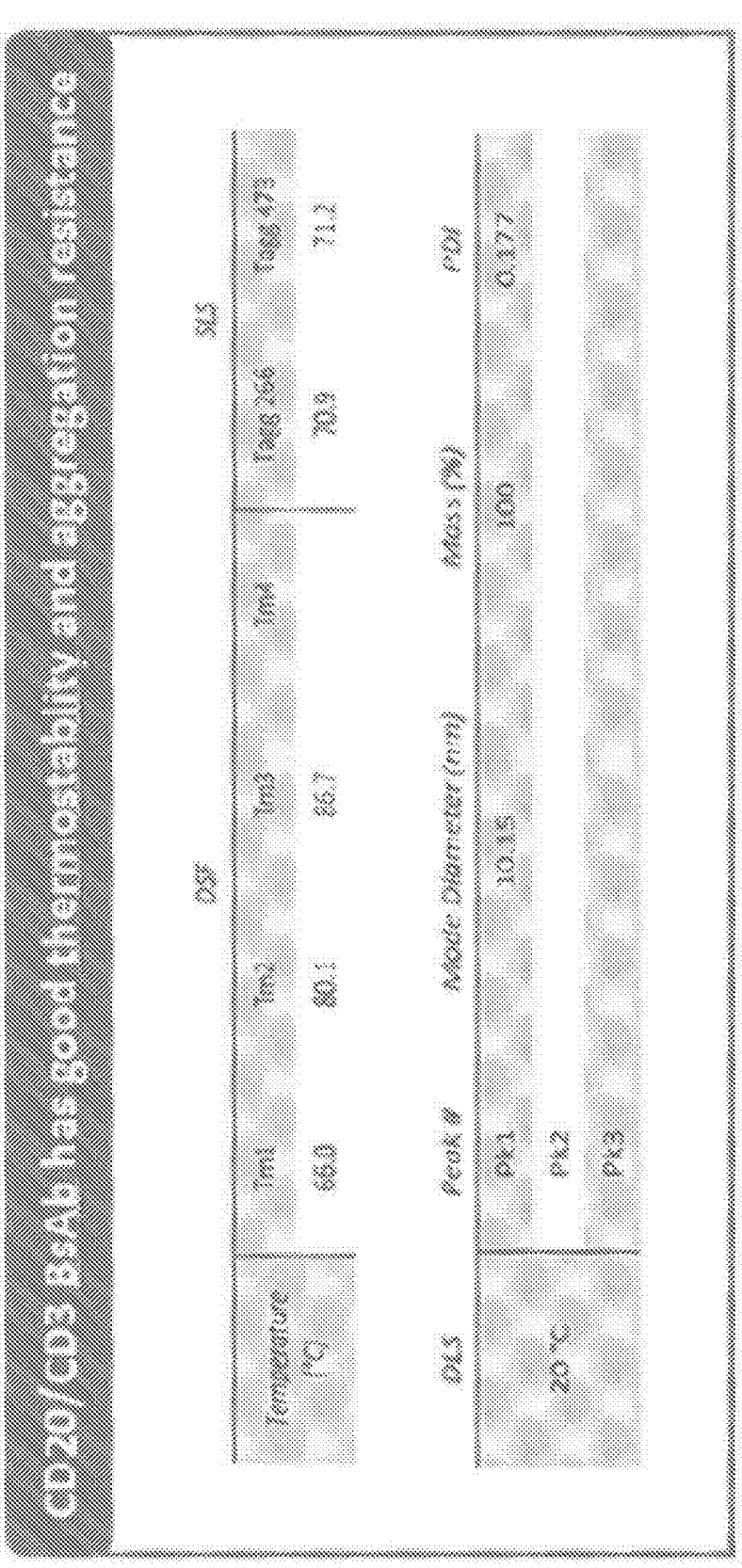
FIG. 5F shows results of differential scanning fluorimetry (DSF) and static light scattering (SLS) for the purified CD20/CD3 V4b bispecific antibody.

Characterization of the purified CD20/CD3 V4b bispecific antibody shows high purity (FIGS. 5B, 5D, 5E), T-cell activation activity (FIG. 5C), thermostability and resistance to aggregation (FIG. 5F).

Figure 8:
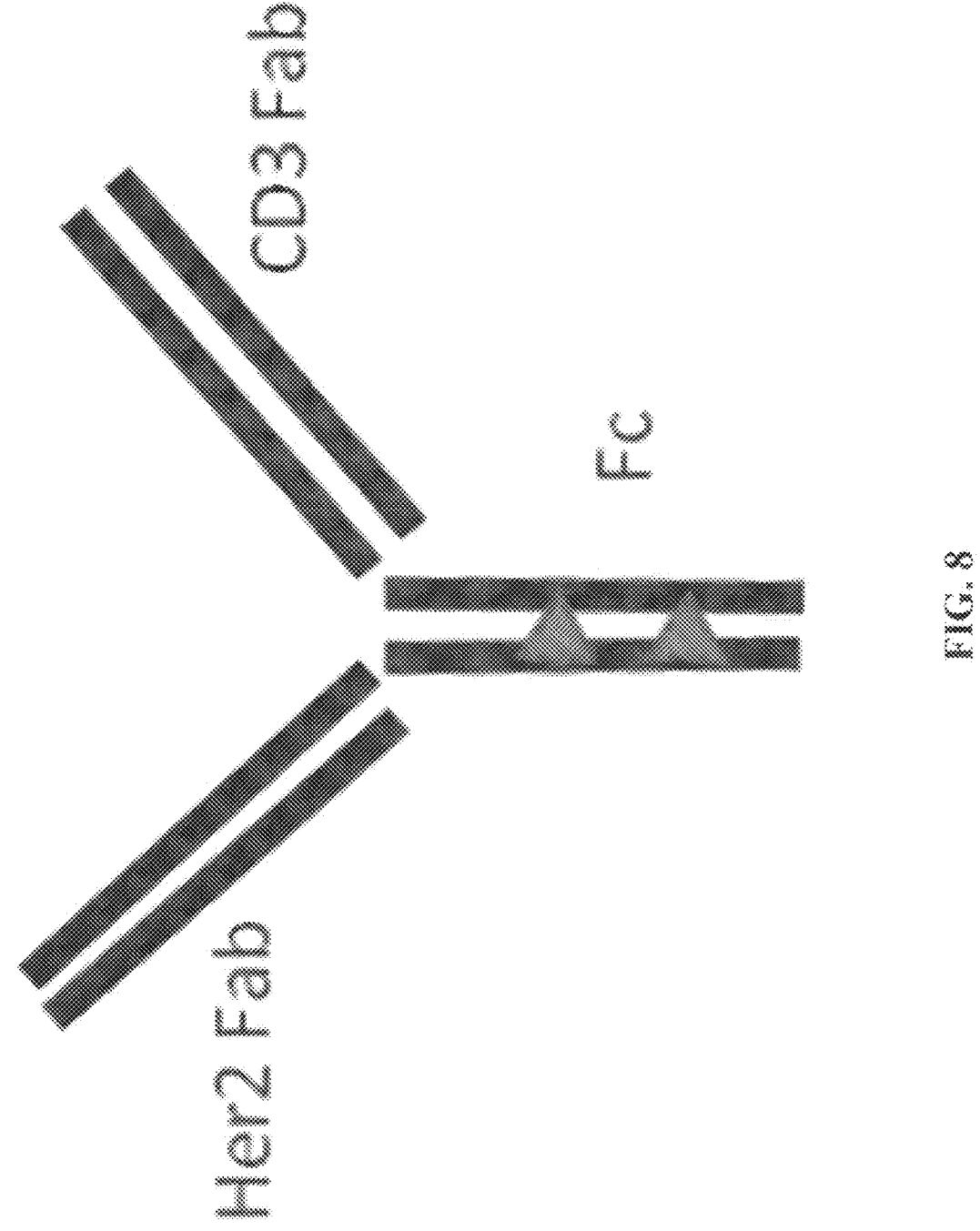
FIG. 8 shows a schematic diagram of the Her2-B3/CD3 bispecific antibody comprising one anti-Her2 Fab, one anti-CD3 Fab, and one Fc domain.
Figure 9:
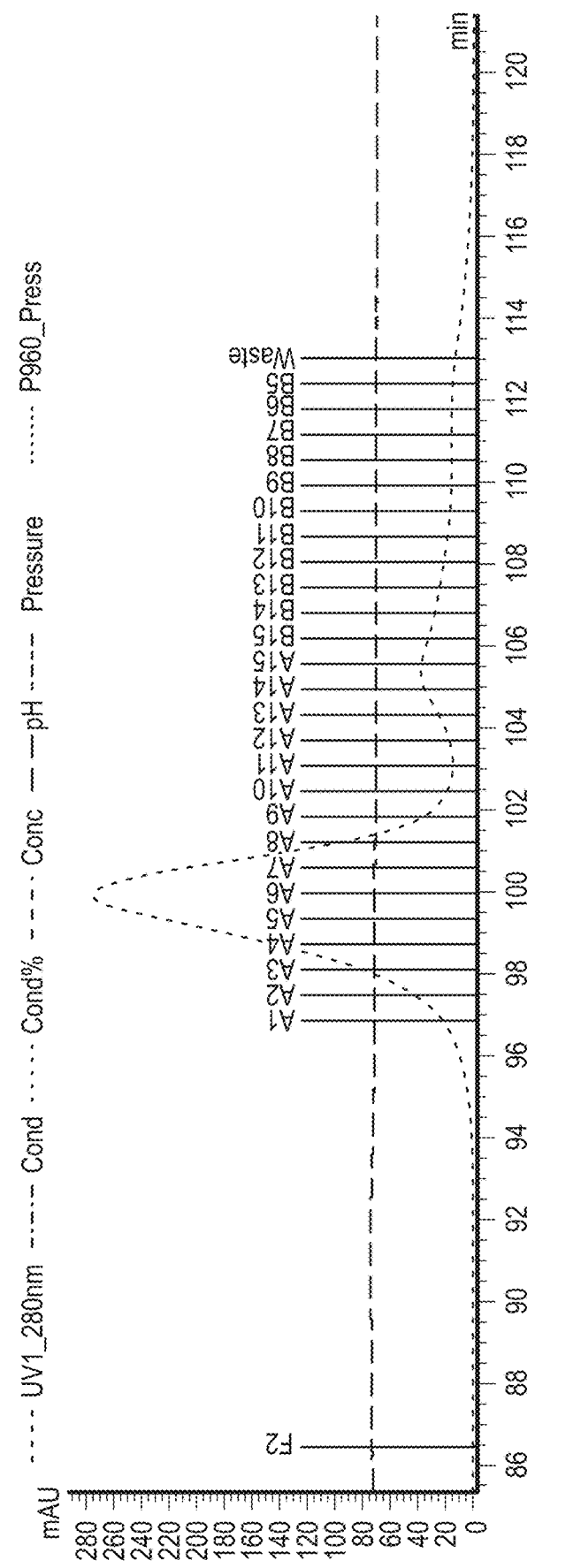
FIG. 9 shows the purification of Her2-B3/CD3 bispecific antibody by cation-exchange chromatography (CEX). Retention time is shown on the x-axis in minutes, and relative protein abundance is shown on the y-axis in milli absorbance units (mAU). Individual peak fractions are labeled (i.e., A1-A15 and B15-B6).
Figure 10:
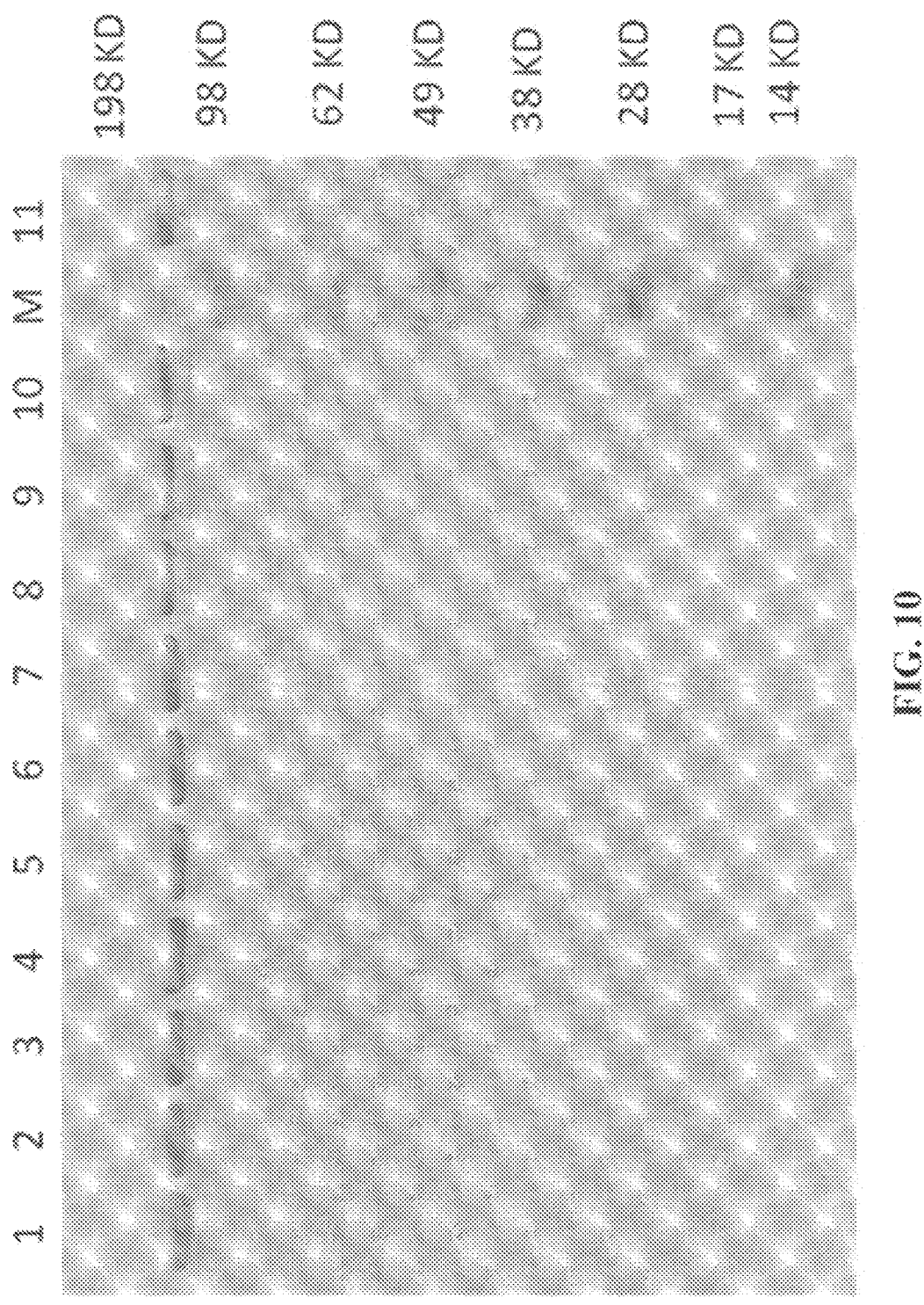
FIG. 10 shows sodium dodecyl sulfate-polyacrylamide gel electrophoresis (SDS-PAGE) of fractions of Her2-B3/CD3 bispecific antibody purified by CEX, as shown in FIG.

Example 2. Production, Purification and Characterization of Her2/CD3 Bispecific Antibody Her2/CD3 Bispecific Antibodies Comprising One Anti-Her2 Fab Her2/CD3 bispecific antibodies comprising one anti-Her2 Fab, one anti-CD3 Fab, and one Fc domain ("Her2-B3/CD3 BsAb", FIG. 8) were prepared by co-transfection of expi 293 cells with plasmids expressing Her2-b3 HC-v4b-knob, CD3-F1C-v4b-hole, and the common light chain. The expression level was determined to be 152 ug/ml at 96 hours after transfection. Culture supernatants were collected, and IgGs were purified on Protein A columns. The purified samples were then loaded onto a cation exchange chromatography column (CEX). After gradient elution, the bispecific antibodies appeared as the main peak detected by CEX (FIG. 9), The purified fractions were further analyzed by sodium dodecyl sulfatepolyacrylamide gel electrophoresis (SDS-PAGE). SDS-PAGE results showed relatively high purity of the fractions from the main CEX peak (FIG. 10).

Her2/CD3 Bispecific Antibodies Comprising Two Anti-Her2 Fabs

Her2/CD3 bispecific antibodies comprising two anti-Her2 Fabs ("Her2-B3-V3/CD3") were prepared (FIG. 11).

An anti-tumor antigen arm of a bispecific antibody with high affinity to tumor cells can often kill healthy non-tumor cells that express normal levels of the antigen. To eliminate this kind of off-tumor effect, a new format of bispecific antibody was developed in which the tumor-targeting arm has two copies of Fab domain, and as a result, becomes bivalent to the tumor antigen (FIG. 11). In this Tri-Domain Bispecific (TDB) format (2:1), the tumor-binding region has a relatively low affinity to the tumor antigen, so it will bind more weakly to the healthy cells that have a lower tumor antigen density.

Expi 293 cells were co-transfected with plasmid expressing Her2 (2 Fabs)-CH-v4b-knob, CD3-CH-v4b-hole, and the common light chain DNA. Culture media was collected, and the expression level was determined using ProbeLife to be 158 ug/ml at 96 hours after transfection. The bispecific antibody Her2-B3-V3/CD3 was purified with a Protein A column. The purified sample was then loaded onto a cation exchange column (CEX) for a second purification. After gradient elution, the bispecific antibody appeared as the main peak (FIG. 12). The purified fractions were further analyzed by SDS-PAGE (FIG. 13). The non-reduced SDS-PAGE results indicated that only one band with the size of about 200 kD is shown after CEX purification, which is consistent with the size of Her2-B3-V3/CD3 (with two Her2 Fabs). The reduced SDS-PAGE results clearly indicated the three chains of the bispecific antibody, which were also consistent with their corresponding sizes.

Example 3. Production, Purification and Characterization of BCMA/CD3 Bispecific Antibody BCMA/CD3 bispecific antibodies were prepared. An anti-BCMA VHH, panned from a llama phage library, was linked to human Fc-v4b-knob, forming a BCMA-Fc chain. The BCMA-Fc chain, together with CD3-HC-v4b-hole and its light chain, formed the new IgG-like bi-specific antibody.

Schematic diagrams of two BCMA/CD3 IgG-like bispecific antibodies are shown in FIG. 14. At left in FIG. 14 is BCMA-3E5/CD3, comprising only one BCMA-VHH (3E5). At right in FIG. 14 is BCMA-3E1B2/CD3, comprising two BCMA-VHHs (3E1 and 392).

To prepare BCMA/CD3 bispecific antibodies, expi 293 cells were co-transfected with plasmids expressing BCMA (3E5)-Fc-v4b-knob (or BCMA (3E1B2)-Fc-v4b-knob), CD3-CH-v4b-hole, and CD3 LC. The culture media was collected, and the expression level was determined using ProbeLife to be 62 ug/ml for BCMA-3E5/CD3, and 54 ug/ml for BCMA-3E1B2/CD3.

The cultured supernatant was collected, and the two bispecific antibodies were purified on Protein A columns. SDS-PAGE was performed for the two BCMA-Fc/CD3 bispecific antibodies (FIG. 15), The results indicated that both BCMA/CD3 bispecific antibodies were successfully expressed, and that there was some CD3 homodimer formation (about 150 Kd in size; see FIG. 15). In the reduced SDS-PAGE results CD3-VH-v4b-hole, BCMA-Fc, and the common light chain were detected based on their molecular weights (FIG. 15).

Further experiments are performed to purify and characterize BCMA/CD3 bispecific antibodies. First, the ratio of the three plasmids expressing the three chains in the transfection is optimized. Optimization of the ratio of the three plasmids increases the percentage of bispecific antibody heterodimer. With the optimized ratio of plasmids, BCMA/CD3 bispecific antibodies are expressed and purified on a Protein A column and by CEX. BCMA/CD3 bispecific antibody purity is assessed by SDS-PAGE.

Example 4. Production, Purification and Characterization of CD20/CD3 Bispecific Antibody with Fc Mutations CD20/CD3 bispecific antibodies with mutations in the Fc region were generated. Mutations to the anti-CD20 heavy chain are shown in Table 4. Mutations to the anti-CD3 heavy chain are shown in Table 5.

TABLE 4

| | | | | Anti-CD20 heavy chain Fc mutations. | | | | | |
|---|---|---|---|---|---|---|---|---|---|
| | | Mutation | Template | T366Y (knob) | S354Y | S354D | S354K | S354F | S354W |
| A1 | CD20_K-S354Y | NA | NA | * | * | | | | |
| A2 | CD20_S354Y | Y366T | CD20_K-S354Y (A1) | | * | | | | |
| A3 | CD20_WT | Y354S | CD20_S354Y (A2) | | | | | | |
| A4 | CD20_S354D | S354D | CD20_WT (A3) | | | * | | | |
| A5 | CD20_S354K | S354K | CD20_WT (A3) | | | | * | | |
| A6 | CD20_K-S354F | Y354F | CD20_K-S354Y (A1) | * | | | | * | |
| A7 | CD20_K-S354W | Y354W | CD20_K-S354Y (A1) | * | | | | | * |
| A8 | CD20_Knob | Y354S | CD20_K-S354Y (A1) | * | | | | | |

TABLE 5

| | | | | Anti-CD3 heavy chain Fc mutations. | | | | | | | |
|---|---|---|---|---|---|---|---|---|---|---|---|
| | | Mutation | Template | Y407T (hole) | Q347E | Y349S | Y349A | Y349K | Y349D | R355E | R355D | Q347D |
| B1 | CD3_H-Q347E | NA | NA | * | * | | | | | | | |
| B2 | CD3_Q347E | T407Y | CD3_H-Q347E (B1) | | * | | | | | | | |
| B3 | CD3_WT | E347Q | CD3_Q347E (B2) | | | | | | | | | |
| B4 | CD3_Y349S | Y349S | CD3_WT (B3) | | | * | | | | | | |
| B5 | CD3_Y349A | Y349A | CD3_WT (B3) | | | | * | | | | | |
| B6 | CD3_Y329K | Y349K | CD3_WT (B3) | | | | | * | | | | |
| B7 | CD3_Y349D | Y349D | CD3_WT (B3) | | | | | | * | | | |
| B8 | CD3_R355E | R355E | CD3_WT (B3) | | | | | | | * | | |
| B9 | CD3_R355D | R355D | CD3_WT (B3) | | | | | | | | * | |
| B10 | CD3_Q347D | E347D | CD3_H-Q347E (B1) | * | | | | | | | | * |
| B11 | CD3_Hole | E347Q | CD3_H-Q347E (B1) | * | | | | | | | | |

All the 13 combinations of anti-CD20 and anti-CD3 heavy chains with Fc mutations were recombinantly expressed together with their common light chain. The concentrations of the antibodies in supernatant were measured, which are presented in Table 6.

TABLE 6

| | IgG supernatant concentration of the mutant combinations. | |
| --- | --- | --- |
| | Anti-CD20/CD3 antibody mutant | IgG Concentration in supernatant (ug/ml) |
| 1 | A1B1 | 28.3 |
| 2 | A1B10 | 29.1 |
| 3 | A2B2 | 27 |
| 4 | A2B3 | 30.2 |
| 5 | A2B4 | 36.7 |
| 6 | A3B2 | 28.2 |
| 7 | A4B6 | 27.3 |
| 8 | A4B8 | 27.8 |
| 9 | A4B9 | 28.6 |
| 10 | A5B7 | 28.8 |
| 11 | A6B1 | 39.7 |
| 12 | A7B1 | 33 |
| 13 | A7B5 | 45.5 |

CD20/CD3 bispecific antibodies with the combinations of Fc mutations described above are characterized in further experiments. The activity of CD20/CD3 bispecific antibodies on T cell activation is assessed. Fc mutant combinations that have similar or higher 't' cell activation activity than CD20/CD3 wild-type (A1B1) are identified and selected.

The selected CD20/CD3 mutant combinations are recombinantly expressed, purified, analyzed by SDS-PAGE. Fc mutant combinations that have similar or higher purity (i.e., heterodimer percentage) than A1B1 are identified and selected.

The thermostability and aggregation potential of the selected CD20/CD3 mutant combinations are assessed using the methods described in Example 5, below. Thermostability is assessed by differential scanning fluorimetry and static light scattering. Aggregation potential is assessed by dynamic light scattering (DLS). Mutant combinations that have a thermostability that is similar to or better than A1B1, and aggregation potential that is similar to or lower than A1B1 are identified selected.

Example 5. Materials and Methods

The following example presents materials and methods for producing and characterizing bispecific antibodies.
Recombinant Expression of Bispecific Antibodies by Transfecting EXPI293F™ Cells The GIBCO™ EXPIFECTAMINE™ 293 Transfection Kit (catalog number A14524) was used to expressed bispecific antibodies, as described below.

For each 30-mL transfection, $7.5 \times 10^7$ cells in 25.5 mL of EXPI293™ Expression Medium was used. To transfect cells on the following day, cells were seeded at a density of $2.0 \times 10^6$ viable cells/mL and incubated at 37° C. in a humidified atmosphere of 8% $CO_2$ in air on an orbital shaker rotating at 125 rpm. On the day of transfection, the number and viability of the cells was determined using an automated cell counter or the trypan blue dye exclusion method. To proceed with transfection, the viability of cells must have been greater than 95%. The volume of cell suspension containing the number of cells needed for one transfection ($7.5 \times 10^7$ cells for each 30-mL transfection) was calculated. The appropriate volume of cell suspension was added to each sterile, disposable 125-mL Erlenmeyer shaker flask and the volume was brought to 25.5 mL by adding fresh, pre-warmed EXPI293™ Expression Medium for each 30-mL transfection. The cells were returned to the incubator.

For each 30-mL transfection, lipid-DNA complexes were prepared as follows: 30 µg of plasmid DNA in OPTI- MEM™ I Reduced Serum Medium (Cat. no. 31985-062) was diluted to a total volume of 1.5 mL, and mixed gently. 80 µL of EXPIFECTAMINE™ 293 Reagent was diluted in OPTI-MEM™ I medium to a total volume of 1.5 mL, and mixed gently and incubated for 5 minutes at room temperature. After the 5-minute incubation, the diluted DNA was added to the diluted EXPIFECTAMINE™ 293 Reagent to obtain a total volume of 3 mL, and mixed gently. The DNA-EXPIFECTAMINE™ 293 Reagent mixture was incubated for 20-30 minutes at room temperature to allow the DNA-EXPIFECTAMINE™ 293 Reagent complexes to form.

After the DNA-EXPIFECTAMINE™ 293 Reagent complex incubation was complete, 3 mL of DNA-EXPIFECTAMINE™ 293 Reagent complex was added to each shaker flask from the prepared lipid-DNA complexes described above. To the negative control flask, 3 mL of OPTI-MEM™ I medium was added instead of DNA-EXPIFECTAMINE™ 293 Reagent complex. Each flask contained a total volume of 28.5 mL. Cells were incubated in a 37° C. incubator with a humidified atmosphere of 8% $CO_2$ in air on an orbital shaker rotating at 125 rpm.

Approximately 16-18 hours post-transfection, 150 µL of EXPIFECTAMINE™ 293 Transfection Enhancer 1 and 1.5 mL of EXPIFECTAMINE™ 293 Transfection Enhancer 2 were added to each flask. The final volume was approximately 30 mL in each 125-mL flask. Media was harvested beginning at approximately 72-96 hours post-transfection and assayed for recombinant protein expression.
Purification of Bispecific Antibodies with Protein A Columns To purify bispecific antibodies on a Protein A column, 72-96 hours after transfection, the expression medium was centrifuged at 3000 rpm for 10 minutes, and then the supernatant was filtered with 0.45 µm membrane.

An ÅKTA pure protein purification system was used as follows. The ÅKTA purification system was balanced, pump B was filled with Buffer B (0.1M Glycine, pH=2.5) and pump A and sample pump were filled with Buffer A (PBS, pH=7.4). The Protein A purification column (HiTrap Protein A HP column from GE. Ca #:17040201 or 17040301) was then set up and balanced with 10 Column Volume (CV) of Buffer A. Supernatant was loaded to the column through the sample pump, with a flow rate at 1 ml/minute for a 1 ml column and 3 ml/minute for a 5 ml column. The column was washed with Buffer A for 10 CV after sample loading. Antibody was eluted with 100% Buffer B, and the peak fractions were collected with 1/10 volume of 1 M Tris pH=8. The column was washed with 5 CV of Buffer B, and then with 10 CV of Buffer A. The column was stored filled with 20% Ethanol at 4° C., and the ÅKTA system was stored filled with 20% Ethanol.

The selected peak fractions of the eluted Ab were combined and dialyze in PBS twice. The purified antibody was then ready for second step of purification.
Second Purification of Bispecific Antibodies Via Cation Exchange Chromatography (CEX)

Antibody was diluted (in PBS) 1:10 to buffer 1 (20 mM NaxH(3-x)PO4, pH=7.4). The ÅKTA purification system was balanced, pump B was filled with Buffer 2 (20 mM NaxH(3-x)PO4, 1M NaCl, pH=7.4) and pump A and sample pump were filled with Buffer 1. The POROS™ GOPURE™ HS Pre-packed Column (Thermofisher, Cat #: A36637) was set up and balanced with Buffer 1.

The diluted antibody sample was loaded to the column via sample pump, with a flow rate at 1.6 ml/minute, and washed with Buffer 1 for 5 CV after sample loading. For salt gradient elution 0-20% Buffer 2 was used in 40 minutes, at a flow rate of 1.6 ml/minute. Peak fractions were collected (usually 1 ml/vial). The column was washed with 5 CV of Buffer 2, and then washed with 10 CV of Buffer 1. The column was stored filled with 20% ethanol at 4° C., and the ÅKTA system was balanced in 20% Ethanol. The peak fractions were combined and dialyzed to PBS.

SDS-PAGE Assay

For non-reduced SDS-PAGE, 4× loading buffer was added to the sample to achieve 1× sample ready for loading. For reduced SDS-PAGE, 8% volume of beta-mercaptoethanol was added to the samples, mixed well, heated at 95° C. for 5 minutes, then the samples were ready for loading. Samples were loaded to the gel wells, alongside a Protein Marker. Samples were run at 200V for 50 minutes. Gels were stained with INSTANTBLUE™ Protein Stain solution for 1 hour and then washed with water one time.

Thermostability (DST/SLS) and Aggregation Potential (DLS) Assays

The purified bispecific antibody samples were submitted to the UNcle system (Unchained Labs) for analysis. The dynamic light scattering (DLS) was measured at 25° C. and the data were calculated and analyzed using UNcle Analysis Software. For differential scanning fluorimetryl static light scattering (DST/SLS) assays, a temperature ramp of was performed with monitoring from 25° C. to 9.5°. UNcle measured SLS at 266 nm and 473 nm. $T_m$ and $T_{agg}$ were also calculated and analyzed by using the UNcle Analysis Software.

---

What is claimed is:

1. A heteromultimeric protein comprising a first polypeptide comprising a first IgG heavy chain constant domain 3 (CH3) domain and a second polypeptide comprising a second IgG CH3 domain, wherein the first IgG CH3 domain comprises a substitution relative to a wildtype IgG CH3 domain at position 354 with an aromatic hydrophobic amino acid, and the second IgG CH3 domain comprises a substitution relative to a wildtype IgG CH3 domain at amino acid position 347 with a negatively charged amino acid, wherein the first IgG CH3 domain comprises a lysine (K) at amino acid position 360, and wherein the amino acid residue numbering is based on EU numbering.

2. The heteromultimeric protein of claim 1, wherein the second IgG CH3 domain comprises a tyrosine (Y) at amino acid position 349.

3. The heteromultimeric protein of claim 1, wherein the first IgG CH3 domain comprises a substitution selected from the group consisting of S354Y, S354F and S354W.

4. The heteromultimeric protein of claim 1, wherein the second IgG CH3 domain comprises a substitution selected from the group consisting of Q347E and Q347D.

5. The heteromultimeric protein of claim 1, wherein the first IgG CH3 domain and the second IgG CH3 domain further comprise knob-into-hole residues.

6. The heteromultimeric protein of claim 1, wherein the first polypeptide is an antibody heavy chain, and the second polypeptide is an antibody heavy chain.

7. The heteromultimeric protein of claim 6, wherein the heteromultimeric protein comprises one or more antibody light chains.

8. The heteromultimeric protein of claim 7, comprising:
(a) a first heavy chain comprising from the N-terminus to the C-terminus: a first heavy chain variable domain (VH1), a first heavy chain constant domain 1 (CH1), a first heavy chain constant domain 2 (CH2), and the first CH3 domain;
(b) a first light chain comprising from the N-terminus to the C-terminus: a first light chain variable domain (VL1), and a first light chain constant domain (CL);
(c) a second heavy chain comprising from the N-terminus to the C-terminus: a second heavy chain variable domain (VH2), a second CH1, a second CH2, and the second CH3 domain; and
(d) a second light chain comprising from the N-terminus to the C-terminus: a second light chain variable domain (VL2), and a second CL;

wherein VH1 and VL1 associate to form a first antigen binding site that specifically binds to a first target, and VH2 and VL2 associate to form a second antigen binding site that specifically binds to a second target.

9. The heteromultimeric protein of claim 8, wherein the first antigen binding site specifically binds a tumor antigen and the second antigen binding site specifically binds CD3.

10. The heteromultimeric protein of claim 8, comprising:
(a) a first heavy chain comprising from the N-terminus to the C-terminus: a third heavy chain variable domain (VH3), a third CH1, the VH1, the first CH1, the first CH2, and the first CH3 domain;
(b) a first light chain comprising from the N-terminus to the C-terminus: a third light chain variable domain VL3, a third CL, the VL1, and the first CL;
wherein VH3 and VL3 associate to form a third antigen binding site that specifically binds to a third target.

11. The heteromultimeric protein of claim 7, comprising:
(a) a first heavy chain comprising from the N-terminus to the C-terminus: a first VHH, a first heavy chain constant domain 2 (CH2), and the first CH3 domain;
(b) a second heavy chain comprising from the N-terminus to the C-terminus: a first heavy chain variable domain (VH1), a second CH1, a second CH2, and the second CH3 domain; and
(c) a light chain comprising from the N-terminus to the C-terminus: a first light chain variable domain (VL1), and a first CL;
wherein VH1 and VL1 associate to form a first antigen binding site that specifically binds to a first target, and the first VHH specifically binds to a second target.

12. The heteromultimeric protein of claim 1, wherein the heteromultimeric protein is an immunoadhesin or an antibody-immunoadhesin chimera.

13. One or more nucleic acid(s) encoding the heteromultimeric protein of claim 1.

14. A vector comprising the one or more nucleic acid(s) of claim 13.

15. A host cell comprising the one or more nucleic acid(s) of claim 13.

16. A method for preparing a multispecific antibody or a heteromultimeric protein, comprising:
(a) culturing the host cell of claim 15 under conditions that allow expression of the one or more nucleic acid(s) or vector; and
(b) recovering the multispecific antibody or the heteromultimeric protein from the host cell culture.

17. A pharmaceutical composition comprising the hetero-multimeric protein of claim 1, and a pharmaceutically acceptable excipient.

18. A method for treating a subject in need thereof, comprising administering to the subject an effective amount of the pharmaceutical composition of claim 17.

19. A method of generating a heteromultimeric protein that specifically binds to a first target and a second target, comprising:

(a) providing a first polypeptide comprising a first binding domain that specifically binds to the first target, and a first IgG CH3 domain; and (b) providing a second polypeptide comprising a second binding domain that specifically binds to the second target, and a second IgG CH3 domain;

wherein:

(i) the first IgG CH3 domain comprises a substitution relative to a wildtype IgG CH3 domain at position 354 with an aromatic hydrophobic amino acid, wherein the first IgG CH3 domain comprises a lysine (K) at amino acid position 360, and the second IgG CH3 domain comprises a substitution relative to a wildtype IgG CH3 domain at amino acid position 347 with a negatively charged amino acid; or (ii) the first IgG CH3 domain comprises a substitution relative to a wildtype IgG CH3 domain at position 347 with a negatively charged amino acid, and the second IgG CH3 domain comprises a substitution relative to a wildtype IgG CH3 domain at amino acid position 354 with an aromatic hydrophobic amino acid, wherein the second IgG CH3 domain comprises a lysine (K) at amino acid position 360;

and wherein the amino acid residue numbering is based on EU numbering.

* * * * *

SEQUENCE LISTING

```
<160> NUMBER OF SEQ ID NOS: 18

<210> SEQ ID NO 1
<211> LENGTH: 221
<212> TYPE: PRT
<213> ORGANISM: Artificial Sequence
<220> FEATURE:
<223> OTHER INFORMATION: Synthetic Construct

<400> SEQUENCE: 1

Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
        35                  40                  45

Phe Asn Trp Tyr Val Asp Gly Val Glu Val His Asn Ala Lys Thr Lys
    50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Tyr
            115                 120                 125

Arg Glu Glu Met Thr Lys Asn Gln Val Ser Leu Tyr Cys Leu Val Lys
        130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 2
<211> LENGTH: 221
<212> TYPE: PRT
<213> ORGANISM: Artificial Sequence
<220> FEATURE:
```

-continued

<223> OTHER INFORMATION: Synthetic Construct

<400> SEQUENCE: 2

```
Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
            35                  40                  45

Phe Asn Trp Tyr Val Asp Gly Val Glu Val His Asn Ala Lys Thr Lys
        50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Glu Val Tyr Thr Leu Pro Pro Ser
            115                 120                 125

Arg Glu Glu Met Thr Lys Asn Gln Val Ser Leu Thr Cys Leu Val Lys
        130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Thr Ser Lys Leu Thr Val Asp Lys Ser Arg Trp Gln
            180                 185                 190

Gln Gly Asn Val Phe Ser Cys Ser Val Met His Glu Ala Leu His Asn
            195                 200                 205

His Tyr Thr Gln Lys Ser Leu Ser Leu Ser Pro Gly Lys
        210                 215                 220
```

<210> SEQ ID NO 3
<211> LENGTH: 221
<212> TYPE: PRT
<213> ORGANISM: Artificial Sequence
<220> FEATURE:
<223> OTHER INFORMATION: Synthetic Construct

<400> SEQUENCE: 3

```
Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
            35                  40                  45

Phe Asn Trp Tyr Val Asp Gly Val Glu Val His Asn Ala Lys Thr Lys
        50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Tyr
            115                 120                 125
```

```
Arg Glu Glu Met Thr Lys Asn Gln Val Ser Leu Thr Cys Leu Val Lys
    130                 135             140

Gly Phe Tyr Pro Ser Asp Ile Ala Val Glu Trp Glu Ser Asn Gly Gln
145             150                 155                 160

Pro Glu Asn Asn Tyr Lys Thr Thr Pro Pro Val Leu Asp Ser Asp Gly
                165             170             175

Ser Phe Phe Leu Thr Ser Lys Leu Thr Val Asp Lys Ser Arg Trp Gln
            180             185             190

Gln Gly Asn Val Phe Ser Cys Ser Val Met His Glu Ala Leu His Asn
        195             200             205

His Tyr Thr Gln Lys Ser Leu Ser Leu Ser Pro Gly Lys
    210             215             220
```

<210> SEQ ID NO 4
<211> LENGTH: 221
<212> TYPE: PRT
<213> ORGANISM: Artificial Sequence
<220> FEATURE:
<223> OTHER INFORMATION: Synthetic Construct

<400> SEQUENCE: 4

```
Pro Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20              25              30

Val Thr Cys Val Val Val Asp Val Ser His Glu Asp Pro Glu Val Lys
        35              40              45

Phe Asn Trp Tyr Val Asp Gly Val Glu Val His Asn Ala Lys Thr Lys
    50              55              60

Pro Arg Glu Glu Gln Tyr Asn Ser Thr Tyr Arg Val Val Ser Val Leu
65              70              75                  80

Thr Val Leu His Gln Asp Trp Leu Asn Gly Lys Glu Tyr Lys Cys Lys
            85              90              95

Val Ser Asn Lys Ala Leu Pro Ala Pro Ile Glu Lys Thr Ile Ser Lys
            100             105             110

Ala Lys Gly Gln Pro Arg Glu Pro Glu Val Tyr Thr Leu Pro Pro Ser
        115             120             125

Arg Glu Glu Met Thr Lys Asn Gln Val Ser Leu Tyr Cys Leu Val Lys
    130                 135             140

Gly Phe Tyr Pro Ser Asp Ile Ala Val Glu Trp Glu Ser Asn Gly Gln
145             150                 155                 160

Pro Glu Asn Asn Tyr Lys Thr Thr Pro Pro Val Leu Asp Ser Asp Gly
                165             170             175

Ser Phe Phe Leu Tyr Ser Lys Leu Thr Val Asp Lys Ser Arg Trp Gln
            180             185             190

Gln Gly Asn Val Phe Ser Cys Ser Val Met His Glu Ala Leu His Asn
        195             200             205

His Tyr Thr Gln Lys Ser Leu Ser Leu Ser Pro Gly Lys
    210             215             220
```

<210> SEQ ID NO 5
<211> LENGTH: 206
<212> TYPE: PRT
<213> ORGANISM: Homo sapiens

<400> SEQUENCE: 5

```
Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
            35                  40                  45

Asn Ala Lys Thr Lys Pro Arg Glu Glu Gln Tyr Asn Ser Thr Tyr Arg
        50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu Pro Gln Val Tyr
                100                 105                 110

Thr Leu Pro Pro Ser Arg Asp Glu Leu Thr Lys Asn Gln Val Ser Leu
            115                 120                 125

Thr Cys Leu Val Lys Gly Phe Tyr Pro Ser Asp Ile Ala Val Glu Trp
        130                 135                 140

Glu Ser Asn Gly Gln Pro Glu Asn Asn Tyr Lys Thr Thr Pro Pro Val
145                 150                 155                 160

Leu Asp Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
                180                 185                 190

Glu Ala Leu His Asn His Tyr Thr Gln Lys Ser Leu Ser Leu
                195                 200                 205

<210> SEQ ID NO 6
<211> LENGTH: 206
<212> TYPE: PRT
<213> ORGANISM: Homo sapiens

<400> SEQUENCE: 6

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
            35                  40                  45

Asn Ala Lys Thr Lys Pro Arg Glu Glu Gln Phe Asn Ser Thr Phe Arg
        50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys Gly Gln Pro Arg Glu Pro Gln Val Tyr
                100                 105                 110

Thr Leu Pro Pro Ser Arg Glu Glu Met Thr Lys Asn Gln Val Ser Leu
            115                 120                 125

Thr Cys Leu Val Lys Gly Phe Tyr Pro Ser Asp Ile Ala Val Glu Trp
        130                 135                 140

Glu Ser Asn Gly Gln Pro Glu Asn Asn Tyr Lys Thr Thr Pro Pro Met
145                 150                 155                 160

Leu Asp Ser Asp Gly Ser Phe Phe Leu Tyr Ser Lys Leu Thr Val Asp
                165                 170                 175
```

-continued

```
Lys Ser Arg Trp Gln Gln Gly Asn Val Phe Ser Cys Ser Val Met His
        180                 185                 190

Glu Ala Leu His Asn His Tyr Thr Gln Lys Ser Leu Ser Leu
        195                 200                 205

<210> SEQ ID NO 7
<211> LENGTH: 206
<212> TYPE: PRT
<213> ORGANISM: Homo sapiens

<400> SEQUENCE: 7

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
        20                  25                  30

Asp Pro Glu Val Gln Phe Lys Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Thr Lys Gly Gln Pro Arg Glu Pro Gln Val Tyr
            100                 105                 110

Thr Leu Pro Pro Ser Arg Glu Glu Met Thr Lys Asn Gln Val Ser Leu
        115                 120                 125

Thr Cys Leu Val Lys Gly Phe Tyr Pro Ser Asp Ile Ala Val Glu Trp
    130                 135                 140

Glu Ser Ser Gly Gln Pro Glu Asn Asn Tyr Asn Thr Thr Pro Pro Met
145                 150                 155                 160

Leu Asp Ser Asp Gly Ser Phe Phe Leu Tyr Ser Lys Leu Thr Val Asp
                165                 170                 175

Lys Ser Arg Trp Gln Gln Gly Asn Ile Phe Ser Cys Ser Val Met His
        180                 185                 190

Glu Ala Leu His Asn Arg Phe Thr Gln Lys Ser Leu Ser Leu
        195                 200                 205

<210> SEQ ID NO 8
<211> LENGTH: 206
<212> TYPE: PRT
<213> ORGANISM: Homo sapiens

<400> SEQUENCE: 8

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser Gln Glu
        20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Gly Leu Pro Ser Ser Ile Glu
                85                  90                  95
```

```
Lys Thr Ile Ser Lys Ala Lys Gly Gln Pro Arg Glu Pro Gln Val Tyr
            100                 105                 110

Thr Leu Pro Pro Ser Gln Glu Glu Met Thr Lys Asn Gln Val Ser Leu
            115                 120                 125

Thr Cys Leu Val Lys Gly Phe Tyr Pro Ser Asp Ile Ala Val Glu Trp
        130                 135                 140

Glu Ser Asn Gly Gln Pro Glu Asn Asn Tyr Lys Thr Thr Pro Pro Val
145                 150                 155                 160

Leu Asp Ser Asp Gly Ser Phe Phe Leu Tyr Ser Arg Leu Thr Val Asp
                165                 170                 175

Lys Ser Arg Trp Gln Glu Gly Asn Val Phe Ser Cys Ser Val Met His
            180                 185                 190

Glu Ala Leu His Asn His Tyr Thr Gln Lys Ser Leu Ser Leu
        195                 200                 205

<210> SEQ ID NO 9
<211> LENGTH: 206
<212> TYPE: PRT
<213> ORGANISM: Mus musculus

<400> SEQUENCE: 9

Ser Ser Val Phe Ile Phe Pro Pro Lys Pro Lys Asp Val Leu Thr Ile
1               5                   10                  15

Thr Leu Thr Pro Lys Val Thr Cys Val Val Val Asp Ile Ser Lys Asp
            20                  25                  30

Asp Pro Glu Val Gln Phe Ser Trp Phe Val Asp Asp Val Glu Val His
        35                  40                  45

Thr Ala Gln Thr Gln Pro Arg Glu Glu Gln Phe Asn Ser Thr Phe Arg
        50                  55                  60

Ser Val Ser Glu Leu Pro Ile Met His Gln Asp Trp Leu Asn Gly Lys
65                  70                  75                  80

Glu Phe Lys Cys Arg Val Asn Ser Ala Ala Phe Pro Ala Pro Ile Glu
                85                  90                  95

Lys Thr Ile Ser Lys Thr Lys Gly Arg Pro Lys Ala Pro Gln Val Tyr
            100                 105                 110

Thr Ile Pro Pro Pro Lys Glu Gln Met Ala Lys Asp Lys Val Ser Leu
            115                 120                 125

Thr Cys Met Ile Thr Asp Phe Phe Pro Glu Asp Ile Thr Val Glu Trp
        130                 135                 140

Gln Trp Asn Gly Gln Pro Ala Glu Asn Tyr Lys Asn Thr Gln Pro Ile
145                 150                 155                 160

Met Asp Thr Asp Gly Ser Tyr Phe Val Tyr Ser Lys Leu Asn Val Gln
                165                 170                 175

Lys Ser Asn Trp Glu Ala Gly Asn Thr Phe Thr Cys Ser Val Leu His
            180                 185                 190

Glu Gly Leu His Asn His His Thr Glu Lys Ser Leu Ser His
        195                 200                 205

<210> SEQ ID NO 10
<211> LENGTH: 206
<212> TYPE: PRT
<213> ORGANISM: Mus musculus

<400> SEQUENCE: 10

Pro Ser Val Phe Ile Phe Pro Pro Lys Ile Lys Asp Val Leu Met Ile
1               5                   10                  15
```

-continued

```
Ser Leu Ser Pro Ile Val Thr Cys Val Val Val Asp Val Ser Glu Asp
            20                  25                  30

Asp Pro Asp Val Gln Ile Ser Trp Phe Val Asn Asn Val Glu Val His
            35                  40                  45

Thr Ala Gln Thr Gln Thr His Arg Glu Asp Tyr Asn Ser Thr Leu Arg
    50                  55                  60

Val Val Ser Ala Leu Pro Ile Gln His Gln Asp Trp Met Ser Gly Lys
65                  70                  75                  80

Glu Phe Lys Cys Lys Val Asn Asn Lys Asp Leu Pro Ala Pro Ile Glu
                85                  90                  95

Arg Thr Ile Ser Lys Pro Lys Gly Ser Val Arg Ala Pro Gln Val Tyr
                100                 105                 110

Val Leu Pro Pro Pro Glu Glu Glu Met Thr Lys Lys Gln Val Thr Leu
            115                 120                 125

Thr Cys Met Val Thr Asp Phe Met Pro Glu Asp Ile Tyr Val Glu Trp
    130                 135                 140

Thr Asn Asn Gly Lys Thr Glu Leu Asn Tyr Lys Asn Thr Glu Pro Val
145                 150                 155                 160

Leu Asp Ser Asp Gly Ser Tyr Phe Met Tyr Ser Lys Leu Arg Val Glu
                165                 170                 175

Lys Lys Asn Trp Val Glu Arg Asn Ser Tyr Ser Cys Ser Val Val His
                180                 185                 190

Glu Gly Leu His Asn His His Thr Thr Lys Ser Phe Ser Arg
                195                 200                 205

<210> SEQ ID NO 11
<211> LENGTH: 206
<212> TYPE: PRT
<213> ORGANISM: Mus musculus

<400> SEQUENCE: 11

Pro Ser Val Phe Ile Phe Pro Pro Lys Pro Lys Asp Ala Leu Met Ile
1                   5                   10                  15

Ser Leu Thr Pro Lys Val Thr Cys Val Val Val Asp Val Ser Glu Asp
            20                  25                  30

Asp Pro Asp Val His Val Ser Trp Phe Val Asp Asn Lys Glu Val His
            35                  40                  45

Thr Ala Trp Thr Gln Pro Arg Glu Ala Gln Tyr Asn Ser Thr Phe Arg
    50                  55                  60

Val Val Ser Ala Leu Pro Ile Gln His Gln Asp Trp Met Arg Gly Lys
65                  70                  75                  80

Glu Phe Lys Cys Lys Val Asn Asn Lys Ala Leu Pro Ala Pro Ile Glu
                85                  90                  95

Arg Thr Ile Ser Lys Pro Lys Gly Arg Ala Gln Thr Pro Gln Val Tyr
                100                 105                 110

Thr Ile Pro Pro Pro Arg Glu Gln Met Ser Lys Lys Lys Val Ser Leu
            115                 120                 125

Thr Cys Leu Val Thr Asn Phe Phe Ser Glu Ala Ile Ser Val Glu Trp
    130                 135                 140

Glu Arg Asn Gly Glu Leu Glu Gln Asp Tyr Lys Asn Thr Pro Pro Ile
145                 150                 155                 160

Leu Asp Ser Asp Gly Thr Tyr Phe Leu Tyr Ser Lys Leu Thr Val Asp
                165                 170                 175

Thr Asp Ser Trp Leu Gln Gly Glu Ile Phe Thr Cys Ser Val Val His
```

-continued

```
           180              185              190

Glu Ala Leu His Asn His His Thr Gln Lys Asn Leu Ser Arg
        195              200              205

<210> SEQ ID NO 12
<211> LENGTH: 206
<212> TYPE: PRT
<213> ORGANISM: Rattus norvegicus

<400> SEQUENCE: 12

Pro Ser Val Phe Ile Phe Pro Pro Lys Pro Lys Asp Ile Leu Leu Ile
1               5                   10                  15

Ser Gln Asn Ala Lys Val Thr Cys Val Val Val Asp Val Ser Glu Glu
                20                  25                  30

Glu Pro Asp Val Gln Phe Ser Trp Phe Val Asn Asn Val Glu Val His
            35                  40                  45

Thr Ala Gln Thr Gln Pro Arg Glu Glu Gln Tyr Asn Ser Thr Phe Arg
        50                  55                  60

Val Val Ser Ala Leu Pro Ile Gln His Gln Asp Trp Met Ser Gly Lys
65                  70                  75                  80

Glu Phe Lys Cys Lys Val Asn Asn Lys Ala Leu Pro Ser Pro Ile Glu
                85                  90                  95

Lys Thr Ile Ser Lys Pro Lys Gly Leu Val Arg Lys Pro Gln Val Tyr
                100                 105                 110

Val Met Gly Pro Pro Thr Glu Gln Leu Thr Glu Gln Thr Val Ser Leu
            115                 120                 125

Thr Cys Leu Thr Ser Gly Phe Leu Pro Asn Asp Ile Gly Val Glu Trp
        130                 135                 140

Thr Ser Asn Gly His Ile Glu Lys Asn Tyr Lys Asn Thr Glu Pro Val
145                 150                 155                 160

Met Asp Ser Asp Gly Ser Phe Phe Met Tyr Ser Lys Leu Asn Val Glu
                165                 170                 175

Arg Ser Arg Trp Asp Ser Arg Ala Pro Phe Val Cys Ser Val Val His
            180                 185                 190

Glu Gly Leu His Asn His His Val Glu Lys Ser Ile Ser Arg
        195                 200                 205

<210> SEQ ID NO 13
<211> LENGTH: 206
<212> TYPE: PRT
<213> ORGANISM: Rattus norvegicus

<400> SEQUENCE: 13

Ser Ser Val Phe Ile Phe Pro Pro Lys Thr Lys Asp Val Leu Thr Ile
1               5                   10                  15

Thr Leu Thr Pro Lys Val Thr Cys Val Val Val Asp Ile Ser Gln Asn
                20                  25                  30

Asp Pro Glu Val Arg Phe Ser Trp Phe Ile Asp Asp Val Glu Val His
            35                  40                  45

Thr Ala Gln Thr His Ala Pro Glu Lys Gln Ser Asn Ser Thr Leu Arg
        50                  55                  60

Ser Val Ser Glu Leu Pro Ile Val His Arg Asp Trp Leu Asn Gly Lys
65                  70                  75                  80

Thr Phe Lys Cys Lys Val Asn Ser Gly Ala Phe Pro Ala Pro Ile Glu
                85                  90                  95

Lys Ser Ile Ser Lys Pro Glu Gly Thr Pro Arg Gly Pro Gln Val Tyr
```

-continued

```
              100               105               110

Thr Met Ala Pro Pro Lys Glu Glu Met Thr Gln Ser Gln Val Ser Ile
        115               120               125

Thr Cys Met Val Lys Gly Phe Tyr Pro Pro Asp Ile Tyr Thr Glu Trp
    130               135               140

Lys Met Asn Gly Gln Pro Gln Glu Asn Tyr Lys Asn Thr Pro Pro Thr
145               150               155               160

Met Asp Thr Asp Gly Ser Tyr Phe Leu Tyr Ser Lys Leu Asn Val Lys
                165               170               175

Lys Glu Thr Trp Gln Gln Gly Asn Thr Phe Thr Cys Ser Val Leu His
                180               185               190

Glu Gly Leu His Asn His His Thr Glu Lys Ser Leu Ser His
        195               200               205
```

<210> SEQ ID NO 14
<211> LENGTH: 206
<212> TYPE: PRT
<213> ORGANISM: Oryctolagus cuniculus

<400> SEQUENCE: 14

```
Pro Ser Val Phe Ile Phe Pro Pro Lys Pro Lys Asp Thr Leu Met Ile
1               5                 10                15

Ser Arg Thr Pro Glu Val Thr Cys Val Val Val Asp Val Ser Glu Asp
                20                25                30

Asp Pro Glu Val Gln Phe Thr Trp Tyr Ile Asn Asn Glu Gln Val Arg
        35                40                45

Thr Ala Arg Pro Pro Leu Arg Glu Gln Gln Phe Asn Ser Thr Ile Arg
    50                55                60

Val Val Ser Thr Leu Pro Ile Ala His Glu Asp Trp Leu Arg Gly Lys
65                70                75                80

Glu Phe Lys Cys Lys Val His Asn Lys Ala Leu Pro Ala Pro Ile Glu
                85                90                95

Lys Thr Ile Ser Lys Ala Arg Gly Gln Pro Leu Glu Pro Lys Val Tyr
                100               105               110

Thr Met Gly Pro Pro Arg Glu Glu Leu Ser Ser Arg Ser Val Ser Leu
        115               120               125

Thr Cys Met Ile Asn Gly Phe Tyr Pro Ser Asp Ile Ser Val Glu Trp
    130               135               140

Glu Lys Asn Gly Lys Ala Glu Asp Asn Tyr Lys Thr Thr Pro Ala Val
145               150               155               160

Leu Asp Ser Asp Gly Ser Tyr Phe Leu Tyr Ser Lys Leu Ser Val Pro
                165               170               175

Thr Ser Glu Trp Gln Arg Gly Asp Val Phe Thr Cys Ser Val Met His
                180               185               190

Glu Ala Leu His Asn His Tyr Thr Gln Lys Ser Ile Ser Arg
        195               200               205
```

<210> SEQ ID NO 15
<211> LENGTH: 208
<212> TYPE: PRT
<213> ORGANISM: Bos taurus

<400> SEQUENCE: 15

```
Pro Ser Val Phe Ile Phe Pro Pro Lys Pro Lys Asp Thr Leu Thr Ile
1               5                 10                15

Ser Gly Thr Pro Glu Val Thr Cys Val Val Val Asp Val Gly His Asp
```

-continued

```
              20                 25                 30

Asp Pro Glu Val Lys Phe Ser Trp Phe Val Asp Asp Val Glu Val Asn
              35                 40                 45

Thr Ala Thr Thr Lys Pro Arg Glu Glu Gln Phe Asn Ser Thr Tyr Arg
        50                 55                 60

Val Val Ser Ala Leu Arg Ile Gln His Gln Asp Trp Thr Gly Gly Lys
65                    70                 75                    80

Glu Phe Lys Cys Lys Val His Asn Glu Gly Leu Pro Ala Pro Ile Val
                  85                 90                    95

Arg Thr Ile Ser Arg Thr Lys Gly Pro Ala Arg Glu Pro Gln Val Tyr
                  100                105                110

Val Leu Ala Pro Pro Gln Glu Glu Leu Ser Lys Ser Thr Val Ser Leu
              115                120                125

Thr Cys Met Val Thr Ser Phe Tyr Pro Asp Tyr Ile Ala Val Glu Trp
        130                135                140

Gln Arg Asn Gly Gln Pro Glu Ser Glu Asp Lys Tyr Gly Thr Thr Pro
145                150                155                   160

Pro Gln Leu Asp Ala Asp Gly Ser Tyr Phe Leu Tyr Ser Arg Leu Arg
                  165                170                175

Val Asp Arg Asn Ser Trp Gln Glu Gly Asp Thr Tyr Thr Cys Val Val
                  180                185                190

Met His Glu Ala Leu His Asn His Tyr Thr Gln Lys Ser Thr Ser Lys
                  195                200                205

<210> SEQ ID NO 16
<211> LENGTH: 208
<212> TYPE: PRT
<213> ORGANISM: Bos taurus

<400> SEQUENCE: 16

Pro Ser Val Phe Ile Phe Pro Pro Lys Pro Lys Asp Thr Leu Met Ile
1                 5                 10                 15

Thr Gly Thr Pro Glu Val Thr Cys Val Val Val Asn Val Gly His Asp
              20                 25                 30

Asn Pro Glu Val Gln Phe Ser Trp Phe Val Asp Asp Val Glu Val His
              35                 40                 45

Thr Ala Arg Ser Lys Pro Arg Glu Glu Gln Phe Asn Ser Thr Tyr Arg
        50                 55                 60

Val Val Ser Ala Leu Pro Ile Gln His Gln Asp Trp Thr Gly Gly Lys
65                    70                 75                    80

Glu Phe Lys Cys Lys Val Asn Asn Lys Gly Leu Ser Ala Pro Ile Val
                  85                 90                    95

Arg Ile Ile Ser Arg Ser Lys Gly Pro Ala Arg Glu Pro Gln Val Tyr
                  100                105                110

Val Leu Asp Pro Pro Lys Glu Glu Leu Ser Lys Ser Thr Leu Ser Val
              115                120                125

Thr Cys Met Val Thr Gly Phe Tyr Pro Glu Asp Val Ala Val Glu Trp
        130                135                140

Gln Arg Asn Arg Gln Thr Glu Ser Glu Asp Lys Tyr Arg Thr Thr Pro
145                150                155                   160

Pro Gln Leu Asp Thr Asp Arg Ser Tyr Phe Leu Tyr Ser Lys Leu Arg
                  165                170                175

Val Asp Arg Asn Ser Trp Gln Glu Gly Asp Ala Tyr Thr Cys Val Val
                  180                185                190
```

```
Met His Glu Ala Leu His Asn His Tyr Met Gln Lys Ser Thr Ser Lys
        195                 200                 205

<210> SEQ ID NO 17
<211> LENGTH: 208
<212> TYPE: PRT
<213> ORGANISM: Felis catus

<400> SEQUENCE: 17

Pro Ser Ile Phe Ile Phe Pro Pro Lys Pro Lys Asp Thr Leu Ser Ile
1               5                   10                  15

Ser Arg Thr Pro Glu Val Thr Cys Leu Val Val Asp Leu Gly Pro Asp
            20                  25                  30

Asp Ser Asp Val Gln Ile Thr Trp Phe Val Asp Asn Thr Gln Val Tyr
        35                  40                  45

Thr Ala Lys Thr Ser Pro Arg Glu Glu Gln Phe Asn Ser Thr Tyr Arg
        50                  55                  60

Val Val Ser Val Leu Pro Ile Leu His Gln Asp Trp Leu Lys Gly Lys
65                  70                  75                  80

Glu Phe Lys Cys Lys Val Asn Ser Lys Ser Leu Pro Ser Pro Ile Glu
                85                  90                  95

Arg Thr Ile Ser Lys Asp Lys Gly Gln Pro His Glu Pro Gln Val Tyr
                100                 105                 110

Val Leu Pro Pro Ala Gln Glu Glu Leu Ser Arg Asn Lys Val Ser Val
            115                 120                 125

Thr Cys Leu Ile Glu Gly Phe Tyr Pro Pro Asp Ile Ala Val Glu Trp
        130                 135                 140

Glu Ile Thr Gly Gln Pro Glu Pro Glu Asn Asn Tyr Arg Thr Thr Pro
145                 150                 155                 160

Pro Gln Leu Asp Ser Asp Gly Thr Tyr Phe Leu Tyr Ser Arg Leu Ser
                165                 170                 175

Val Asp Arg Ser Arg Trp Gln Arg Gly Asn Thr Tyr Thr Cys Ser Val
                180                 185                 190

Ser His Glu Ala Leu His Ser His His Thr Gln Lys Ser Leu Thr Gln
        195                 200                 205

<210> SEQ ID NO 18
<211> LENGTH: 209
<212> TYPE: PRT
<213> ORGANISM: Canis lupus familiaris

<400> SEQUENCE: 18

Pro Ser Val Leu Ile Phe Pro Pro Lys Pro Lys Asp Ile Leu Arg Ile
1               5                   10                  15

Thr Arg Thr Pro Glu Val Thr Cys Val Val Leu Asp Leu Gly Arg Glu
            20                  25                  30

Asp Pro Glu Val Gln Ile Ser Trp Phe Val Asp Gly Lys Glu Val His
        35                  40                  45

Thr Ala Lys Thr Gln Ser Arg Glu Gln Gln Phe Asn Gly Thr Tyr Arg
        50                  55                  60

Val Val Ser Val Leu Pro Ile Glu His Gln Asp Trp Leu Thr Gly Lys
65                  70                  75                  80

Glu Phe Lys Cys Arg Val Asn His Ile Asp Leu Pro Ser Pro Ile Glu
                85                  90                  95

Arg Thr Ile Ser Lys Ala Arg Gly Arg Ala His Lys Pro Ser Val Tyr
                100                 105                 110
```

-continued

```
Val Leu Pro Pro Ser Pro Lys Glu Leu Ser Ser Ser Asp Thr Val Ser
        115             120                     125

Ile Thr Cys Leu Ile Lys Asp Phe Tyr Pro Pro Asp Ile Asp Val Glu
        130             135             140

Trp Gln Ser Asn Gly Gln Gln Glu Pro Glu Arg Lys His Arg Met Thr
145                 150                 155                 160

Pro Pro Gln Leu Asp Glu Asp Gly Ser Tyr Phe Leu Tyr Ser Lys Leu
                165             170                 175

Ser Val Asp Lys Ser Arg Trp Gln Gln Gly Asp Pro Phe Thr Cys Ala
                180             185                 190

Val Met His Glu Thr Leu Gln Asn His Tyr Thr Asp Leu Ser Leu Ser
        195             200                     205

His
```